(12) United States Patent
Zhang et al.

(10) Patent No.: US 9,233,098 B2
(45) Date of Patent: Jan. 12, 2016

(54) NITROGEN-CONTAINING FUSED RING COMPOUNDS AS CRTH2 ANTAGONISTS

(71) Applicant: KBP Biosciences Co., Ltd., Jinan, Shandong (CN)

(72) Inventors: Yan Zhang, Jinan (CN); Min Zhang, Jinan (CN); Hoyin Lo, Jinan (CN)

(73) Assignee: KBP BIOSCIENCES CO., LTD., Jinan (CN)

( * ) Notice: Subject to any disclaimer, the term of this patent is extended or adjusted under 35 U.S.C. 154(b) by 0 days.

(21) Appl. No.: 14/357,996

(22) PCT Filed: Nov. 16, 2012

(86) PCT No.: PCT/CN2012/084756
§ 371 (c)(1),
(2) Date: May 13, 2014

(87) PCT Pub. No.: WO2013/071880
PCT Pub. Date: May 23, 2013

(65) Prior Publication Data
US 2014/0303186 A1    Oct. 9, 2014

(30) Foreign Application Priority Data

Nov. 17, 2011 (CN) .......................... 2011 1 0364581
Sep. 3, 2012 (CN) .......................... 2012 1 0319955

(51) Int. Cl.
| | |
|---|---|
| A61K 31/405 | (2006.01) |
| A61K 31/416 | (2006.01) |
| A61K 31/437 | (2006.01) |
| A61K 45/06 | (2006.01) |
| C07D 209/14 | (2006.01) |
| C07D 209/22 | (2006.01) |
| C07D 231/56 | (2006.01) |
| C07D 401/06 | (2006.01) |
| C07D 401/12 | (2006.01) |
| C07D 403/06 | (2006.01) |
| C07D 471/04 | (2006.01) |
| C07D 405/12 | (2006.01) |
| A61K 31/4439 | (2006.01) |
| A61K 31/497 | (2006.01) |

(52) U.S. Cl.
CPC ............ *A61K 31/405* (2013.01); *A61K 31/416* (2013.01); *A61K 31/437* (2013.01); *A61K 31/4439* (2013.01); *A61K 31/497* (2013.01); *A61K 45/06* (2013.01); *C07D 209/14* (2013.01); *C07D 209/22* (2013.01); *C07D 231/56* (2013.01); *C07D 401/06* (2013.01); *C07D 401/12* (2013.01); *C07D 403/06* (2013.01); *C07D 405/12* (2013.01); *C07D 471/04* (2013.01)

(58) Field of Classification Search
CPC . A61K 31/405; A61K 31/416; A61K 31/437; A61K 45/06; C07D 209/14; C07D 209/22; C07D 231/56; C07D 401/06; C07D 401/12; C07D 403/06; C07D 471/04

See application file for complete search history.

(56) References Cited

U.S. PATENT DOCUMENTS

| | | |
|---|---|---|
| 8,394,836 B2 | 3/2013 | Hynd et al. |
| 2009/0030014 A1 | 1/2009 | Kugimiya et al. |
| 2009/0186923 A1 | 7/2009 | Armer et al. |
| 2010/0330077 A1 | 12/2010 | Armer et al. |

FOREIGN PATENT DOCUMENTS

| | | | |
|---|---|---|---|
| CN | 101166721 A | 4/2008 | |
| CN | 101932571 A | 12/2010 | |
| CN | 101970405 | * 2/2011 | .......... A61K 31/404 |
| CN | 101970405 | 2/2011 | |
| JP | 2008-532990 A | 8/2008 | |
| JP | 2010-540520 A | 12/2010 | |
| JP | 2011-506415 A | 3/2011 | |
| WO | 2007/065683 A1 | 6/2007 | |
| WO | 2007/065684 A2 | 6/2007 | |
| WO | 2007/065924 A1 | 6/2007 | |
| WO | 2009/077728 A1 | 6/2009 | |
| WO | 2009/090414 A1 | 7/2009 | |
| WO | 2010/074244 A1 | 7/2010 | |
| WO | 2011/092140 A1 | 8/2011 | |

OTHER PUBLICATIONS

Canadian Office Action dated May 11, 2015, for corresponding CA Application No. 2,856,100, 3 pages.

(Continued)

*Primary Examiner* — Erich A Leeser
(74) *Attorney, Agent, or Firm* — Seed IP Law Group PLLC

(57) ABSTRACT

The present application relates to nitrogen-containing fused ring compounds shown by general formula (I), a pharmaceutically acceptable salt thereof and a stereoisomer thereof as CRTH2 antagonist, wherein $X^1$, $X^2$, $X^3$, $X^4$, $X^5$, W, X, Y, $L^1$, $L^2$, $L^3$, A, B are as defined in the description; the present application further relates to a method for preparing the compounds, a pharmaceutical formulation and a pharmaceutical composition comprising the compounds, a use of the compounds for the manufacture of a medicament for the treatment and/or prevention of diseases related to activity of CRTH2.

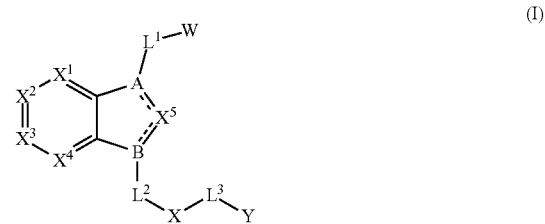

7 Claims, No Drawings

(56) References Cited

OTHER PUBLICATIONS

Chinese Office Action dated Dec. 26, 2014, for corresponding CN Application No. 201280055917.0, with English Translation, 11 pages.
Chinese Office Action dated Jun. 16, 2015, for corresponding CN Application No. 201280055917.0, with English Translation, 15 pages.
Extended European Search Report, dated Mar. 31, 2015, for corresponding EP Application No. 12850344.8-1462, 10 pages.
Japanese Office Action, dated Apr. 13, 2015, for corresponding JP Application No. 2014-541525, with English Translation, 4 pages.
ACS STN Tokyo, "1H-Indole-1-acetamide, 3-[[4-[(cyclopentylcarbonyl)aminol-1-piperidinyl]methyl]-N-(1-methylethyl)-" registry No. 1287448-23-0, Apr. 29, 2011, 1 page.

* cited by examiner

NITROGEN-CONTAINING FUSED RING COMPOUNDS AS CRTH2 ANTAGONISTS

TECHNICAL FIELD

The present invention involves in the technical field of pharmaceuticals, and specifically relates to nitrogen-containing fused ring compounds as CRTH2 antagonists, a pharmaceutically acceptable salt thereof and a stereoisomer thereof, a method for preparing the compounds, a pharmaceutical formulation and a pharmaceutical composition comprising the compounds, and a use of the compounds, the pharmaceutically acceptable salt thereof or the stereoisomer thereof for the manufacture of a medicament for the treatment and/or prevention of diseases related to activity of CRTH2.

BACKGROUND

CRTH2 is a G-protein-coupled chemoattractant receptor, expressed on Th2 cells and eosinophilic granulocytes. Th2-polarization has been observed inallergic diseases, such as asthma, allergic rhinitis, atopic dermatitis and allergic conjunctivitis. Th2 cells generate Th2 cells factors, such as IL-4, IL-5 and IL-3, to regulate allergic diseases. In allergic diseases, these Th2 cells factors directly or indirectly induce immigration, activation, priming and prolonged survival of effector cells, such as eosinophilic granulocytes and basophilic granulocytes.

$PGD_2$ (prostaglandin D2), a ligand for CRTH2, is produced from mast cells and other important effector cells in allergic diseases. In human cells, $PGD_2$ induces immigration and activation of Th2 cells, eosinophilic granulocytes and basophilic via CRTH2. Therefore, antagonists inhibiting the combination of CRTH2 and $PGD_2$ should be useful for the treatment of allergic diseases, such as asthma, allergic rhinitis, atopic dermatitis, and allergic conjunctivitis.

In addition, several series of experiments evidences have demonstrated the role of eosinophilic granulocytes in nasal sinusitis and Churg-Strauss syndrome. In the tissues of these patients, mast cells can be observed to be colocalized with eosinophilic granulocytes. It is suggested that PGD2 production from mast cells induces the recruitment of eosinophilic granulocytes. Therefore, antagonists of CRTH2 receptors are also useful for the treatment of other eosinophilic granulocytes-related diseases such as Churg-Strauss syndrome and nasal sinusitis. CRTH2 antagonists can also be useful for the treatment of some basophilic granulocytes-related diseases such as basophilic leukemia, chronic urticaria and basophilic leukocytosis, because of high expression of CRTH2 on basophilic granulocytes.

Ramatroban is commercially available as an antagonist of thromboxane A2 receptor, having an extremely high effect of activating platelet, and a weak antagonism toward CRTH2 receptors. The selectivity thereof is low, and the main adverse reactions are suggillation, prolonged prothrombin time/activated partial thromboplastin time, and subcutaneous hemorrhage.

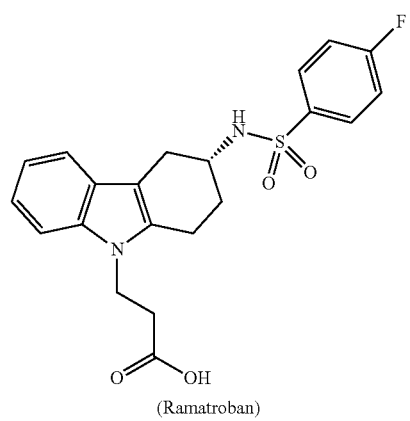 [SMILES: O=C(O)CCn1c2c(c3ccccc31)C[C@H](NS(=O)(=O)c1ccc(F)cc1)CC2]

(Ramatroban)

Currently, there is no medicamentation with an effective antagonism toward CRTH2 in the market. Therefore, there is a need to develop compounds with high selecrivity, high activity, and novel structure, to optimize physical-chemical property and increase druggability.

SUMMARY

The technical problem to be solved by the present application is to provide a nitrogen-containing fused ring compound as CRTH2 antagonists.

Embodiments of the present application are as follows.

A compound shown by general formula (I), a pharmaceutically acceptable salt thereof and a stereoisomer thereof:

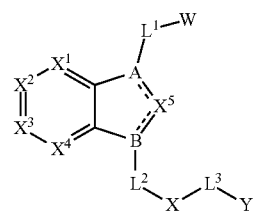

wherein, $X^1$, $X^2$, $X^3$, $X^4$ each independently are N or $C(R^1)$, and $X^5$ is N or $C(R^2)$;

$R^1$ is hydrogen atom, cyano, nitro, hydroxy, carboxy, amino, halogen atom, $C_{1-6}$-alkyl, halo-$C_{1-6}$-alkyl, $C_{3-8}$-cycloalkyl, $C_{1-6}$-alkoxy, halo-$C_{1-6}$-alkoxy, $C_{3-8}$-cycloalkyl-$C_{1-6}$-alkyl, $C_{2-6}$-alkenyl, $C_{5-8}$-cycloalkenyl, $C_{2-6}$-alkynyl, $C_{1-6}$-alkylthio, $C_{1-6}$-alkyl-amino, di($C_{1-6}$-alkyl)amino, $C_{1-6}$-alkyl-carbonyl, $C_{1-6}$-alkyl-carbamoyl, formamido, $C_{1-6}$-alkyl-amido, $C_{1-6}$-alkyl-sulfonyl, $C_{1-6}$-alkyl-aminosulfonyl, $C_{1-6}$-alkyl-sulfonamido, di($C_{1-6}$-alkyl)carbamoyl, di($C_{1-6}$-alkyl)aminosulfonyl, $C_{1-6}$-alkoxy-carbonyl or $C_{1-6}$-alkyl-carbonyloxy;

$R^2$ is hydrogen atom, cyano, nitro, hydroxy, carboxy, amino, halogen atom, $C_{1-6}$-alkyl, halo-$C_{1-6}$-alkyl, $C_{3-8}$-cycloalkyl, $C_{1-6}$-alkoxy, halo-$C_{1-6}$-alkoxy, $C_{3-8}$-cycloalkyl-$C_{1-6}$-alkyl, $C_{2-6}$-alkenyl, $C_{3-8}$-cycloalkyl-$C_{2-6}$-alkenyl, $C_{5-8}$-cycloalkenyl, $C_{5-8}$-cycloalkenyl-$C_{1-6}$-alkyl, $C_{2-6}$-alkynyl, $C_{1-6}$-alkylthio, phenyl, phenyl-$C_{1-6}$-alkyl, naphthyl, $C_{3-8}$-heterocycloalkyl, $C_{3-8}$-heterocycloalkyl-$C_{1-6}$-alkyl, $C_{1-6}$-alkylamino, di($C_{1-6}$-alkyl)amino, $C_{1-6}$-alkyl-carbonyl, $C_{1-6}$-alkyl-carbamoyl, formamido, $C_{1-6}$-alkyl-amido, $C_{1-6}$-alkyl-sulfonyl, $C_{1-6}$-alkyl-aminosulfonyl, $C_{1-6}$-alkyl-sulfonamido, di($C_{1-6}$-alkyl)carbamoyl, di($C_{1-6}$-alkyl)aminosulfonyl, $C_{1-6}$-alkoxy-carbonyl or $C_{1-6}$-alkyl-carbonyloxy;

-A═ and —B═ each independently are —N— or —C═, and -A═ and —B═ are not simultaneously —N—;

$L^1$ is —$(C(R^{1a}R^{1b}))_p$—, and p is 1, 2, 3, 4, 5 or 6;
when $$—A═ \quad is \quad —C═,$$

$R^{1a}$ and $R^{1b}$ each independently are hydrogen atom, halogen atom, hydroxy, $C_{1-6}$-alkyl, halo-$C_{1-6}$-alkyl, $C_{1-6}$-alkoxy, halo-$C_{1-6}$-alkoxy or $C_{3-8}$-cycloalkyl, wherein $R^{1a}$ and $R^{1b}$ can form $C_{3-8}$-cycloalkyl or $C_{3-8}$-heterocycloalkyl containing at least one O, N or S atom with the carbon to which they are attached, and the $C_{3-8}$-cycloalkyl and $C_{3-8}$-heterocycloalkyl optionally can be substituted with 1, 2, 3, 4, 5 or 6 substituents independently selected from the following substituents: halogen atom, hydroxy, $C_{1-6}$-alkyl, halo-$C_{1-6}$-alkyl, $C_{1-6}$-alkoxy or halo-$C_{1-6}$-alkoxy;

when -A═ is —N—, $R^{1a}$ and $R^{1b}$ each independently are hydrogen atom, $C_{1-6}$-alkyl, halo-$C_{1-6}$-alkyl or $C_{3-8}$-cycloalkyl, wherein $R^{1a}$ and $R^{1b}$ can form $C_{3-8}$-cycloalkyl or $C_{3-8}$-heterocycloalkyl containing at least one O, N or S atom with the carbon to which they are attached, the $C_{3-8}$-cycloalkyl and $C_{3-8}$-heterocycloalkyl optionally can be substituted with 1, 2, 3, 4, 5 or 6 substituents independently selected from the following substituents: halogen atom, hydroxy, $C_{1-6}$-alkyl, halo-$C_{1-6}$-alkyl, $C_{1-6}$-alkoxy or halo-$C_{1-6}$-alkoxy;

W is $R^{2a}OC(O)$—, $(R^{2a})_2NC(O)$—, $R^{2a}C(O)NHC(O)$—, tetrazyl or $R^{2a}S(O)_2NHC(O)$—;

$R^{2a}$ is hydrogen, $C_{1-6}$-alkyl, halo-$C_{1-6}$-alkyl, $C_{3-8}$-cycloalkyl, $C_{3-8}$-heterocycloalkyl, phenyl or tolyl;

$L^2$ is —$(C(R^{3a}R^{3b}))_p$—, and p is 1, 2, 3, 4, 5 or 6;

when —B═ is —C═, $R^{3a}$ and $R^{3b}$ each independently are hydrogen atom, halogen atom, hydroxy, $C_{1-6}$-alkyl, halo-$C_{1-6}$-alkyl or $C_{3-8}$-cycloalkyl, wherein $R^{3a}$ and $R^{3b}$ can form $C_{3-8}$-cycloalkyl or $C_{3-8}$-heterocycloalkyl containing at least one O, N or S atom with the carbon to which they are attached, and the $C_{3-8}$-cycloalkyl and $C_{3-8}$-heterocycloalkyl optionally can be substituted with 1, 2, 3, 4, 5 or 6 substituents independently selected from the following substituents: halogen atom, hydroxy, $C_{1-6}$-alkyl, halo-$C_{1-6}$-alkyl, $C_{1-6}$-alkoxy, halo-$C_{1-6}$-alkoxy or $C_{3-8}$-cycloalkyl;

when —B═ is —N—, $R^{3a}$ and $R^{3b}$ each independently are hydrogen atom, $C_{1-6}$-alkyl, halo-$C_{1-6}$-alkyl or $C_{3-8}$-cycloalkyl, wherein $R^{3a}$ and $R^{3b}$ can form $C_{3-8}$-cycloalkyl or $C_{3-8}$-heterocycloalkyl containing at least one O, N or S atom with the carbon to which they are attached, and the $C_{3-8}$-cycloalkyl and $C_{3-8}$-heterocycloalkyl optionally can be substituted with 1, 2, 3, 4, 5 or 6 substituents independently selected from the following substituents: halogen atom, hydroxy, $C_{1-6}$-alkyl, halo-$C_{1-6}$-alkyl, $C_{1-6}$-alkoxy, halo-$C_{1-6}$-alkoxy or $C_{3-8}$-cycloalkyl;

X is aryl or heterocyclyl, and the X optionally can be substituted with 1, 2, 3, 4, 5 or 6 substituents independently selected from the following substituents: halogen atom, hydroxy, $C_{1-6}$-alkyl, halo-$C_{1-6}$-alkyl, $C_{1-6}$-alkoxy, halo-$C_{1-6}$-alkoxy or $C_{3-8}$-cycloalkyl;

$L^3$ is —$N(R^{5a})$—$C(O)$—, and $R^{5a}$ is hydrogen atom or $C_{1-6}$-alkyl;

Y is $C_{3-8}$-cycloalkyl, aryl or 3-10 heterocyclyl, and the Y optionally can be substituted with 1, 2, 3, 4, 5 or 6 substituents independently selected from the following substituents: hydroxy, halogen atom, cyano, nitro, $C_{1-6}$-alkyl, hydroxyl-$C_{1-6}$-alkyl, halo-$C_{1-6}$-alkyl, $C_{1-6}$-alkoxy, $C_{1-6}$-alkoxy-$C_{1-6}$-alkyl, $C_{1-6}$-alkoxy-$C_{1-6}$-alkoxy, halo-$C_{1-6}$-alkoxy, $C_{3-8}$-cycloalkyl, $C_{1-6}$-alkyl-amino, di($C_{1-6}$-alkyl)amino, $C_{1-6}$-alkylthio, phenyl, phenyloxy, $C_{5-8}$-heterocycloalkyl, $C_{5-8}$-heterocycloalkoxy, $C_{1-6}$-alkyl-carbonyl, $C_{1-6}$-alkyl-carbamoyl, formamido, $C_{1-6}$-alkyl-amido, $C_{1-6}$-alkyl-sulfonyl, $C_{1-6}$-alkyl-aminosulfonyl, $C_{1-6}$-alkyl-sulfonamido, di($C_{1-6}$-alkyl)carbamoyl, di($C_{1-6}$-alkyl)aminosulfonyl, $C_{1-6}$-alkoxy-carbonyl or $C_{1-6}$-alkyl-carbonyloxy.

A preferable embodiment of the compound shown by general formula (I), a pharmaceutically acceptable salt thereof and a stereoisomer thereof is:

wherein, $X^1$, $X^2$, $X^3$, $X^4$ each independently are N or $C(R^1)$, and $X^5$ is N or $C(R^2)$;

$R^1$ is hydrogen atom, cyano, hydroxy, amino, halogen atom, $C_{1-6}$-alkyl, halo-$C_{1-6}$-alkyl, $C_{3-8}$-cycloalkyl, $C_{1-6}$-alkoxy, halo-$C_{1-6}$-alkoxy, $C_{3-8}$-cycloalkyl-$C_{1-6}$-alkyl, $C_{2-6}$-alkenyl, $C_{5-8}$-cycloalkenyl, $C_{1-6}$-alkylthio, $C_{1-6}$-alkyl-amino, di($C_{1-6}$-alkyl)amino, $C_{1-6}$-alkyl-carbamoyl, formamido, $C_{1-6}$-alkyl-amido, $C_{1-6}$-alkyl-aminosulfonyl, $C_{1-6}$-alkyl-sulfonamido, di($C_{1-6}$-alkyl)carbamoyl, di($C_{1-6}$-alkyl)aminosulfonyl, $C_{1-6}$-alkoxy-carbonyl or $C_{1-6}$-alkyl-carbonyloxy;

$R^2$ is hydrogen atom, cyano, amino, nitro, hydroxy, halogen atom, $C_{1-6}$-alkyl, halo-$C_{1-6}$-alkyl, $C_{3-8}$-cycloalkyl, $C_{1-6}$-alkoxy, halo-$C_{1-6}$-alkoxy, $C_{3-8}$-cycloalkyl-$C_{1-6}$-alkyl, $C_{2-6}$-alkenyl, $C_{3-8}$-cycloalkyl-$C_{2-6}$-alkenyl, $C_{5-8}$-cycloalkenyl, $C_{5-8}$-cycloalkenyl-$C_{1-6}$-alkyl, $C_{2-6}$-alkynyl, phenyl, phenyl-$C_{1-6}$-alkyl, naphthyl, $C_{3-8}$-heterocycloalkyl, $C_{3-8}$-heterocycloalkyl-$C_{1-6}$-alkyl, $C_{1-6}$-alkylamino, di($C_{1-6}$-alkyl)amino, $C_{1-6}$-alkyl-carbamoyl, formamido, $C_{1-6}$-alkyl-amido, $C_{1-6}$-alkyl-aminosulfonyl, $C_{1-6}$-alkyl-sulfonamido, di($C_{1-6}$-alkyl)carbamoyl or di($C_{1-6}$-alkyl)aminosulfonyl;

-A═ and —B═ each independently are —N— or —C═, and -A═ and —B═ are not simultaneously —N—;

$L^1$ is —$(C(R^{1a}R^{1b}))_p$—, and p is 1, 2, 3, 4 or 5;

when -A═ is —C═, $R^{1a}$ and $R^{1b}$ each independently are hydrogen atom, halogen atom, hydroxy, $C_{1-6}$-alkyl, halo-$C_{1-6}$-alkyl, $C_{1-6}$-alkoxy or $C_{3-6}$-cycloalkyl, wherein $R^1$ and $R^{1b}$ can form $C_{3-6}$-cycloalkyl or $C_{3-6}$-heterocycloalkyl containing at least one O, N or S atom with the carbon to which they are attached, and the $C_{3-6}$-cycloalkyl and $C_{3-6}$-heterocycloalkyl optionally can be substituted with 1, 2, 3, 4 or 5 substituents independently selected from the following substituents: halogen atom, hydroxy, $C_{1-6}$-alkyl, halo-$C_{1-6}$-alkyl or $C_{1-6}$-alkoxy;

when -A═ is —N—, $R^{1a}$ and $R^{1b}$ each independently are hydrogen atom, $C_{1-6}$-alkyl, halo-$C_{1-6}$-alkyl or $C_{3-6}$-cycloalkyl, wherein $R^{1a}$ and $R^{1b}$ can form $C_{3-6}$-cycloalkyl or $C_{3-6}$-heterocycloalkyl containing at least one O, N or S atom with the carbon to which they are attached, and the $C_{3-6}$-cycloalkyl and $C_{3-6}$-heterocycloalkyl optionally can be substituted with 1, 2, 3, 4 or 5 substituents independently selected from the following substituents: halogen atom, hydroxy, $C_{1-6}$-alkyl, halo-$C_{1-6}$-alkyl, $C_{1-6}$-alkoxy or halo-$C_{1-6}$-alkoxy;

W is $R^{2a}OC(O)$—, $(R^{2a})_2NC(O)$— or tetrazyl, $R^{2a}$ is hydrogen, $C_{1-6}$-alkyl or $C_{3-8}$-cycloalkyl;

$L^2$ is —$(C(R^{3a}R^{3b}))_p$—, and p is 1, 2, 3, 4 or 5;

when —B═ is —C═, $R^{3a}$ and $R^{3b}$ each independently are hydrogen atom, halogen atom, hydroxy, $C_{1-6}$-alkyl or $C_{3-6}$-cycloalkyl, wherein $R^{3a}$ and $R^{3b}$ can form $C_{3-6}$-cycloalkyl or $C_{3-6}$-heterocycloalkyl containing at least one O, N or S atom with the carbon to which they are attached, and the $C_{3-6}$-cycloalkyl and $C_{3-6}$-heterocycloalkyl optionally can be substituted with 1, 2, 3, 4 or 5 substituents independently selected from the following substituents: halogen atom, hydroxy, $C_{1-6}$-alkyl, halo-$C_{1-6}$-alkyl, $C_{1-6}$-alkoxy or $C_{3-8}$-cycloalkyl;

when —B═ is —N—, $R^{3a}$ and $R^{3b}$ each independently are hydrogen atom, $C_{1-6}$-alkyl, halo-$C_{1-6}$-alkyl or $C_{3-6}$-cycloalkyl, wherein $R^{3a}$ and $R^{3b}$ can form $C_{3-6}$-cycloalkyl or $C_{3-6}$-heterocycloalkyl containing at least one O, N or S atom with the carbon to which they are attached, and the $C_{3-6}$-cycloalkyl and $C_{3-6}$-heterocycloalkyl optionally can be substituted with 1, 2, 3, 4, 5 or 6 substituents independently selected from the following substituents: halogen atom, hydroxy, $C_{1-6}$-alkyl, halo-$C_{1-6}$-alkyl, $C_{1-6}$-alkoxy or $C_{3-8}$-cycloalkyl;

X is aryl or heterocyclyl, and the X optionally can be substituted with 1, 2, 3, 4 or 5 substituents independently selected from the following substituents: halogen atom, hydroxy, $C_{1-6}$-alkyl, halo-$C_{1-6}$-alkyl, $C_{1-6}$-alkoxy or $C_{3-8}$-cycloalkyl;

$L^3$ is —N($R^{5a}$)—C(O)—, and $R^{5a}$ is hydrogen atom or $C_{1-6}$-alkyl;

Y is $C_{3-8}$-cycloalkyl, aryl or 3-10 heterocyclyl, and the Y optionally can be substituted with 1, 2, 3, 4 or 5 substituents independently selected from the following substituents: hydroxy, halogen atom, cyano, $C_{1-6}$-alkyl, hydroxy-$C_{1-6}$-alkyl, halo-$C_{1-6}$-alkyl, $C_{1-6}$-alkoxy, $C_{1-6}$-alkoxy-$C_{1-6}$-alkyl, halo-$C_{1-6}$-alkoxy, $C_{3-8}$-cycloalkyl, $C_{1-6}$-alkyl-amino, di($C_{1-6}$-alkyl)amino, $C_{1-6}$-alkylthio, phenyl, phenyloxy, $C_{5-8}$-heterocycloalkyl, $C_{5-8}$-heterocycloalkoxy, $C_{1-6}$-alkyl-carbonyl, $C_{1-6}$-alkyl-carbamoyl, formamido, $C_{1-6}$-alkyl-amido, $C_{1-6}$-alkyl-aminosulfonyl, $C_{1-6}$-alkyl-sulfonamido, di($C_{1-6}$-alkyl)carbamoyl or di($C_{1-6}$-alkyl)aminosulfonyl.

A preferable embodiment of the compound shown by general formula (I), a pharmaceutically acceptable salt thereof and a stereoisomer thereof is:

wherein, $X^1$, $X^2$, $X^3$, $X^4$ each independently are N or C($R^1$), $X^5$ is N or C($R^2$);

$R^1$ is hydrogen atom, cyano, hydroxy, amino, trifluoromethyl, trifluoromethoxy, halogen atom, $C_{1-6}$-alkyl, $C_{1-6}$-alkoxy, $C_{3-8}$-cycloalkyl, $C_{3-8}$-cycloalkyl-$C_{1-6}$-alkyl, $C_{1-6}$-alkyl-amino, di($C_{1-6}$-alkyl)amino, $C_{1-6}$-alkyl-carbamoyl, formamido, $C_{1-6}$-alkyl-amido, $C_{1-6}$-alkyl-aminosulfonyl, $C_{1-6}$-alkyl-sulfonamido, di($C_{1-6}$-alkyl)carbamoyl or di($C_{1-6}$-alkyl)aminosulfonyl;

$R^2$ is hydrogen atom, halogen atom, trifluoromethyl, trifluoromethoxy, cyano, amino, $C_{1-6}$-alkyl, $C_{1-6}$-alkoxy, $C_{3-8}$-cycloalkyl, $C_{3-8}$-cycloalkyl-$C_{1-6}$-alkyl, $C_{2-6}$-alkenyl, $C_{5-8}$-cycloalkenyl-$C_{1-6}$-alkyl, phenyl, phenyl-$C_{1-6}$-alkyl, naphthyl, $C_{3-8}$-heterocycloalkyl, $C_{3-8}$-heterocycloalkyl-$C_{1-6}$-alkyl, $C_{1-6}$-alkyl-amino, di($C_{1-6}$-alkyl)amino, $C_{1-6}$-alkyl-carbamoyl, formamido, $C_{1-6}$-alkyl-amido, $C_{1-6}$-alkyl-aminosulfonyl, $C_{1-6}$-alkyl-sulfonamido, di($C_{1-6}$-alkyl)carbamoyl or di($C_{1-6}$-alkyl)aminosulfonyl;

-A═ and —B═ each independently are —N— or —C═, and -A═ and —B═ are not simultaneously —N—;

$L^1$ is —(C($R^{1a}R^{1b}$))$_p$—, and p is 1, 2, 3 or 4;

when -A═ is —C═, $R^{1a}$ and $R^{1b}$ each independently are hydrogen atom, halogen atom, $C_{1-6}$-alkyl, halo-$C_{1-6}$-alkyl or $C_{3-6}$-cycloalkyl, wherein $R^{1a}$ and $R^{1b}$ can form $C_{3-6}$-cycloalkyl with the carbon to which they are attached, and the $C_{3-6}$-cycloalkyl optionally can be substituted with 1, 2, 3 or 4 substituents independently selected from the following substituents: halogen atom, hydroxy, $C_{1-6}$-alkyl, halo-$C_{1-6}$-alkyl or $C_{1-6}$-alkoxy;

when -A═ is —N—, $R^{1a}$ and $R^{1b}$ each independently are hydrogen atom, $C_{1-6}$-alkyl, halo-$C_{1-6}$-alkyl or $C_{3-6}$-cycloalkyl, wherein $R^{1a}$ and $R^{1b}$ can form $C_{3-6}$-cycloalkyl with the carbon to which they are attached, and the $C_{3-6}$-cycloalkyl optionally can be substituted with 1, 2, 3 or 4 substituents independently selected from the following substituents: halogen atom, hydroxy, $C_{1-6}$-alkyl, halo-$C_{1-6}$-alkyl, $C_{1-6}$-alkoxy or halo-$C_{1-6}$-alkoxy;

W is $R^{2a}$OC(O)— or ($R^{2a}$)$_2$NC(O)—, $R^{2a}$ is hydrogen, $C_{1-6}$-alkyl or $C_{3-8}$-cycloalkyl;

$L^2$ is —(C($R^{3a}R^{3b}$))$_p$—, and p is 1, 2, 3 or 4;

when —B═ is —C═, $R^{3a}$ and $R^{3b}$ each independently are hydrogen atom, halogen atom, $C_{1-6}$-alkyl or $C_{3-6}$-cycloalkyl;

when —B═ is —N—, $R^{3a}$ and $R^{3b}$ each independently are hydrogen atom, $C_{1-6}$-alkyl or $C_{3-6}$-cycloalkyl;

X is 6-10 membered aryl or 5-6 membered heterocyclyl, and the X optionally can be substituted with 1, 2, 3 or 4 substituents independently selected from the following substituents: halogen atom, hydroxy, $C_{1-6}$-alkyl or halo-$C_{1-6}$-alkyl;

$L^3$ is —N($R^{5a}$)—C(O)—, $R^{5a}$ is hydrogen atom or $C_{1-6}$-alkyl;

Y is $C_{3-8}$-cycloalkyl, 6-10 membered aryl or 5-10 membered heterocyclyl, and the Y optionally can be substituted with 1, 2, 3 or 4 substituents independently selected from the following substituents: cyano, hydroxy, halogen atom, $C_{1-6}$-alkyl, hydroxy-$C_{1-6}$-alkyl, halo-$C_{1-6}$-alkyl, $C_{1-6}$-alkoxy, $C_{1-6}$-alkoxy-$C_{1-6}$-alkyl, $C_{3-8}$-cycloalkyl, $C_{1-6}$-alkyl-amino, di($C_{1-6}$-alkyl)amino, $C_{1-6}$-alkylthio, $C_{5-8}$-heterocycloalkyl, $C_{5-8}$-heterocycloalkoxy, $C_{1-6}$-alkyl-carbamoyl, formamido, $C_{1-6}$-alkyl-amido, $C_{1-6}$-alkyl-aminosulfonyl, $C_{1-6}$-alkyl-sulfonamido, di($C_{1-6}$-alkyl)carbamoyl or di($C_{1-6}$-alkyl)aminosulfonyl.

A preferable embodiment of the compound shown by general formula (I), a pharmaceutically acceptable salt thereof and a stereoisomer thereof is:

wherein, $X^1$, $X^2$, $X^3$, $X^4$ each independently are N or C($R^1$), and $X^5$ is N or C($R^2$);

$R^1$ is hydrogen atom, halogen atom, trifluoromethyl, cyano, amino, $C_{1-6}$-alkyl, $C_{1-6}$-alkoxy, $C_{3-8}$-cycloalkyl, $C_{1-6}$-alkyl-amino, di($C_{1-6}$-alkyl)amino, $C_{1-6}$-alkyl-carbamoyl, formamido, $C_{1-6}$-alkyl-amido, di($C_{1-6}$-alkyl)carbamoyl or di($C_{1-6}$-alkyl)aminosulfonyl;

$R^2$ is hydrogen atom, halogen atom, trifluoromethyl, cyano, amino, $C_{1-6}$-alkyl, $C_{1-6}$-alkoxy, $C_{3-8}$-cycloalkyl, $C_{3-8}$-cycloalkyl-$C_{1-6}$-alkyl, $C_{2-6}$-alkenyl, $C_{5-8}$-cycloalkenyl-$C_{1-6}$-alkyl, phenyl, $C_{1-6}$-alkyl-amino or di($C_{1-6}$-alkyl)amino;

-A═ and —B═ each independently are —N— or —C═, and -A═ and —B═ are not simultaneously —N—;

$L^1$ is —(C($R^{1a}R^{1b}$))$_p$—, and p is 1, 2 or 3;

when -A═ is —C═, $R^{1a}$ and $R^{1b}$ each independently are hydrogen atom, halogen atom, $C_{1-6}$-alkyl, halo-$C_{1-6}$-alkyl or $C_{3-6}$-cycloalkyl;

when -A═ is —N—, $R^{1a}$ and $R^{1b}$ each independently are hydrogen atom, $C_{1-6}$-alkyl, halo-$C_{1-6}$-alkyl or $C_{3-6}$-cycloalkyl;

W is $R^{2a}$OC(O)—, and $R^{2a}$ is hydrogen or $C_{1-4}$-alkyl;

$L^2$ is —(C($R^{3a}R^{3b}$))$_p$—, and p is 1, 2 or 3, when —B═ is —C═, $R^{3a}$ and $R^{3b}$ each independently are hydrogen atom, halogen atom or $C_{1-4}$-alkyl;

when —B═ is —N—, $R^{3a}$ and $R^{3b}$ each independently are hydrogen atom or $C_{1-4}$-alkyl;

X is 6-10 membered aryl or 5-6 membered heterocyclyl, and the X optionally can be substituted with 1, 2 or 3 substituents independently selected from the following substituents: halogen atom, $C_{1-4}$-alkyl or halo-$C_{1-4}$-alkyl;

$L^3$ is —N($R^{5a}$)—C(O)— and $R^{5a}$ is hydrogen atom or $C_{1-4}$-alkyl;

Y is 6-10 membered aryl or 5-10 membered heterocyclyl, and the Y optionally can be substituted with 1, 2 or 3 substituents independently selected from the following substituents: halogen atom, cyano, $C_{1-6}$-alkyl, hydroxy-$C_{1-6}$-alkyl, halo-$C_{1-6}$-alkyl, $C_{1-6}$-alkoxy, $C_{1-6}$-alkoxy-$C_{1-6}$-alkyl, $C_{3-8}$-cycloalkyl, $C_{1-6}$-alkyl-amino or di($C_{1-6}$-alkyl)amino.

A preferable embodiment of the compound shown by general formula (I), a pharmaceutically acceptable salt thereof and a stereoisomer thereof is:

wherein, $X^1$, $X^2$, $X^3$, $X^4$ each independently are N or $C(R^1)$, and $X^5$ is N or $C(R^2)$;

$R^1$ is hydrogen atom, halogen atom, trifluoromethyl, cyano, amino, $C_{1-4}$-alkyl, $C_{1-4}$-alkoxy, $C_{1-4}$-alkyl-amino, formamido, $C_{1-4}$-alkyl-amido or $C_{3-6}$-cycloalkyl;

$R^2$ is hydrogen atom, halogen atom, trifluoromethyl, cyano, amino, $C_{1-4}$-alkyl, $C_{1-4}$-alkoxy, $C_{3-6}$-cycloalkyl or phenyl;

-A== and —B== each independently are —N— or —C=, and -A== and —B== are not simultaneously —N—;

$L^1$ is —$(C(R^{1a}R^{1b}))_p$—, and p is 1 or 2, when -A== is —C=, $R^{1a}$ and $R^{1b}$ each independently are hydrogen atom, halogen atom or $C_{1-4}$-alkyl;

when -A== is —N—, $R^{1a}$ and $R^{1b}$ each independently are hydrogen atom or $C_{1-4}$-alkyl;

W is —C(O)OH;

$L^2$ is —$(C(R^{3a}R^{3b}))_p$—, and p is 1 or 2, $R^{3a}$ and $R^{3b}$ each independently are hydrogen atom or $C_{1-4}$-alkyl;

X is phenyl, pyridyl or pyrazinyl, and the X optionally can be substituted with 1 or 2 substituents independently selected from the following substituents: halogen atom, $C_{1-4}$-alkyl or halo-$C_{1-4}$-alkyl;

$L^3$ is —$N(R^{5a})$—C(O)—, and $R^{5a}$ is hydrogen atom or $C_{1-4}$-alkyl;

Y is 6-10 membered aryl or 5-10 membered heterocyclyl, and the Y optionally can be substituted with 1, 2 or 3 substituents independently selected from the following substituents: halogen atom, cyano, $C_{1-4}$-alkyl or halo-$C_{1-4}$-alkyl.

A preferable embodiment of the compound shown by general formula (I), a pharmaceutically acceptable salt thereof and a stereoisomer thereof is:

wherein, $X^1$, $X^2$, $X^3$, $X^4$ each independently are N or $C(R^1)$, and $X^5$ is N or $C(R^2)$;

$R^1$ is hydrogen atom, fluorine atom, chlorine atom, trifluoromethyl, cyano, amino, $C_{1-4}$-alkyl, $C_{1-4}$-alkoxy, methylamino, formamido, acetamido or $C_{3-6}$-cycloalkyl;

$R^2$ is hydrogen atom, fluorine atom, chlorine atom, trifluoromethyl, cyano, amino, $C_{1-4}$-alkyl, $C_{1-4}$-alkoxy, $C_{3-6}$-cycloalkyl or phenyl;

-A== and —B== each independently are —N— or —C=, and -A== and —B== are not simultaneously —N—;

$L^1$ is —$(C(R^{1a}R^{1b}))_p$—, and p is 1 or 2, and $R^{1a}$ and $R^{1b}$ each independently are hydrogen atom;

W is —C(O)OH;

$L^2$ is —CH$_2$—;

X is phenyl, pyridyl or pyrazinyl, and the X optionally can be substituted with 1 or 2 substituents independently selected from the following substituents: fluorine atom, chlorine atom, methyl, ethyl, isopropyl or trifluoromethyl;

$L^3$ is —$N(R^{5a})$—C(O)—, and $R^{5a}$ is hydrogen atom or methyl;

Y is phenyl, pyridyl, pyrazolyl, naphthyl or 2,3-dihydrobenzo[b][1,4]dioxane, and the Y optionally can be substituted with 1, 2 or 3 substituents independently selected from the following substituents: fluorine atom, chlorine atom, bromine atom, cyano, methyl, ethyl, isopropyl, tert-butyl or trifluoromethyl.

A preferable embodiment of the compound shown by general formula (I), a pharmaceutically acceptable salt thereof and a stereoisomer thereof is:

wherein, $X^1$, $X^2$, $X^3$, $X^4$ each independently are N or $C(R^1)$, and $X^5$ is N or $C(R^2)$;

$R^1$ is hydrogen atom, fluorine atom, chlorine atom or $C_{1-4}$-alkyl;

$R^2$ is hydrogen atom, $C_{1-4}$-alkyl or $C_{3-6}$-cycloalkyl;

-A== and —B== each independently are —N— or —C=, and -A== and —B== are not simultaneously —N—;

$L^1$ is —CH$_2$—;

W is —C(O)OH;

$L^2$ is —CH$_2$—;

X is phenyl, pyridyl or pyrazinyl, and the X optionally can be substituted with 1 or 2 substituents independently selected from the following substituents: fluorine atom, chlorine atom, methyl, ethyl or trifluoromethyl;

$L^3$ is —$N(R^{5a})$—C(O)—, and $R^{5a}$ is hydrogen atom or methyl;

Y is phenyl, pyridyl, pyrazolyl, naphthyl or 2,3-dihydrobenzo[b][1,4]dioxane, and the Y optionally can be substituted with 1, 2 or 3 substituents independently selected from the following substituents: fluorine atom, chlorine atom, bromine atom, cyano, methyl, ethyl, isopropyl, tert-butyl or trifluoromethyl.

A preferable embodiment of the compound shown by general formula (I), a pharmaceutically acceptable salt thereof and a stereoisomer thereof is:

wherein, $X^1$, $X^2$, $X^3$ each independently are $C(R^1)$, and $X^4$ is N or $C(R^1)$, and $X^5$ is N or $C(R^2)$;

$R^1$ is hydrogen atom or fluorine atom;

$R^2$ is hydrogen atom or $C_{1-4}$-alkyl;

-A== and —B== each independently are —N— or —C=, and -A== and —B== are not simultaneously —N—;

$L^1$ is —CH$_2$—;

W is —C(O)OH;

$L^2$ is —CH$_2$—;

X is phenyl, pyridyl or pyrazinyl;

$L^3$ is —$N(R^{5a})$—C(O)—, and $R^{5a}$ is hydrogen atom or methyl;

Y is phenyl, pyridyl, pyrazolyl, naphthyl or 2,3-dihydrobenzo[b][1,4]dioxane, and the Y optionally can be substituted with 1 or 2 substituents independently selected from the following substituents: fluorine atom, chlorine atom, bromine atom, cyano, methyl, ethyl, isopropyl, tert-butyl or trifluoromethyl.

A compound shown by general formula (I), a pharmaceutically acceptable salt thereof and a stereoisomer thereof, wherein some preferable compounds are as follows:

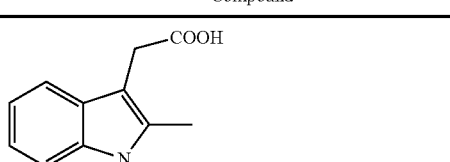

-continued
| No. | Compound |
|---|---|
| 9 | 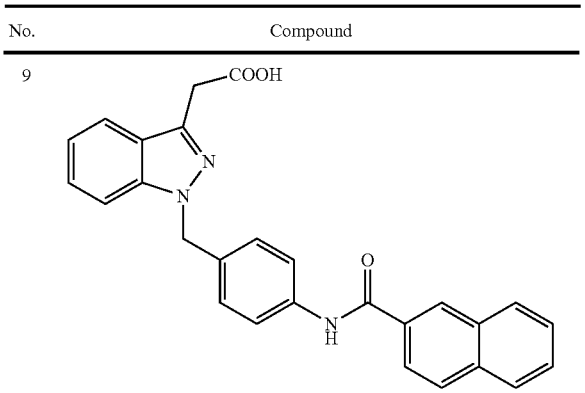 |
| 10 | 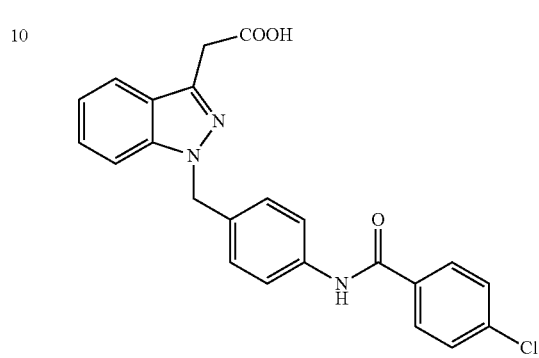 |
| 11 | 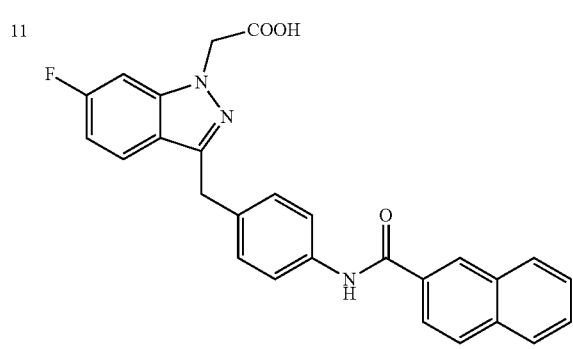 |
| 12 | 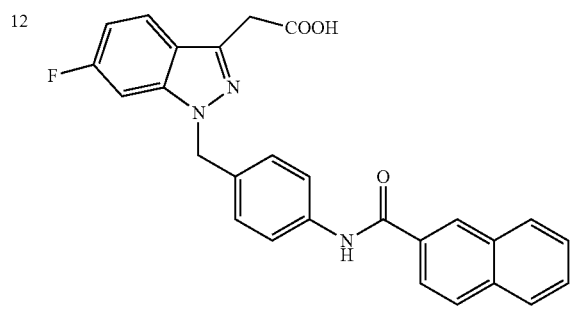 |
-continued
| No. | Compound |
|---|---|
| 13 | 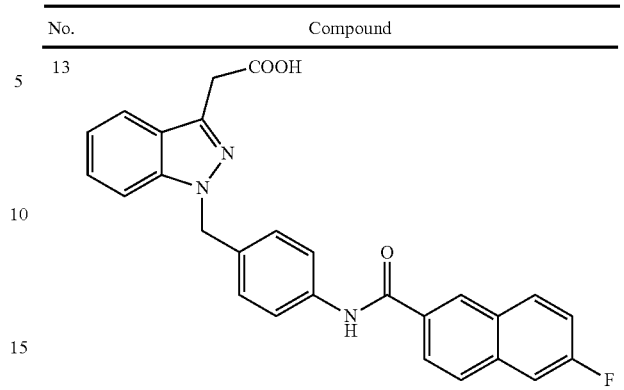 |
| 14 | 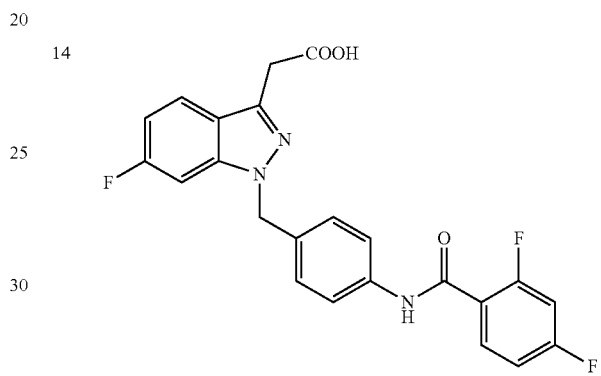 |
| 15 | 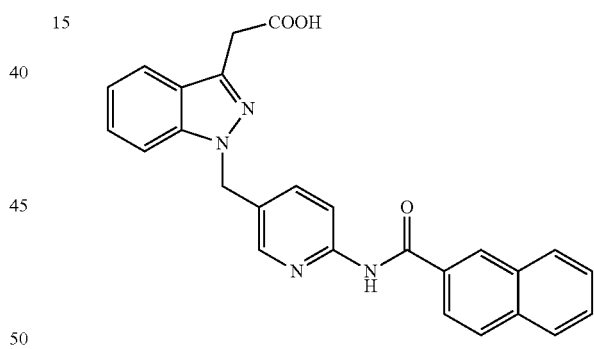 |
| 16 | 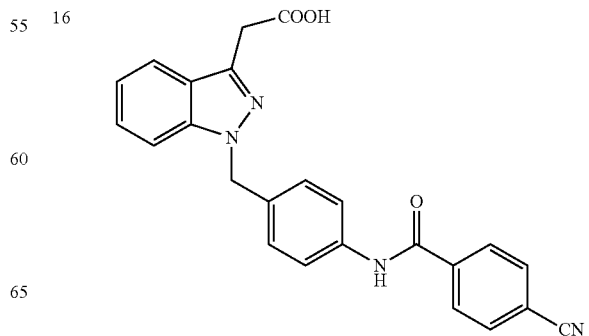 |

-continued

| No. | Compound |
|---|---|
| 17 | 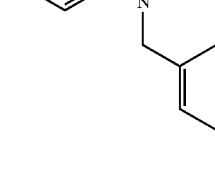 |
| 18 |  |
| 19 | 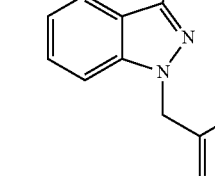 |
| 20 |  |

-continued

| No. | Compound |
|---|---|
| 21 | 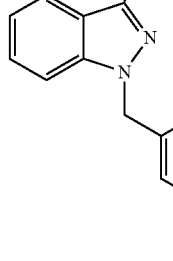 |
| 22 | 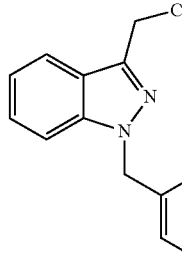 |
| 23 | 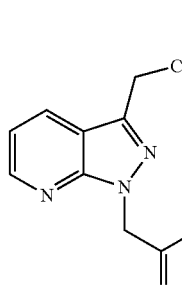 |

In the present application, the term "halogen atom" refers to fluorine atom, chlorine atom, bromine atom or iodine atom.

In the present application, the term "$C_{1-6}$-alkyl" refers to a linear or branched alkyl containing 1-6 carbon atoms, including, e.g., "$C_{1-4}$-alkyl", "$C_{1-3}$-alkyl", "$C_{2-4}$-alkyl", "$C_{2-5}$-alkyl", and the like, examples thereof including but not limited to, e.g., methyl, ethyl, n-propyl, isopropyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like. The "$C_{1-4}$-alkyl" described herein refers to specific examples which contain 1-4 carbon atoms in the above examples.

In the present application, the term "$C_{2-6}$-alkenyl" refers to a linear or branched alkenyl containing a double bond and having 2-6 carbon atoms, including, e.g., "$C_{2-4}$-alkenyl", "$C_{2-5}$-alkenyl", "$C_{2-3}$-alkenyl" and the like; examples thereof including but not limited to, e.g., ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadiene, 1,3-pentadiene, 1,4-pentadiene, 1,4-hexadiene, and the like.

In the present application, the term "$C_{5-8}$-cycloalkenyl" refers to a cyclic group containing a double bond and having 5-8 carbon atoms, including, e.g., "$C_{5-6}$-cycloalkenyl", "$C_{5-7}$-cycloalkenyl", and the like; examples thereof including but not limited to, e.g., cyclopentenyl, 1,3-cyclopentadienyl, cyclohexenyl, 1,3-cyclohexadienyl, 1,4-cycloheptadienyl, cycloheptenyl, 1,3-cycloheptadienyl, 1,3,5-cycloheptatrienyl, cyclooctenyl, 1,3,5-cyclooctatrienyl, and the like.

In the present application, the term "$C_{2-6}$-alkynyl" refers to a linear or branched alkynyl containing a triple bond and having 2-6 carbon atoms, including, e.g., "$C_{2-5}$-alkynyl", "$C_{2-4}$-alkynyl", "$C_{2-3}$-alkynyl", and the like, examples thereof including but not limited to, e.g., ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, 1-ethyl-1-methyl-2-propynyl, and the like.

In the present application, the term "$C_{1-6}$-alkoxy" refers to a group connected in a manner of "$C_{1-6}$-alkyl-O—", wherein "$C_{1-6}$-alkyl" is as defined above; including, e.g., "$C_{1-4}$-alkoxy", "$C_{1-3}$-alkoxy", "$C_{2-4}$-alkoxy", "$C_{2-5}$-alkoxy", and the like.

In the present application, the term "$C_{1-6}$-alkylthio" refers to a group connected in a manner of "$C_{1-6}$-alkyl-S-", wherein "$C_{1-6}$-alkyl" is as defined above; including, e.g., "$C_{1-4}$-alkylthio", "$C_{1-3}$-alkylthio", "$C_{2-4}$-alkylthio", "$C_{2-5}$-alkylthio", and the like.

In the present application, the term "$C_{3-8}$-cycloalkyl" refers to a cycloalkyl containing 3-8 carbon atoms, including, e.g., "$C_{3-6}$-cycloalkyl", "$C_{4-6}$-cycloalkyl", "$C_{5-6}$-cycloalkyl", and the like, examples thereof including but not limited to, e.g., cyclopropyl, cyclobutyl, cyclopentyl, cyclohexyl, cycloheptyl, cyclooctyl, and the like.

In the present application, the term "halo-$C_{1-6}$-alkyl", "halo-$C_{1-6}$-alkoxy" refers to a group derived by substituting the "$C_{1-6}$-alkyl", "$C_{1-6}$-alkoxy" defined above with one to more "halogen atoms", preferably chloro or fluoro.

In the present application, the term "$C_{3-8}$-heterocycloalkyl" refers to a group derived by replacing one to more carbon atoms in a $C_{3-8}$-cycloalkyl with S, O, N or C(O), wherein the "$C_{3-8}$-cycloalkyl" is as described above.

In the present application, the term "aryl" refers to a 6-14 membered cyclic aromatic group with all ring atoms being carbon atoms, including 6-8 membered monocyclic aryl and 8-14 membered condensed aryl. The 6-8 membered monocyclic aryl refers to a completely unsaturated aryl, such as phenyl, cyclooctatetraenyl, and the like. The 8-14 membered condensed aryl refers to a condensed ring group formed by two or more cyclic structures sharing two adjacent carbon atoms with each other, wherein at least one ring is an unsaturated aromatic ring, including 8-14 membered unsaturated condensed aryl, such as naphthyl, phenanthryl, and the like, further including 8-14 membered partially saturated condensed aryl, such as, benzo $C_{3-8}$-cycloalkyl, benzo $C_{4-8}$-cycloalkenyl, specific examples such as 2,3-dihydro-1H-indenyl, 1H-indenyl, 1,2,3,4-tetrahydronaphthyl, 1,4-dihydronaphthyl, and the like. The "6-10 membered aryl" refers to a 6-10 membered cyclic aromatic group with all ring atoms being carbon atoms, including monocyclic aryl, further including condensed aryl, wherein the condensed aryl can be unsaturated, or can be partially saturated.

In the present application, the term "heterocyclyl" refers to a cyclic group containing 3-14 ring atoms (wherein containing at least one heteroatom), including, e.g., "3-10 membered heterocyclyl", "5-10 membered heterocyclyl", "5-6 membered heterocyclyl", "5-8 membered heterocyclyl", "6-10 membered heterocyclyl", "9-10 membered heterocyclyl", and the like, wherein the heteroatom includes nitrogen, oxygen and sulfur, and the like, and the carbon atom, the nitrogen atom, and the sulfur atom can also be substituted with oxo. Examples thereof include but are not limited to, e.g., furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridone, 4-pyridone, pyrimidinyl, 1,4-dioxacyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,3,4-triazinyl, 1,2,4,5-tetrazinyl, oxacycloheptatrienyl, thiacycloheptatrienyl, azacycloheptatrienyl, 1,3-diazacycloheptatrienyl, azacyclooctatetraenyl, 1,4-dihydro-1,4-diazacyclooctatrienyl, 1,4-dioxacyclooctatrienyl, and the like, benzofuryl, benzoisofuryl, benzothienyl, indolyl, isoindolyl, benzooxazolyl, benzoimidazolyl, indazolyl, benzotriazolyl, quinolyl, 2-quinolinone, 4-quinolinone, 1-isoquinolinone, isoquinolyl, acridinyl, phenanthridinyl, benzopyridazinyl, phthalazinyl, quinazolinyl, quinoxalinyl, phenoxazinyl, pteridyl, purinyl, naphthyridinyl, phenazine, phenothiazine, 2,3-dihydrobenzo[b][1,4]dioxane, and the like.

The present application seeks to protect a method for preparing the compound of formula (I), and the compound of formula (I) can be synthesized by the method described in the following processes and/or other technologies known to one of ordinary skill in the art, but not only limited to the following processes.

Process 1:

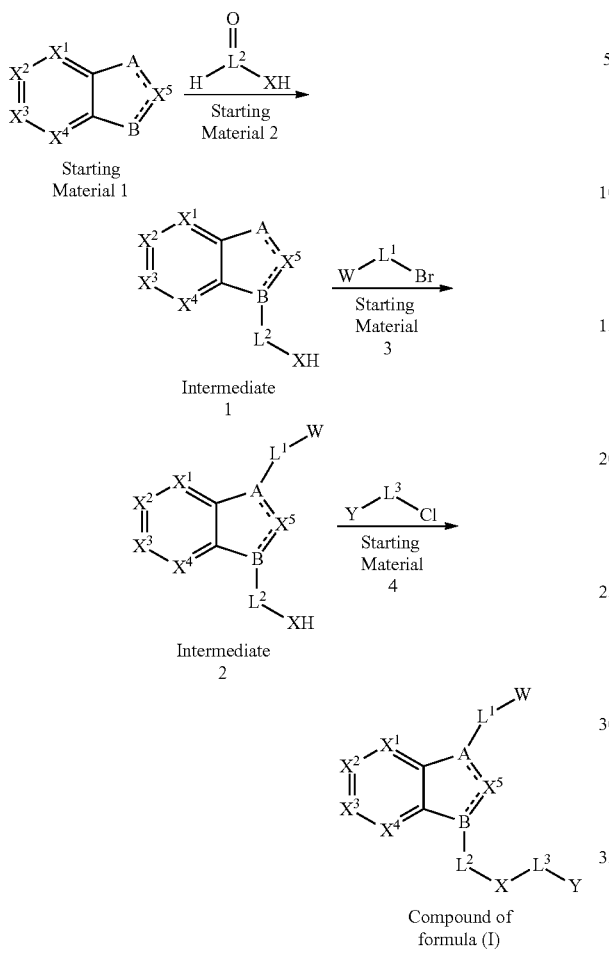

Process 2:

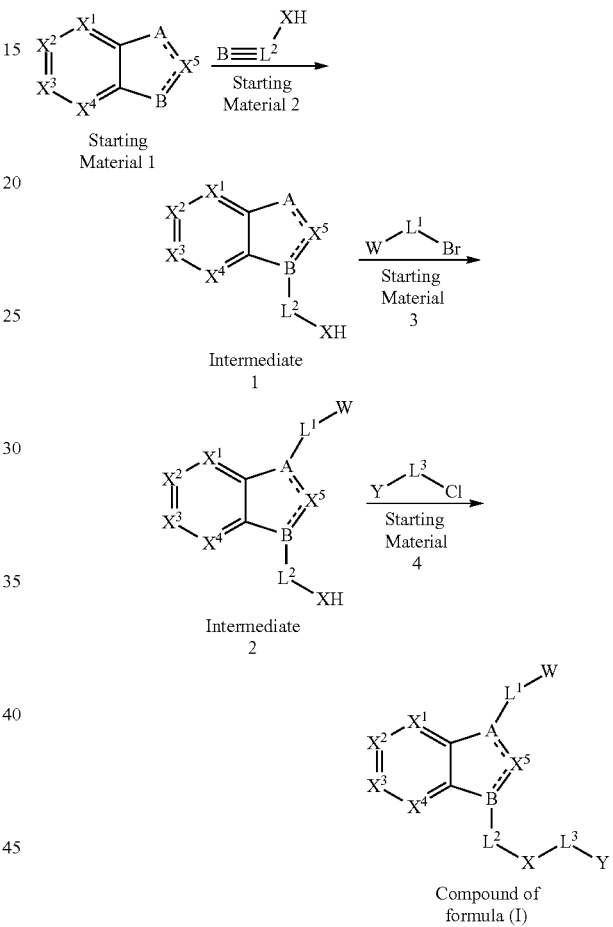

(1) Preparation of Intermediate 1:

At low temperature (such as −15-5° C.), 1.5 equivalents of trifluoroacetic acid, 3.0 equivalents of triethylsilane were added into a reaction vessel and dissolved in dichloromethane. After stirring and reacting, a dichloromethane solution dissolving 1 dropwise slowly into the reaction vessel. After completion of dropwise addition, the reaction was maintained at low temperature (such as −15-5° C.). The pH was adjusted to be basic with a sodium hydroxide solution. An aqueous solution of sodium chloride was added, and extracted with dichloromethane. The extract was dried over anhydrous sodium sulfate, concentrated to dryness to obtain a solid, and washed with diethyl ether to obtain intermediate 1.

(2) Preparation of Intermediate 2:

1 Equivalent of intermediate 1 was weighed, and dissolved in DMF. 2 Equivalents of base (such as cesium carbonate, potassium carbonate, and the like) was added, stirred and reacted at a temperature of 5-30° C. 1.1 equivalents of starting material 3 was added, reacted for several hours. Upon completion of the reaction, it was filtered, and the filtrate was added into water, and extracted with ethyl acetate. The extract was washed with water and a saturated solution of sodium chloride, rotate evaporated to dryness, and chromatographed on a silica gel column to obtain intermediate 2.

(3) Preparation of the Compound of Formula (I):

In a dry reaction vessel, 1 equivalent of intermediate 2 was added and dissolved in dichloromethane. 3 Equivalents of triethylamine was added, and a dichloromethane solution dissolving 1.1 equivalents of starting material 4 was added slowly at low temperature (such as −15-5° C.). After completion of dropwise addition, it was reacted at low temperature (such as −15-5° C.) for 1 h, and stirred at room temperature overnight. It was filtered, an aqueous solution of sodium bicarbonate was added, extracted with dichloromethane, rotate evaporated to dryness, chromatographed on a column to obtain the compound of formula (I).

(1) Preparation of Intermediate 1:

Into a dry reaction vessel, added respectively were 1 equivalent of starting material 1, 1.3 equivalents of starting material 2, with toluene and triethylamine as the solvent, catalyst $(Ph_3P)_2PdCl_2$ and cuprous iodide. It was heated and reacted under protection of nitrogen for several hours. It was cooled, rotate evaporated to dryness to remove the solvent, and chromatographed on a column to obtain intermediate 1.

(2) Preparation of Intermediate 2:

1 Equivalent of intermediate 1 was weighed, and dissolved in DMF. 2 Equivalents of a base (such as cesium carbonate, potassium carbonate, and the like) was added, stirred and reacted at a temperature of 5-30° C. 1.1 Equivalents of starting material 3 was added, and reacted for several hours. Upon completion of the reaction, it was filtered. The filtrate was added into water, and extracted with ethyl acetate. The extract was washed with water and a saturated solution of sodium chloride, rotate evaporated to dryness, chromatographed on a silica gel column to obtain intermediate 2.

(3) Preparation of the Compound of Formula (I):

In a dry reaction vessel, 1 equivalent of intermediate 2 was added and dissolved in dichloromethane. 3 Equivalents of triethylamine was added, at low temperature (such as −15-5° C.) a dichloromethane solution dissolving 1.1 equivalents of starting material 4 was added slowly. After completion of dropwise addition, it was reacted at low temperature (such as −15-5° C.) for 1 h, stirred overnight at a temperature of 5-30° C. It was filtered, an aqueous solution of sodium bicarbonate was added, extracted with dichloromethane, rotate evaporated to dryness, chromatographed on a column to obtain the compound of formula (I).

Process 3:

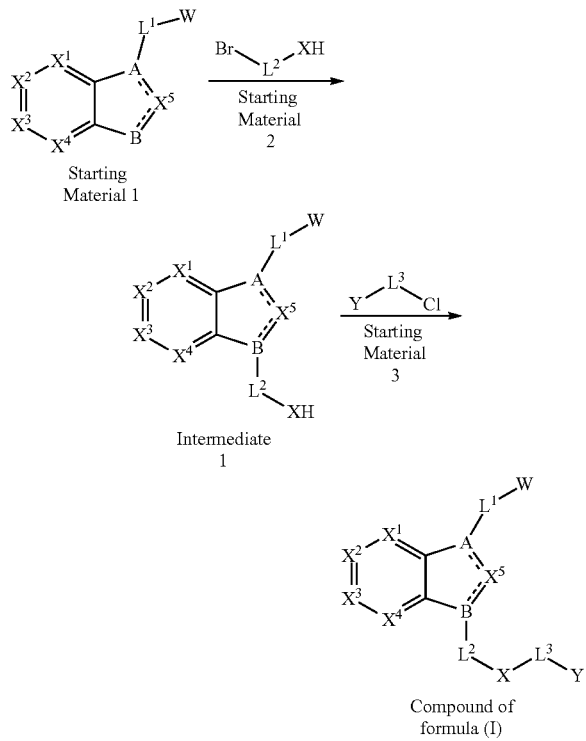

(1) Preparation of Intermediate 1:

1 Equivalent of starting material 1, and 1 equivalent of starting material 2 were added into toluene. 1.2 Equivalents of a base (such as cesium carbonate, and the like), and a catalytic amount of phase transfer catalyst (such as cetyl tributyl phosphonium bromide, and the like) were added. Upon completion of addition, it was heated and reacted for several hours. Upon completion of the reaction, it was cooled. Water was added, and extracted with diethyl ether. The extract was washed with water, rotate evaporated to dryness to remove the organic phase, purified by preparative liquid phase to obtain intermediate 1.

(2) Preparation of the Compound of Formula (I):

In a dry reaction vessel, 1 equivalent of intermediate 1 was added and dissolved in dichloromethane. 3 Equivalents of triethylamine was added. A dichloromethane solution dissolving 1.1 equivalents of starting material 3 was added slowly at low temperature (such as −15-5° C.). After completion of dropwise addition, it was reacted at low temperature (such as −15-5° C.) for 1 h, and stirred overnight at a temperature of 5-30° C. It was filtered. An aqueous solution of sodium bicarbonate was added, extracted with dichloromethane, rotate evaporated to dryness, chromatographed on a column to obtain the compound of formula (I).

$X^1$, $X^2$, $X^3$, $X^4$, $X^5$, W, X, Y, $L^1$, $L^2$, $L^3$, A, B in the above reaction equations are as defined above. When necessary, functional groups need to be protected can be protected, and the protecting groups are removed by conventional methods; when necessary, according to the properties of the compounds, the solvents for reactions can be replaced appropriately; when necessary, according to the properties of the compounds, preparations of some compounds can be omitted or added.

A pharmaceutically acceptable salt of any one of the above compounds of the present application includes alkali metal salts, such as sodium salt, potassium salt, lithium salt, and the like; alkaline-earth metal salts, such as calcium salt, magnesium salt, and the like; other metal salts, such as aluminium salt, iron salt, zinc salt, copper salt, nickel salt, cobalt salt, and the like; inorganic base salts, such as ammonium salt; organic base salts, such as tert-octyl amine salt, dibenzylamine salt, morpholine salt, glucosamine salt, phenyl glycine-alkyl ester salt, ethylenediamine salt, N-methylglucosamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenylethylamine salt, piperazine salt, tetramethylamine salt, tri(hydroxymethyl)aminomethane salt; when the compound of the present application is basic, a salt can be prepared from pharmaceutically acceptable non-toxic acids including inorganic acids and organic acids, such acid salts include: halogen acid salt, such as hydrofluoric acid salt, hydrochloric acid salt, hydrobromic acid salt, hydroiodic acid salt, and the like; inorganic acids salt, such as nitrate, perchlorate, sulfate, phosphate, and the like; lower alkyl sulfonates, such as methanesulfonate, trifluoromethanesulfonate, ethanesulfonate, and the like; arylsulfonates, such as benzenesulfonate, p-benzenesulfonate, and the like; organic acid salts, such as acetate, malate, fumarate, succinate, citrate, tartrate, oxalate, maleate, and the like; amino acid salts, such as glycine salt, trimethylglycine salt, arginine salt, ornithine salt, glutamine, aspartic acid salt, and the like. In order to avoid doubt, there might be one, two, or three salt-forming cations, but this depends on the number of carboxy functional groups and the valences of the cations. It is apparent to one of skills in the art that the pharmaceutically acceptable salt of the compound of the present application can be formed at the free carboxy and the like of the compound, and can be prepared by conventional methods.

The present application further includes a stereoisomer of the compound of formula (I) or a pharmaceutically acceptable salt thereof. The compound of formula (I) of the present application or a pharmaceutically acceptable salt thereof can be present in the form of an optical isomer due to the presence of a chiral molecule. Thus, the present application also includes these optical isomers and mixtures thereof. When the compound of formula (I) of the present application or a pharmaceutically acceptable salt thereof contains a double bond or a small cyclic structure, due to the hindrance of the free rotation of the bond between the atoms of the double bond or the cycle in the molecule, there are different spatial arrangements, resulting in stereoisomers, which are also called as cis-trans isomers. The present application also includes these cis-trans isomers and mixtures thereof. The present application also includes stereoisomers generated by changing the positions of spatial arrangement of atoms or atomic groups attached to carbon due to the rotation of a single bond, which are also called as conformational isomerism, and also includes mixtures thereof.

The compound of formula (I) of the present application, a pharmaceutically acceptable salt thereof or a stereoisomer thereof, can be formulated with one or more pharmaceutically acceptable carriers into a pharmaceutically acceptable pharmaceutical formulation, which is administered to a patient in need of such a treatment in a manner of orally, parenterally, and the like. When administered orally, a conventional solid formulation, such as tablets, capsules, pills, granules, and the like, can be prepared with conventional fillers, binding agents, disintegrants, lubricants, diluents, and the like; when administered parenterally, can be formulated in to an injection formulation, including injection solution, sterile powder for injection and concentrated solution for injection. When formulated into an injection formulation, it can be produced by using conventional methods in the field of pharmaceuticals. When formulating an injection formulation, either no additive is added, or a suitable additive can be added according to the property of the medicament. The procedures for preparing such formulations are known, or apparent to one of skills in the art: see, e.g. Remington's Pharmaceutical Sciences, Mack Publishing Co., Easton, Pa., $16^{th}$, Ed., 1980.

The present application further provides a use of the compound shown by general formula (I), a pharmaceutically acceptable salt thereof and a stereoisomer thereof for the manufacture of a medicament for the treatment and/or prevention of diseases related to activity of CRTH2 selected from asthma, allergic rhinitis, allergic dermatitis, allergic conjunctivitis, Churg-Strauss syndrome, nasal sinusitis, basophilic leukemia, chronic urticaria, basophilic leukocytosis, psoriasis, eczema, inflammatory bowel disease, ulcerative colitis, Crohn's disease, arthritis or chronic obstructive pulmonary disease.

The "treatment" described herein refers to alleviation, amelioration, elimination or abation of the signs and symptoms related to the disease or condition.

The "prevention" described herein refers to inhibition or deferment of the occurrence or development of the disease or condition, or inhibition or deferment of the signs or symptoms related to the disease or condition.

The present application further provides a pharmaceutical composition comprising the compound shown by general formula (I), a pharmaceutically acceptable salt thereof and a stereoisomer thereof and one or more therapeutically active substances selected from TNF-α inhibitors, COX-1/COX-2 inhibitors, COX-2 inhibitors, glucocorticoids, inactivated antibodies for interleukin, regulators for chemotactic factor receptor, antagonists for histamine H1 receptors/antihistamines, leukotriene antagonists, LTD4 antagonists, VLA-4 antagonists, corticosteroids, corticosteroids analogues, β2-agonists, theophylline, leukotriene biosynthetic inhibitors, phosphodiesterase type IV inhibitors, opioids analgesics, anticoagulants, β-blocking agents, β-adrenergic agonists, angiotensin converting enzyme inhibitors or HMG-CoA reductase inhibitors.

The "composition" described herein refers to any product produced by inert conjugation or polymerization of the active components and constituting carriers, or from decomposition of one or more components, or from other types of reactions or interactions of one or more components in the pharmaceutical composition. Therefore, the pharmaceutical composition of the present application includes any composition prepared by mixing the compound of formula (I) with one or more pharmaceutically acceptable excipients.

The beneficial effects of the compounds of the present application are further illustrated by pharmacological activity assays of some compounds of the present application. Other compounds of the present application have the same beneficial effects as those compounds of the present application listed in the assays. However, it should not be interpreted as the compounds of the present application only have the following beneficial effects.

TEST EXAMPLE 1

In Vitro Pharmacological Activity of the Compounds of the Present Application

Material for test Ramatroban, commercially available;
The compounds of the present application, prepared according to the procedures in the Examples.
Test procedure The test was performed by Nanjing GenScript Biotech Ltd. by calcium flux assay. Test procedure and results are as follows:

Material for test was weighed accurately, and DMSO was added to dissolve the material for test, mixed and homogenized sufficiently, and formulated to 50 mM. And then, it was diluted to 50 µM by using 20 mM HEPES (hydroxyethylpiperazine ethanesulfonic acid) buffer solution at pH 7.4, and the maximum concentration of the compound was 10000 nM. It was further diluted by 3 folds as a series, and consecutively diluted to 10 concentrations, to reserve.

FLIPR Assay (Real Time Fluorescence Imaging Analysis)
In a 384 black microwell plate, 20 µl of cell solution containing 20000 CHO-K1/CRTH2/$G_{\alpha15}$ was added, and was incubated at 37° C., 5% $CO_2$ for 18 h. Then, 20 µl of stain in the FLIPR® Calcium 4 assay kit (kit) was added, and 10 µl of compound solution was added. Then, it was incubated at 37° C. for 60 min, and was incubated at room temperature for 15 min. Within 20 seconds, PGD2 HEPES buffer solution of an agonist PGD2 (prostaglandin D2) at the concentration of $EC_{80}$ was added, and the values of fluorescence of 21-120 seconds were detected.

Data Processing

ΔRFU(Relative fluorescence intensity)=maximum fluorescence value of 21-120 seconds−average value of fluorescence value of 1-20 seconds.

Inhibition ratio={1−(ΔRFU$_{compound}$−ΔRFU$_{background}$)/(ΔRFU$_{agonists\ control}$−ΔRFU$_{background}$)}×100

$IC_{50}$ values of the compounds (i.e. the concentration of the compound for test needed for blocking 50% of the activation of CRTH2 receptor induced by $PGD_2$ at the concentration of $EC_{80}$) were calculated based on the inhibition ratios.
Test Results and Conclusions

TABLE 1

Antagonism of the compounds of the present application against CRTH2 receptor

| Material for Test | $IC_{50}$ |
|---|---|
| Ramatroban | 10.3 µM |
| Compound 1 | 2.6 nM |
| Compound 2 | 2.3 nM |
| Compound 3 | 6.2 nM |
| Compound 4 | 2.7 nM |
| Compound 5 | 2.3 nM |
| Compound 6 | 0.5 nM |
| Compound 7 | 7 nM |
| Compound 8 | 9.7 nM |
| Compound 9 | 3.6 nM |

TABLE 1-continued

Antagonism of the compounds of the present application against CRTH2 receptor

| Material for Test | IC$_{50}$ |
|---|---|
| Compound 10 | 7.3 nM |
| Compound 11 | 1.19 nM |
| Compound 12 | 14.9 nM |
| Compound 13 | 4.42 nM |
| Compound 23 | 5.7 nM |

It can be seen from the comparative results in the above table that the compounds of the present application has an antagonism against CRTH2 receptor substantially superior to Ramatroban, having substantive features and notably progress.

TEST EXAMPLE 2

In Vivo Pharmacological Activity Assay (Oral Administration)

Material for test The compounds of the present application, prepared according to the procedures in the Examples.

Test procedure The test was performed by PharmaLegacy Biological and Medical Technology (Shanghai) Ltd. to prove the therapeutical effect of the compounds toward mice asthma by using an OVA induced mice asthma model. Test procedure and results are as follows:

After acclimation, female BALB/c mice were divided into a blank control group, a model group and an administration group based on body weight randomly. Animal groups, dosage of administration and volume of administration were as detailed in Table 2. The model group and the administration group were intraperitoneally injected with OVA (ovalbumin) solution (containing 20 g OVA and 2 mg potassium aluminium sulfate) 0.1 mL/animal to allergize on days 1, 14, the blank control group was injected with PBS (phosphate buffer solution). On days 28, 29, 30, 1% OVA was atomized and inhaled continuously to activate for 30 min, for the blank control group replaced with PBS. On days 27, 28, 29, 30, 31, the animals were administered orally with the pharmaceutical and the solvent. The blank control group was administered with the solvent 2 times every day, 1 h before inhalation of PBS and 7 h after the inhalation; the model group was administered with the solvent 2 times every day, 1 h before the inhalation of OVA for activation and 7 h after activation; the administration group was administered with the pharmaceutical 2 times every day, 1 h before the inhalation of OVA for activation and 7 h after activation. On day 32, the animals were executed, immediately irrigated the lung with 0.5 mL PBS (containing 1% FBS) via bronchus, and the irrigation was repeated 2 times. The irrigating solutions were combined, centrifugated, and the cells were resuspended with 1.5 mL PBS (containing 1% FBS). Cell count of bronchus pulmonary alveoli irrigating solution.

TABLE 2

Table of administration to animals

| Group | Animals | Volume (mL/kg) | Dosage (mg/kg) | Number of Administration |
|---|---|---|---|---|
| Blank Control | 8 | 10 | Solvent | bid |
| Model | 8 | 10 | Solvent | bid |
| Compound 9 | 8 | 10 | 30 | bid |

TABLE 3

Influences of oral administration to total cell count and classification of pulmonary alveoli irrigating solution in OVA induced BALB/c mice asthma model (*10$^4$/mL)(Mean ± SEM)

| Group | Total White Cell Count | Acidophilic Cell | Macrophages | Lymphocytes | Neutrophilic Granulocyte |
|---|---|---|---|---|---|
| Blank Control | 27.84 ± 3.75 | 0.98 ± 0.55 | 26.38 ± 3.85 | 0.16 ± 0.02 | 0.33 ± 0.1 |
| Model | 204.47 ± 19.38## | 109.28 ± 15.03## | 75.48 ± 8.65## | 1.13 ± 0.13# | 18.58 ± 4.29## |
| Compound 9 | 98.63 ± 4.53 | 35.26 ± 4.53 | 55.38 ± 5.1** | 1.33 ± 0.23 | 6.66 ± 1.87* | p < 0.05,
p < 0.01, the model group compared with the blank control group;
*p < 0.05,
**p < 0.01, the test group compared with the model group.

SPECIFIC EMBODIMENTS

The above content of the present application is further illustrated in detail by the specific embodiments as examples below. However, it should not be interpreted as that the scope of the above subjects of the present application is only limited to the examples below.

Example 1

Preparation of 2-[1-[4-(2-naphthamido)benzyl]-2-methyl-1H-indol-3-yl]acetic acid (Compound 1)

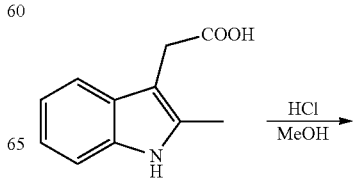

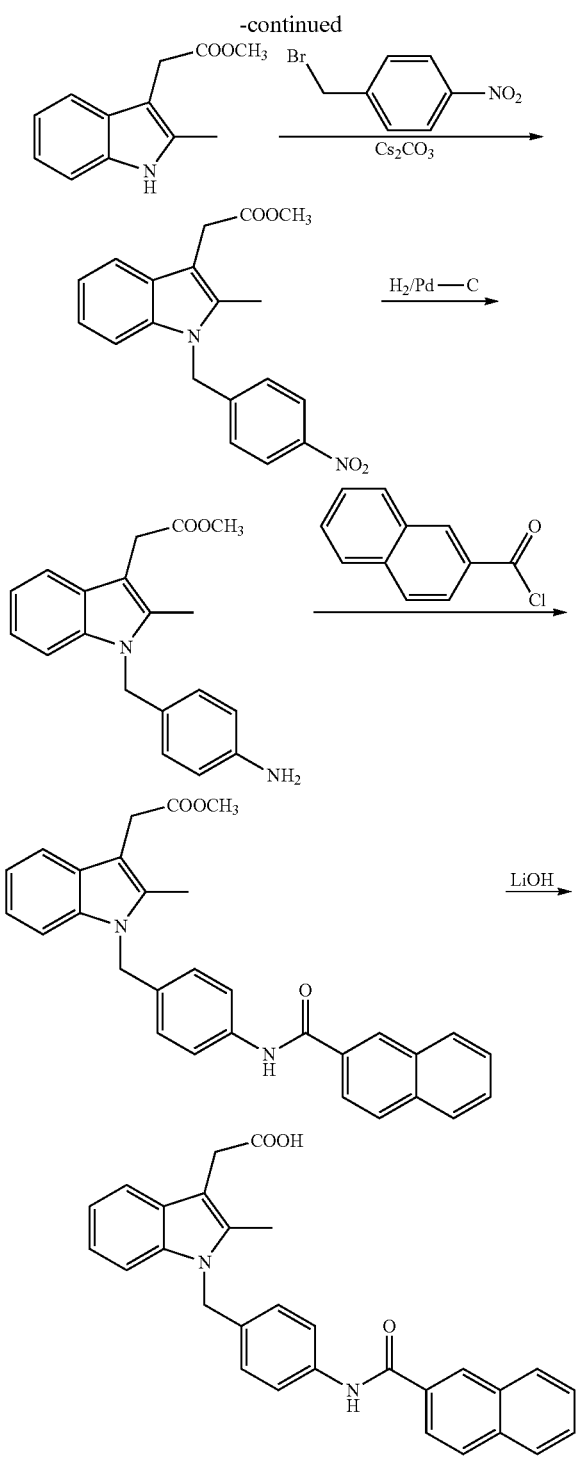

1. Preparation of methyl 2-(2-methyl-1H-indol-3-yl)acetate 2-(2-Methyl-1H-indol-3-yl)acetic acid (11.7 g, 61.84 mmol) was weighed and added into 100 mL methanol. Concentrated hydrochloric acid 0.7 mL was added dropwise. It was reacted at 70° C. for 4 hours, cooled, rotate evaporated to dryness, extracted with ethyl acetate, washed twice with NaHCO₃ aqueous solution. The organic phase was dried and rotate evaporated to dryness to obtain a red brown solid 11.4 g, at a yield of 90.7%.

2. Preparation of methyl 2-[2-methyl-1-(4-nitrobenzyl)-1H-indol-3-yl]acetate Into 100 mL toluene were added methyl 2-(2-methyl-1H-indol-3-yl)acetate (4.9 g, 24.1 mmol), p-nitro benzyl bromide (5.18 g, 24.0 mmol), cesium carbonate (9.38 g, 28.8 mmol), and cetyl tributyl phosphonium bromide (1.58 g, 3.1 mmol). Upon completion of addition, it was reacted at 110° C. for 6 hours. Upon completion of the reaction, it was cooled, water was added, and extracted with diethyl ether. The extract was washed with water. The organic phase was rotate evaporated to dryness, and purified by preparative liquid phase to obtain the product 300 mg, at a yield of 3.7%.

3. Preparation of methyl 2-[1-(4-aminobenzyl)-2-methyl-1H-indol-3-yl]acetate Into a dry reaction vessel, methyl 2-[2-methyl-1-(4-nitrobenzyl)-1H-indol-3-yl]acetate (300 mg, 0.887 mmol) was added, and dissolved in 10 mL methanol. 10% Pd/C 20 mg was added, and reacted under hydrogen for 3 hours. After completion of the reaction, it was filtered. The filter cake was washed with methanol, and the filtrate was rotate evaporated to dryness to obtain a solid 260 mg, at a yield of 95.0%.

4. Preparation of methyl 2-[1-[4-(2-naphthamido)benzyl]-2-methyl-1H-indol-3-yl]acetate Into a dry reaction vessel, methyl 2-[1-(4-aminobenzyl)-2-methyl-1H-indol-3-yl]acetate (260 mg, 0.843 mmol) was added, and dissolved in 10 mL dichloromethane. Triethylamine (0.36 mL, 2.59 mmol) was added, and 2-naphthoyl chloride (195 mg, 1.02 mmol) was added slowly in an ice bath. Upon completion of addition, it was reacted for 1 h in an ice bath, and stirred at room temperature for 3 days. An aqueous solution of sodium bicarbonate was added to quench. It was extracted with dichloromethane, rotate evaporated to dryness, chromatographed on a column to obtain a white solid 150 mg, at a yield of 38.4%.

5. Preparation of 2-[1-[4-(2-naphthamido)benzyl]-2-methyl-1H-indol-3-yl]acetic acid Into a dry reaction vessel, methyl 2-[1-[4-(2-naphthamido)benzyl]-2-methyl-1H-indol-3-yl]acetate (150 mg, 0.324 mmol), lithium hydroxide monohydrate (55 mg, 1.31 mmol), 3 mL tetrahydrofuran, 3 mL water were weighed, and stirred at room temperature for 2 h. The reaction was monitored to be complete by TLC. The solvent was rotate evaporated. It was adjusted to pH=3-4 with 2 N HCl solution. It was extracted by ethyl ester, rotate evaporated to dryness to obtain the product as a white solid 80 mg. After recrystallization by ethyl acetate, a pure product 51 mg was obtained, at a yield of 35.2%.

Mass Spectrum (M+H): 449.2

¹H-NMR (d₆-DMSO, 400 MHz): δ 10.40 (1H, s), 8.52 (1H, s), 8.08-7.94 (4H, m), 7.70 (2H, d), 7.65-7.56 (2H, m), 7.45 (1H, d), 7.38 (1H, d), 7.08-6.95 (4H, m), 5.37 (2H, s), 3.63 (2H, s), 2.32 (3H, s).

Example 2

Preparation of 2-[3-[4-(2-naphthamido)benzyl]-2-methyl-1H-indol-1-yl]acetic acid (Compound 2)

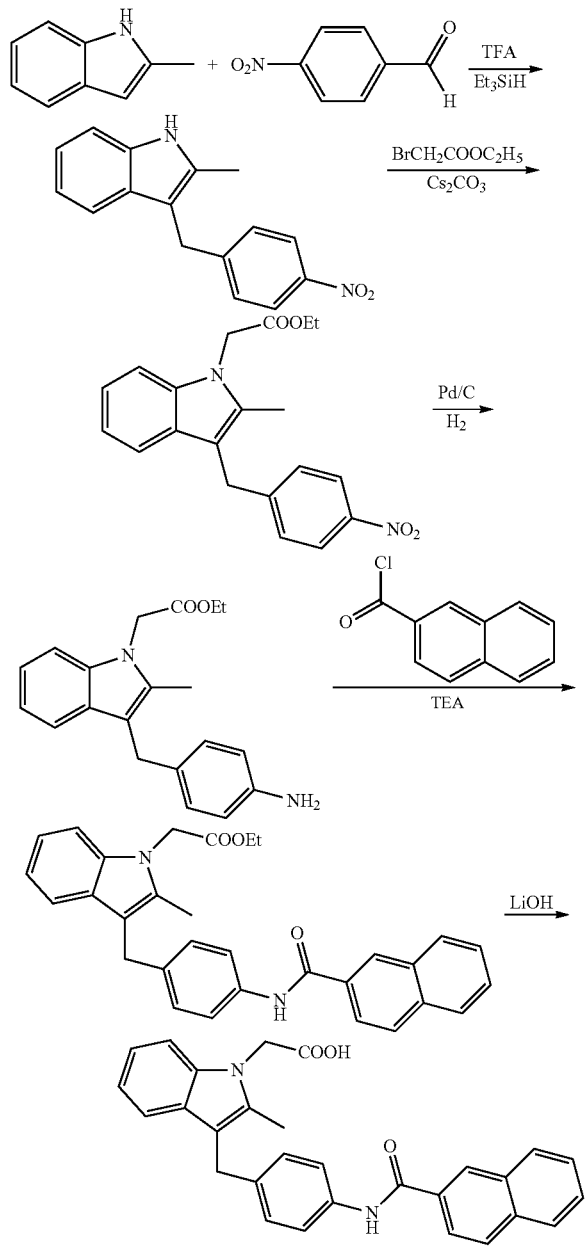

1. Preparation of 2-methyl-3-(4-nitrobenzyl)-1H-indole

In an ice water bath, into a reaction vessel were added trifluoroacetic acid (6.824 g, 60 mmol), triethylsilane (13.9 g, 120 mmol), dichloromethane 20 mL. After stirring for 5 min, a dichloromethane solution dissolving 2-methyl-1H-indole (5.24 g, 40 mmol) and p-nitro benzaldehyde (6.67 g, 44 mmol) was added dropwise slowly into the reaction vessel. After completion of dropwise addition, it was reacted maintaining this temperature for 1 h. It was adjusted to pH=8-9 with 2 M solution of sodium hydroxide. An aqueous solution of sodium chloride was added, and extracted with dichloromethane. The extract was dried over anhydrous sodium sulfate, concentrated to dryness to obtain a red brown solid, and washed with diethyl ether to obtain a yellow powdered solid 4.3 g, at a yield of 40.3%.

2. Preparation of ethyl 2-[2-methyl-3-(4-nitrobenzyl)-1H-indol-1-yl]acetate

2-Methyl-3-(4-nitrobenzyl)-1H-indole (4.0 g, 15 mmol) was weighed, and dissolved in 30 mL DMF. Cesium carbonate (9.77 g, 30 mmol) was added, and stirred at room temperature for 15 min. Ethyl bromoacetate (2.755 g, 16.5 mmol) was added, and reacted at room temperature for 3 h. Upon completion of the reaction, it was filtered. The filtrate was added into water, and extracted with ethyl acetate. The extract was washed with water, and a saturated solution of sodium chloride, rotate evaporated to dryness, chromatographed on a silica gel column (petroleum ether) to obtain a yellow solid 2.7 g, at a yield of 51.1%.

3. Preparation of ethyl 2-[3-(4-aminobenzyl)-2-methyl-1H-indol-1-yl]acetate

Into a dry reaction vessel, ethyl 2-[2-methyl-3-(4-nitrobenzyl)-1H-indol-1-yl]acetate (2.7 g, 7.66 mmol) was added, and dissolved in 30 mL methanol. 10% Pd/C 300 mg was added, purged with hydrogen, and reacted overnight. After completion of the reaction, it was filtered, and the filter cake was washed with methanol. The filtrate was rotate evaporated to dryness to obtain a white solid 2.28 g, at a yield of 92.3%.

4. Preparation of ethyl 2-[3-[4-(2-naphthamido)benzyl]-2-methyl-1H-indol-1-yl]acetate In a dry reaction vessel, ethyl 2-[3-(4-aminobenzyl)-2-methyl-1H-indol-1-yl]acetate (1.644 g, 5.1 mmol) was added, and dissolved in 30 mL dichloromethane. Triethylamine (2.13 mL, 15.3 mmol) was added, and in an ice bath a dichloromethane solution dissolving 2-naphthoyl chloride (1.067 g, 5.6 mmol) was added slowly. After completion of dropwise addition, it was reacted in an ice bath for 1 h, and stirred at room temperature overnight. It was filtered. An aqueous solution of sodium bicarbonate was added, extracted with dichloromethane, rotate evaporated to dryness, chromatographed on a column to obtain a white solid 0.53 g, at a yield of 21.8%.

5. Preparation of 2-[3-[4-(2-naphthamido)benzyl]-2-methyl-1H-indol-1-yl]acetic acid Into a dry reaction vessel, ethyl 2-[3-[4-(2-naphthamido)benzyl]-2-methyl-1H-indol-1-yl]acetate (530 mg, 1.11 mmol), lithium hydroxide monohydrate (140 mg, 3.34 mmol), 5 mL tetrahydrofuran, 5 mL methanol, 10 mL water were added successively, and stirred at room temperature for 1 h. The reaction was monitored to be complete by TLC. The solvent was rotate evaporated. It was adjusted to pH=3-4 with 2 N HCl solution. A solid precipitated, and was washed with ethyl acetate, dichloromethane, acetonitrile to obtain the product 100 mg as a white solid, at a yield of 20.1%.

Mass Spectrum (M+H): 449.2

$^1$H-NMR ($d_6$-DMSO, 400 MHz): δ 10.31 (1H, s), 8.53 (1H, s), 8.05 (1H, dd), 8.02-7.96 (3H, m), 7.65 (2H, d), 7.63-7.57 (2H, m), 7.32 (1H, d), 7.22-7.15 (3H, m), 6.95 (1H, t), 6.86 (1H, t), 4.41 (2H, s), 3.99 (2H, s), 2.33 (3H, s).

Example 3

Preparation of 2-[2-methyl-3-[4-[4-(trifluoromethyl) benzamido]benzyl]-1H-indol-1-yl]acetic acid (Compound 3)

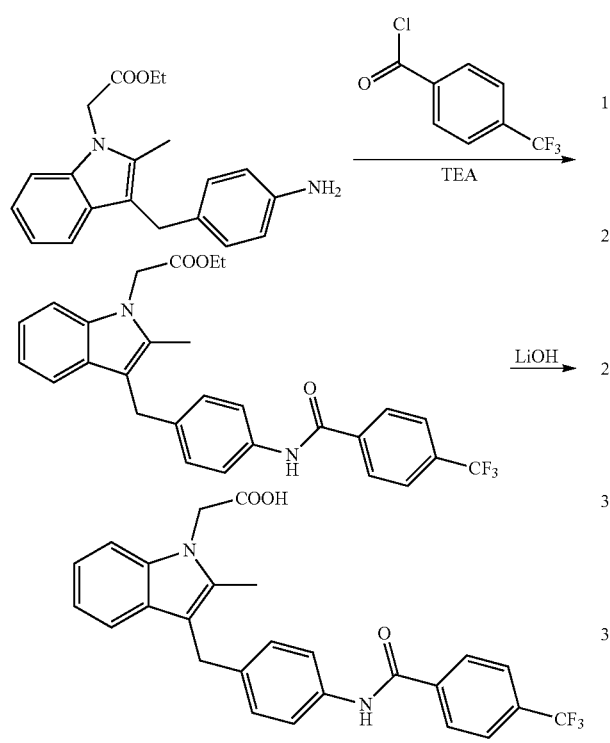

1. Preparation of ethyl 2-[2-methyl-3-[4-[4-(trifluoromethyl)benzamido]benzyl]-1H-indol-1-yl]acetate In a dry reaction vessel, ethyl 2-[3-(4-aminobenzyl)-2-methyl-1H-indol-1-yl]acetate (1.0 g, 3.11 mmol) was added, and dissolved in 15 mL dichloromethane. Triethylamine (1.3 mL, 9.34 mmol) was added, and in an ice bath a dichloromethane solution dissolving 4-trifluoromethylbenzoyl chloride (0.649 g, 3.11 mmol) was added slowly. After completion of dropwise addition, it was reacted in an ice bath for 4 h, and filtered. An aqueous solution of sodium bicarbonate was added, extracted with dichloromethane, rotate evaporated to dryness, chromatographed on a column to obtain a white solid 1.15 g, at a yield of 74.9%.

2. Preparation of 2-[2-methyl-3-[4-[4-(trifluoromethyl)benzamido]benzyl]-1H-indol-1-yl]acetic acid Into a dry reaction vessel, ethyl 2-[2-methyl-3-[4-[4-(trifluoromethyl)benzamido]benzyl]-1H-indol-1-yl]acetate (600 mg, 1.21 mmol), lithium hydroxide monohydrate (153 mg, 3.64 mmol), 10 mL tetrahydrofuran, 10 mL methanol, 10 mL water were weighed, and stirred at room temperature for 1 h. The reaction was monitored to be complete by TLC. The solvent was rotate evaporated. It was adjusted to pH=3-4 with 2 N HCl solution. It was filtered, and the filter cake was washed with 20 mL methanol to obtain the product 480 mg as a white solid, at a yield of 85.1%.

Mass Spectrum (M+H): 467.2

$^1$H-NMR (d$_6$-DMSO, 400 MHz): δ 10.36 (1H, s), 8.10 (2H, d), 7.87 (2H, d), 7.60 (2H, d), 7.33 (1H, d), 7.25 (1H, d), 7.18 (2H, d), 6.98 (1H, t), 6.89 (1H, t), 4.72 (2H, s), 3.99 (2H, s), 2.32 (3H, s).

Example 4

Preparation of 2-[3-[4-(3,4-dichlorobenzamido)benzyl]-2-methyl-1H-indol-1-yl]acetic acid (Compound 4)

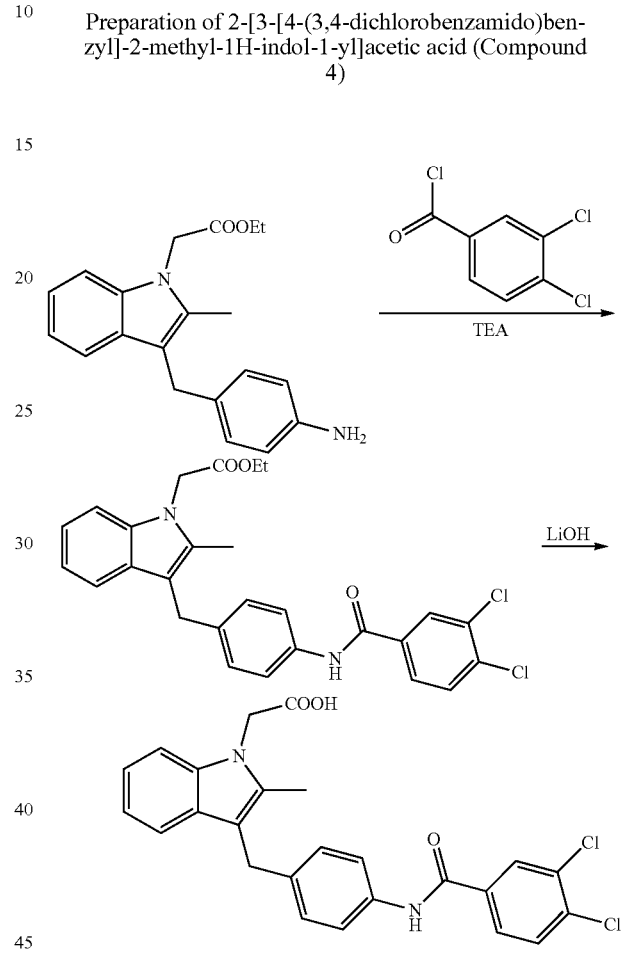

1. Preparation of ethyl 2-[3-[4-(3,4-dichlorobenzamido)benzyl]-2-methyl-1H-indol-1-yl]acetate In a dry reaction vessel, ethyl 2-[3-(4-aminobenzyl)-2-methyl-1H-indol-1-yl]acetate (1.0 g, 3.11 mmol) was added, and dissolved in 15 mL dichloromethane. Triethylamine (1.3 mL, 9.3 mmol) was added, and in an ice bath a dichloromethane solution dissolving 3,4-dichlorobenzoyl chloride (0.652 g, 3.11 mmol) was added slowly. After completion of dropwise addition, it was reacted in an ice bath for 4 h, and filtered. An aqueous solution of sodium bicarbonate was added, extracted with dichloromethane, rotate evaporated to dryness, chromatographed on a column to obtain a white solid 1.23 g, at a yield of 79.7%.

2. Preparation of 2-[3-[4-(3,4-dichlorobenzamido) benzyl]-2-methyl-1H-indol-1-yl]acetic acid Into a dry reaction vessel, ethyl 2-[3-[4-(3,4-dichlorobenzamido)benzyl]-2-methyl-1H-indol-1-yl]acetate (691 mg, 1.39 mmol), lithium hydroxide monohydrate (176 mg, 4.19 mmol), 10 mL tetrahydrofuran, 10 mL methanol, 10 mL water were weighed, and stirred at room temperature for 1 h. The reaction was monitored to be complete by TLC. The solvent was rotate evaporated. It was adjusted to pH=3-4 with 2 N HCl solution. It was filtered, and the filter cake was washed with 20 mL methanol to obtain the product as a white solid 551 mg, at a yield of 84.9%.

Mass Spectrum (M+H): 467.1

$^1$H-NMR (d$_6$-DMSO, 400 MHz): δ 10.29 (1H, s), 8.16 (1H, d), 7.89 (1H, dd), 7.78 (1H, d), 7.58 (2H, d), 7.34 (1H, d), 7.28 (1H, d), 7.18 (2H, d), 7.00 (1H, t), 6.91 (1H, t), 4.83 (2H, s), 3.99 (2H, s), 2.32 (3H, s).

Example 5

Preparation of 2-[3-(4-(2-naphthamido)benzyl)-1H-indazol-1-yl]acetic acid (Compound 5)

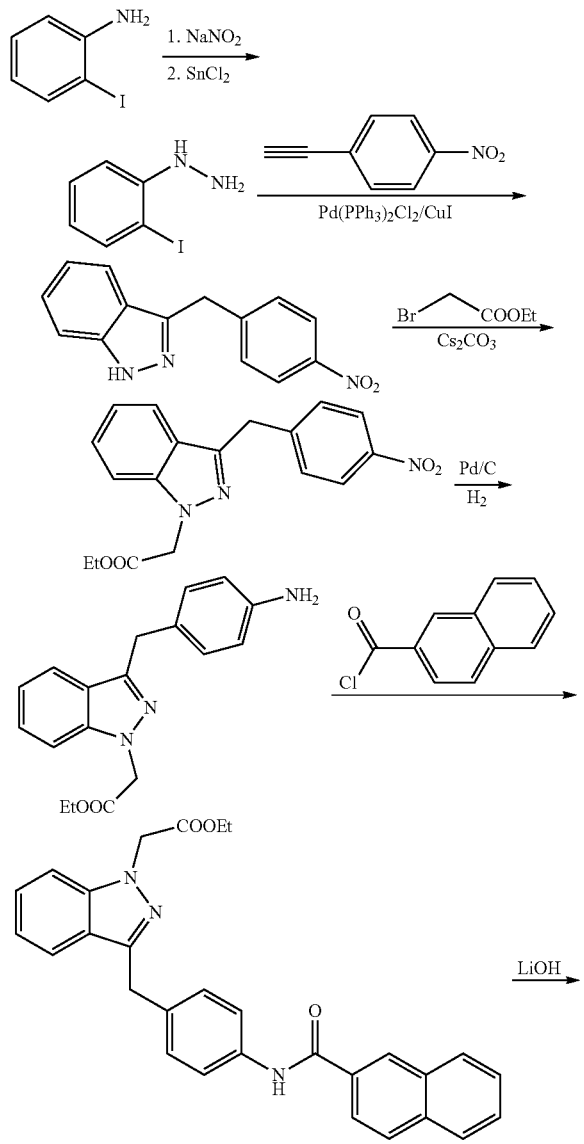

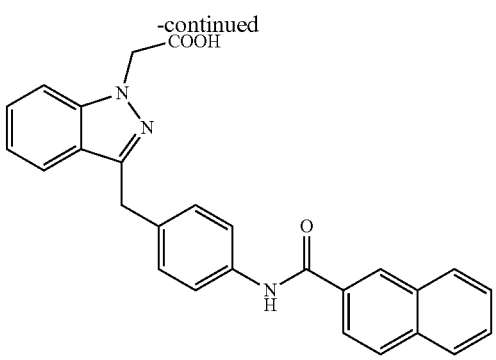

1. Preparation of (2-iodophenyl)hydrazine 21.9 g (100 mmol) o-iodophenyl amine was dissolved in 40 mL concentrated hydrochloric acid. At 0° C., 6.9 g (100 mmol) sodium nitrite (dissolved in 35 mL water) was added dropwise, and stirred at 0° C. for half an hour. Then, SnCl$_2$.2H$_2$O 64.7 g (300 mmol) (dissolved in 70 mL concentrated hydrochloric acid) was added dropwise slowly, and reacted for about 3 h until complete. It was filtered to obtain a white solid, washed with a saturated solution of sodium chloride, and then washed with a mixed solvent of petroleum ether and diethyl ether (1:1). Then, the solid was adjusted to be basic with sodium hydroxide solution. The solid impurity therein was filtered, the aqueous phase was extracted with dichloromethane several times, the organic phases combined, dried, rotate evaporated to dryness to obtain a colorless oil 10.3 g, at a yield of 44.0%.

2. Preparation of 3-(4-nitrobenzyl)-1H-indazole

Into a dry reaction vessel, 10.3 g (44 mmol) (2-iodophenyl) hydrazine, 100 mL toluene, 50 mL triethylamine, 8.41 g (57.2 mmol) p-nitro phenylacetylene, 500 mg (Ph$_3$P)$_2$PdCl$_2$, 250 mg cuprous iodide were respectively added, and reacted at 110° C. under protection of nitrogen for 4.5 h. It was cooled, rotate evaporated to dryness to remove the solvent, chromatographed on a column to obtain a red liquid 2.15 g (8.50 mmol), at a yield of 19.3%.

3. Preparation of ethyl 2-[3-(4-nitrobenzyl)-1H-indazol-1-yl]acetate

Into a dry reaction vessel, 2.15 g (8.49 mmol) 3-(4-nitrobenzyl)-1H-indazole, 10 mL DMF, 1.70 g (10.2 mmol) ethyl bromoacetate, 5.54 g (17.0 mmol) cesium carbonate were respectively added, and reacted at room temperature overnight. It was chromatographed on a column to obtain 1.4 g red solid, at a yield of 48.5%.

4. Preparation of ethyl 2-[3-(4-aminobenzyl)-1H-indazol-1-yl]acetate 1.3 g (3.83 mmol) ethyl 2-[3-(4-nitrobenzyl)-1H-indazol-1-yl]acetate was dissolved in 40 mL methanol. 200 mg palladium on carbon was added, and reacted under an atmosphere of H$_2$ at room temperature overnight. It was filtered to remove solid, rotate evaporated to dryness to remove the solvent, and separated by a preparative chromatography to obtain a white solid 630 mg, at a yield of 53.3%.

5. Preparation of ethyl 2-[3-[4-(2-naphthamido)benzyl]-1H-indazol-1-yl]acetate 630 mg (2.04 mmol) ethyl 2-[3-(4-aminobenzyl)-1H-indazol-1-yl]acetate was dissolved in 20 mL dichloromethane. 0.85 mL (6.11 mmol) triethylamine was added, and in an ice bath a dichloromethane solution dissolving 428 mg (2.25 mmol) 2-naphthoyl chloride was added slowly, and reacted in an ice bath for 3 h. An aqueous solution of sodium bicarbonate was added to quench, extracted with ethyl acetate, rotate evaporated to dryness, chromatographed on a column to obtain a white solid 850 mg, at a yield of 89.7%.

6. Preparation of 2-[3-[4-(2-naphthamido)benzyl]-1H-indazol-1-yl]acetic acid 575 mg (1.24 mmol) ethyl 2-[3-[4-(2-naphthamido)benzyl]-1H-indazol-1-yl]acetate was dissolved in a mixed solution of 10 mL tetrahydrofuran and 3 mL methanol, in an ice bath 10 mL aqueous solution dissolving 333 mg (7.93 mmol) lithium hydroxide monohydrate was added. It was reacted at room temperature for 3 h, and the reaction was monitored to be complete by TLC. Water was added into the system, the pH value was adjusted to be acidic with diluted hydrochloric acid. A solid precipitated, it was filtered, dried to obtain a white solid 470 mg (1.08 mmol), at a yield of 87.1%.

LC-MS (M+H): 436.2

$^1$H NMR ($d_6$-DMSO, 400 MHz) δ: 10.37 (s, 1H), 8.54 (s, 1H), 8.09-7.95 (m, 4H), 7.71 (d, 2H), 7.66-7.57 (m, 3H), 7.56 (d, 1H), 7.34 (td, 1H), 7.29 (d, 2H), 7.07 (td, 1H), 5.20 (s, 2H), 4.25 (s, 2H).

Example 6

Preparation of 2-[3-[4-(4-chlorobenzamido)benzyl]-2-methyl-1H-indol-1-yl]acetic acid (Compound 6)

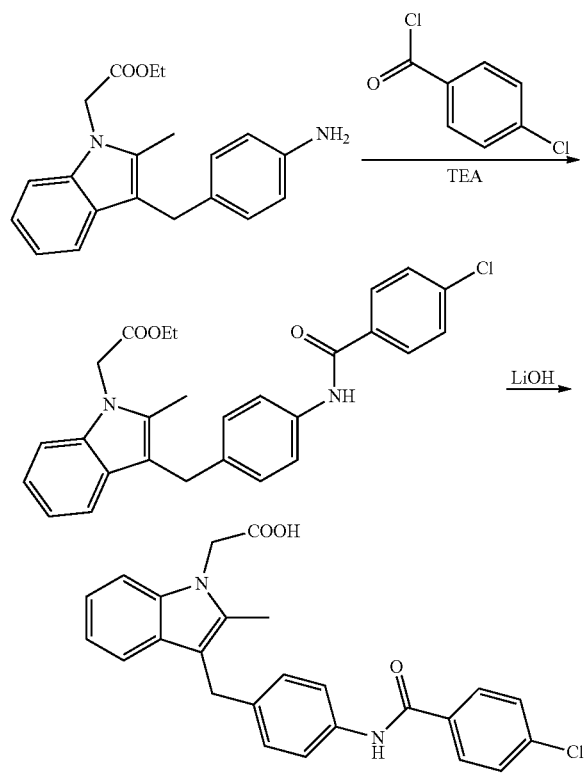

1. Preparation of ethyl 2-[3-[4-(4-chlorobenzamido)benzyl]-2-methyl-1H-indol-1-yl]acetate In a dry reaction vessel, ethyl 2-[3-(4-aminobenzyl)-2-methyl-1H-indol-1-yl]acetate (1.0 g, 3.10 mmol) was added, and dissolved in 15 mL dichloromethane. Triethylamine (1.3 mL, 9.34 mmol) was added, and in an ice bath a dichloromethane solution dissolving 4-chlorobenzoyl chloride (0.544 g, 3.11 mmol) was added slowly. After completion of dropwise addition, it was reacted in an ice bath for 4 h. It was filtered. An aqueous solution of sodium bicarbonate was added, extracted with dichloromethane, rotate evaporated to dryness, chromatographed on a column to obtain a white solid 0.580 g, at a yield of 40.6%.

2. Preparation of 2-[3-[4-(4-chlorobenzamido)benzyl]-2-methyl-1H-indol-1-yl]acetic acid Into a dry reaction vessel, ethyl 2-[3-[4-(4-chlorobenzamido)benzyl]-2-methyl-1H-indol-1-yl]acetate (580 mg, 1.26 mmol), lithium hydroxide monohydrate (159 mg, 3.79 mmol), 10 mL tetrahydrofuran, 10 mL methanol, 10 mL water were weighed, and stirred at room temperature for 1 h. The reaction was monitored to be complete by TLC. The solvent was rotate evaporated. It was adjusted to pH=3-4 with 2 N HCl solution. It was filtered, and the filter cake was washed with 20 mL methanol to obtain the product as a white solid 523 mg, at a yield of 95.9%.

Mass Spectrum (M+H): 433.2

$^1$H-NMR ($d_6$-DMSO, 400 MHz): δ 10.21 (1H, s), 7.93 (2H, d), 7.59 (2H, d), 7.57 (2H, d), 7.35 (1H, d), 7.31 (1H, d), 7.17 (2H, d), 7.01 (1H, t), 6.92 (1H, t), 4.93 (2H, s), 3.99 (2H, s), 2.32 (3H, s).

Example 7

Preparation of 2-[3-[4-(2-naphthamido)benzyl]-2-ethyl-1H-indol-1-yl]acetic acid (Compound 7)

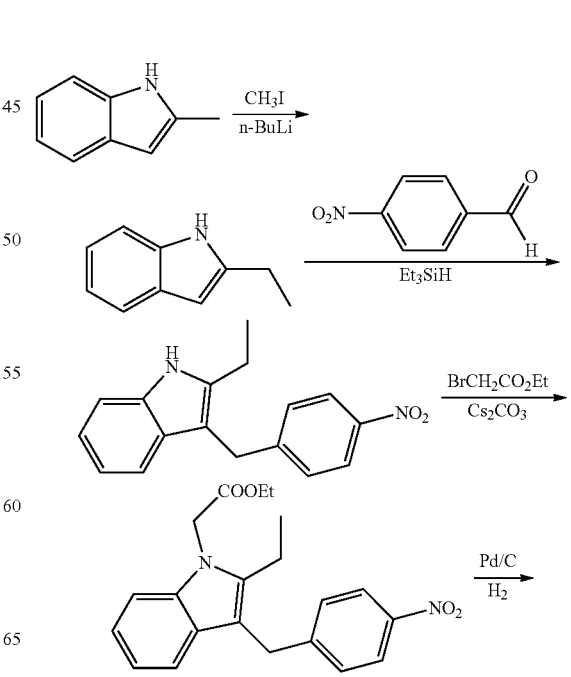

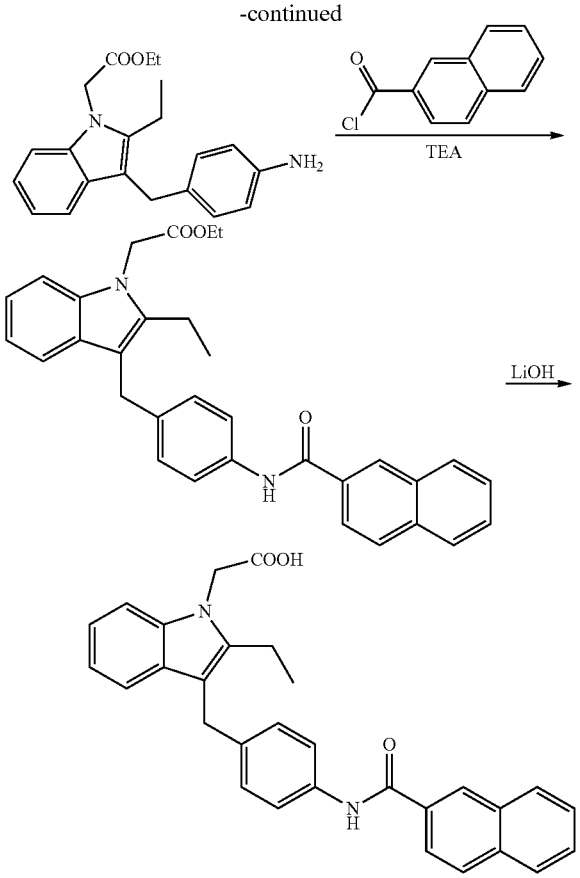

1. Preparation of 2-ethyl-1H-indole

In an ice water bath, 2-methylindole (5 g, 38.1 mmol), 300 mL anhydrous diethyl ether, 2.4 M n-BuLi 47.5 mL (114 mmol), tert-butanol (8.5 g, 75.8 mmol) were added into a reaction vessel. Upon completion of addition, under protection of nitrogen, the reaction was stirred at room temperature for 0.5 h. Then the system was cooled to −70° C., and iodomethane (10.245 g, 72.2 mmol) was added dropwise. Upon completion of addition, it was reacted for 2 h maintaining this temperature. Then it was warmed up to −40° C. 2 mL water was added, and then warmed up to room temperature. The system was poured into water, adjusted to pH=6, extracted with diethyl ether, dried and rotate evaporated to dryness to obtain the product 3.74 g, at a yield of 67.7%.

2. Preparation of 2-ethyl-3-(4-nitrobenzyl)-1H-indole

In an ice water bath, trifluoroacetic acid (4.4 g, 38.6 mmol), triethylsilane (9.02 g, 77.6 mmol), dichloromethane 15 mL were added into a reaction vessel. After stirring for 5 min, a dichloromethane solution dissolving 2-ethyl-1H-indole (3.74 g, 25.8 mmol) and p-nitro benzaldehyde (4.29 g, 28.4 mmol) was added dropwise slowly into the reaction vessel. After completion of dropwise addition it was reacted maintaining this temperature for 1 h, adjusted to pH=8-9 with 2 M solution of sodium hydroxide. An aqueous solution of sodium chloride was added, and extracted with dichloromethane. The extract was dried over anhydrous sodium sulfate, concentrated to dryness to obtain a red brown solid, washed with a small amount of diethyl ether to obtain a yellow powdered solid 3 g, at a yield of 41.5%.

3. Preparation of ethyl 2-[2-ethyl-3-(4-nitrobenzyl)-1H-indol-1-yl]acetate

2-Ethyl-3-(4-nitrobenzyl)-1H-indole (3.0 g, 10.7 mmol) was weighed, and dissolved in 30 mL DMF. Cesium carbonate (6.98 g, 21.4 mmol) was added, and stirred at room temperature for 15 min. Ethyl bromoacetate (1.97 g, 11.8 mmol) was added, reacted at room temperature for 10 h, and filtered. The filtrate was added into water, and extracted with ethyl acetate. The extract was washed with water and a saturated solution of sodium chloride, rotate evaporated to dryness, purified by preparative liquid phase to obtain a yellow solid 350 mg, at a yield of 8.97%.

4. Preparation of ethyl 2-[3-(4-aminobenzyl)-2-ethyl-1H-indol-1-yl]acetate

Into a dry reaction vessel, ethyl 2-[2-ethyl-3-(4-nitrobenzyl)-1H-indol-1-yl]acetate (350 mg, 0.96 mmol) was added, and dissolved in 10 mL methanol. 10% Pd/C 50 mg was added, purged with dry hydrogen, and reacted for 1 h. After completion of the reaction, it was filtered, and the filter cake was washed with methanol. The filtrate was rotate evaporated to dryness to obtain a white solid 288 mg, at a yield of 89.6%.

5. Preparation of ethyl 2-[3-[4-(2-naphthamido)benzyl]-2-ethyl-1H-indol-1-yl]acetate In a dry reaction vessel, ethyl 2-[3-(4-aminobenzyl)-2-ethyl-1H-indol-1-yl]acetate (288 mg, 0.86 mmol) was added, and dissolved in 7 mL dichloromethane. Triethylamine (0.36 mL, 2.59 mmol) was added, in an ice bath a dichloromethane solution 2 mL dissolving 2-naphthoyl chloride (163 mg, 0.86 mmol) was added slowly. After completion of dropwise addition, it was reacted in an ice bath for 1 h, and stirred at room temperature overnight. Water was added into the system, extracted with dichloromethane, rotate evaporated to dryness to obtain a crude. It was washed again with a small amount of acetonitrile to obtain the yellow product 340 mg, at a yield of 80.2%.

6. Preparation of 2-[3-[4-(2-naphthamido)benzyl]-2-ethyl-1H-indol-1-yl]acetic acid Into a dry reaction vessel, ethyl 2-[3-[4-(2-naphthamido)benzyl]-2-ethyl-1H-indol-1-yl]acetate (340 mg, 0.69 mmol), lithium hydroxide monohydrate (117 mg, 2.79 mmol), 5 mL tetrahydrofuran, 5 mL water were weighed, and stirred at room temperature for 2 h. The reaction was monitored to be complete by TLC, the system was added 10 mL water, and adjusted to pH=5 with 2 N HCl solution. A solid precipitated, it was pumping filtered, washed with dichloromethane to obtain the product as a light yellow solid 240 mg, at a yield of 75.2%.

Mass Spectrum (M+H): 463.2

$^1$H-NMR (d$_6$-DMSO, 400 MHz): δ 10.34 (1H, s), 8.53 (1H, s), 8.09-7.95 (4H, m), 7.70-7.58 (4H, m), 7.35 (1H, d), 7.29 (1H, d), 7.18 (2H, d), 7.03 (1H, t), 6.94 (1H, t), 4.93 (2H, s), 4.02 (2H, s), 2.77 (2H, q), 1.06 (3H, t).

Example 8

Preparation of 2-[3-[4-(4-chlorobenzamido)benzyl]-1H-indazol-1-yl]acetic acid (Compound 8)

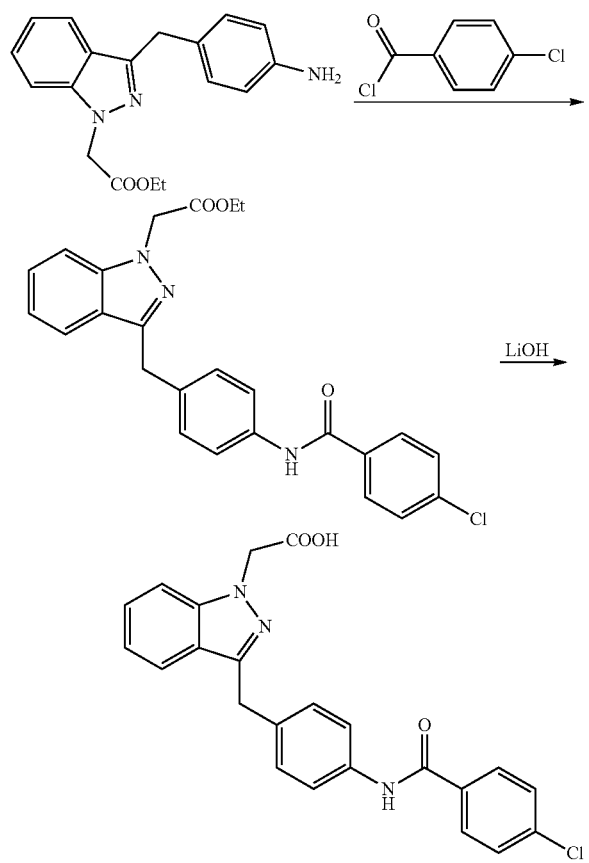

1. Preparation of ethyl 2-[3-[4-(4-chlorobenzamido)benzyl]-1H-indazol-1-yl]acetate 220 mg (0.711 mmol) ethyl 2-[3-(4-aminobenzyl)-1H-indazol-1-yl]acetate was dissolved in 20 mL dichloromethane, and triethylamine 0.15 mL (1.08 mmol) was added. The system was placed in an ice bath, and 137 mg (0.78 mmol) p-chlorobenzoyl chloride was added slowly. Upon completion of addition, the reaction was monitored to be complete by TLC. Water was added, extracted with ethyl acetate, and separated by a preparative chromatography to obtain 100 mg a white solid, at a yield of 31.4%.

2. Preparation of 2-[3-[4-(4-chlorobenzamido)benzyl]-1H-indazol-1-yl]acetic acid Ethyl 2-[3-[4-(4-chlorobenzamido)benzyl]-1H-indazol-1-yl]acetate (100 mg, 0.223 mmol) was dissolved in 3 mL tetrahydrofuran, and 1 mL methanol, 3 mL water were added. In an ice bath was, 47 mg (1.12 mmol) lithium hydroxide monohydrate was added. I was moved to be at room temperature and reacted for 10 minutes. The reaction was monitored to be complete by TLC. Diluted hydrochloric acid was added to adjust pH to be acidic. Water was added, pumping filtered, dried to obtain a white solid 70 mg, at a yield of 74.9%

LC-MS (M+H): 420.1

$^1$H NMR ($d_6$-DMSO, 400 MHz) δ: 10.27 (1H, s), 7.95 (2H, d), 7.64 (2H, d), 7.57 (2H, d), 7.52 (1H, d), 7.36 (1H, d), 7.29-7.20 (3H, m), 6.97 (1H, t), 4.70 (2H, s), 4.20 (2H, s).

Example 9

Preparation of 2-[1-[4-(2-naphthamido)benzyl]-1H-indazol-3-yl]acetic acid (Compound 9)

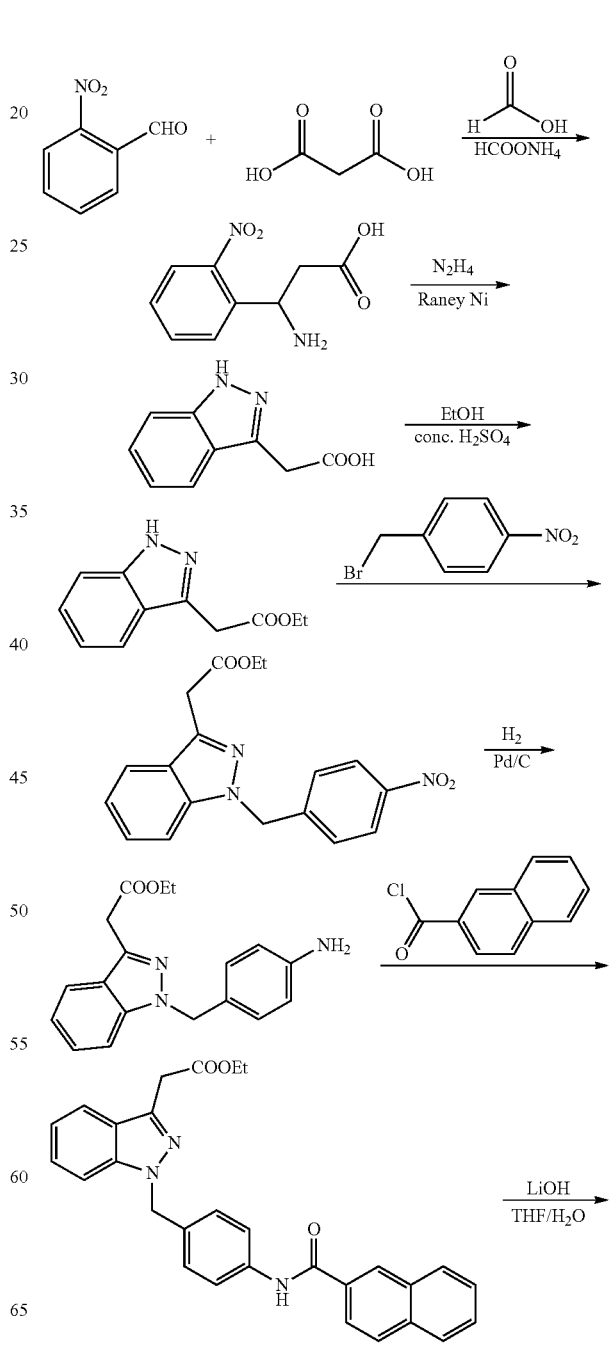

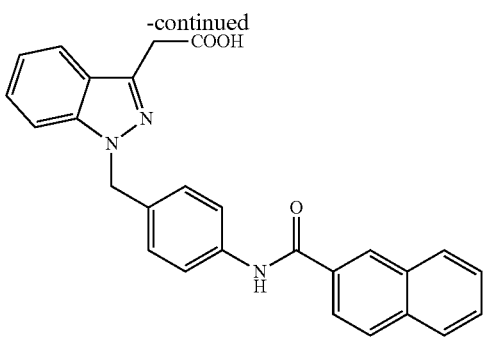

1. Preparation of 3-amino-3-(2-nitrophenyl)propionic acid o-Nitrobenzaldehyde (20.4 g, 0.135 mol), formic acid (20.3 mL, 0.539 mol) and malonic acid (18.3 g, 0.176 mol) were stirred at 45° C. for half an hour. Then ammonium formate (21.3 g, 0.338 mol) was added thereto, the reaction temperature was raised to 70° C. and stirred for 1 hour, and then stirred at 95° C. for another 4 hours. Then concentrated hydrochloric acid (50 mL) was added and further stirred maintaining this temperature for another 1 hour. It was cooled. 25 mL water was added, and washed twice with ethyl acetate (2×25 mL). The aqueous phase was adjusted to pH 4.2 with 50% potassium hydroxide solution. A solid precipitated. It was pumping filtered, and dried in vacuum to obtain a yellow solid 18.33 g, at a yield of 64.6%.

2. Preparation of 2-(1H-indazol-3-yl)acetic acid

3-Amino-3-(2-nitrophenyl) propionic acid (15 g, 71.4 mmol) was dissolved in a mixed solution of 5% sodium hydroxide solution (85 mL) and 85% hydrazine hydrate (5 mL). The reaction was heated to 80° C., and then Raney nickel (2×25 mg) was added carefully. After reacted for half an hour, it was cooled, adjusted to pH≈2 with 6 N hydrochloric acid. A solid precipitated was pumping filtered, dried in vacuum to obtain a yellow solid 6.86 g, at a yield of 54.5%.

3. Preparation of ethyl 2-(1H-indazol-3-yl)acetate 2-(1H-indazol-3-yl)acetic acid (3.9 g, 22.1 mmol) was dissolved in anhydrous ethanol (100 mL) concentrated sulfuric acid (5 mL), and heated under reflux for 16 hours. It was concentrated under reduce pressure to remove most of ethanol, then water (30 mL) was added, and extracted with ethyl acetate. The organic phase was dried over anhydrous sodium sulfate, concentrated to obtain the product 3.96 g, at a yield of 87.8%.

4. Preparation of ethyl 2-[1-(4-nitrobenzyl)-1H-indazol-3-yl]acetate

Ethyl 2-(1H-indazol-3-yl)acetate (408 mg, 2.0 mmol) was dissolved in N,N-dimethylformamide (20 mL), 60% sodium hydride (96 mg, 2.4 mmol) was added, and stirred at room temperature for half an hour. Then p-nitro benzyl bromide (475 mg, 2.2 mmol) was added, and reacted for 1 hour. Then, the reaction solution was poured into ice water and extracted with ethyl acetate. The organic phase was dried over anhydrous sodium sulfate, concentrated, chromatographed on a silica gel column (petroleum ether:ethyl acetate=2:1) to obtain a yellow solid 354 mg, at a yield of 52.1%.

5. Preparation of ethyl 2-[1-(4-aminobenzyl)-1H-indazol-3-yl]acetate

Ethyl 2-[1-(4-nitrobenzyl)-1H-indazol-3-yl]acetate (340 mg, 1.04 mmol) was dissolved in methanol (20 mL). 10% Pd/C (20 mg) was added, and reacted under hydrogen atmosphere for half an hour. TLC (petroleum ether:ethyl acetate=2:1) indicated that starting material disappeared. It was filtered to remove solid, rotate evaporated to dryness to remove the solvent. The resulting solid was used for the next step directly.

6. Preparation of ethyl 2-[1-[4-(2-naphthamido)benzyl]-1H-indazol-3-yl]acetate The crude ethyl 2-[1-(4-aminobenzyl)-1H-indazol-3-yl]acetate (about 1.04 mmol) obtained in the last step and triethylamine (1.4 mL) were dissolved in dichloromethane (15 mL). In an ice bath, a dichloromethane solution (10 mL) of 2-naphthoyl chloride (210 mg, 1.1 mmol) was added dropwise slowly. Upon completion of the dropwise addition, it was reacted at room temperature for 16 hours. An aqueous solution of sodium bicarbonate was added to quench. It was extracted with ethyl acetate. The organic phase was dried over anhydrous sodium sulfate, and filtered. The filtrate was removed under reduced pressure, and the resulting residue was chromatographed on a silica gel column (petroleum ether:ethyl acetate=2:1) to obtain a white solid 226 mg, at a total yield over two steps of reactions of 46.9%.

7. Preparation of 2-[1-[4-(2-naphthamido)benzyl]-1H-indazol-3-yl]acetic acid Ethyl 2-[1-[4-(2-naphthamido)benzyl]-1H-indazol-3-yl]acetate (226 mg, 0.488 mmol) was dissolved in tetrahydrofuran (10 mL), and in an ice bath 10 mL aqueous solution of lithium hydroxide monohydrate (62 mg, 1.48 mmol) was added. It was reacted at room temperature for 3 h, and the reaction was monitored to be complete by TLC. Water was added into the system, and adjusted to pH≈3-4 with diluted hydrochloric acid. A solid precipitated. It was filtered, and dried to obtain a white solid 123 mg, at a yield of 58%.

LC-MS (M+H): 436.2

$^1$H NMR (d$_6$-DMSO, 400 MHz) δ: 10.42 (s, 1H), 8.53 (s, 1H), 8.08-7.94 (m, 4H), 7.76-7.68 (m, 3H), 7.66-7.55 (m, 3H), 7.35 (t, 1H), 7.24 (d, 2H), 7.09 (t, 1H), 5.55 (s, 2H), 3.82 (s, 2H).

Example 10

Preparation of 2-[1-[4-(4-chlorobenzamido)benzyl]-1H-indazol-3-yl]acetic acid (Compound 10)

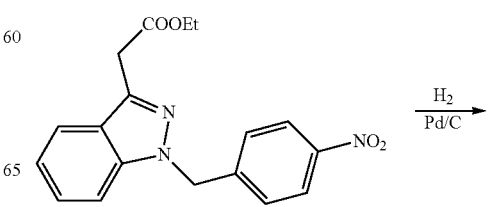

41

-continued

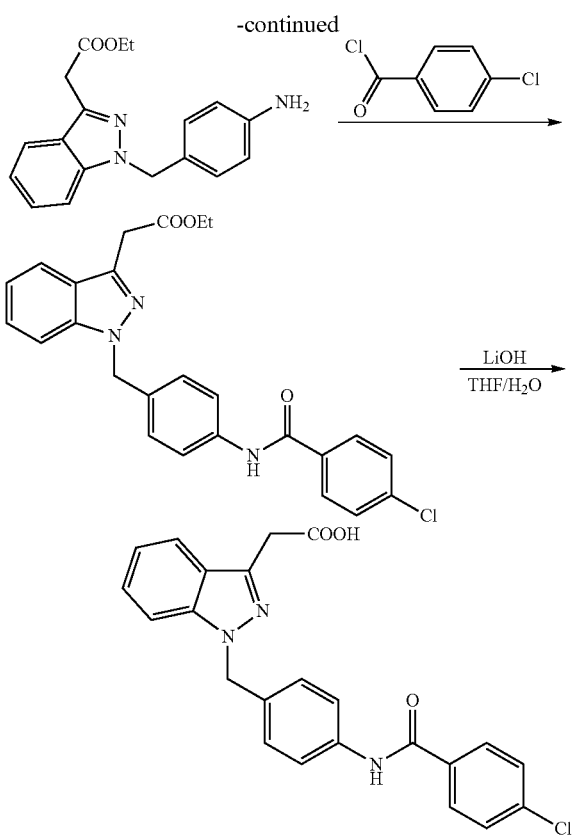

1. Preparation of ethyl 2-[1-(4-aminobenzyl)-1H-indazol-3-yl]acetate

Ethyl 2-[1-(4-nitrobenzyl)-1H-indazol-3-yl]acetate (225 mg, 0.663 mmol) was dissolved in methanol (20 mL). 10% Pd/C(18 mg) was added, and reacted under hydrogen atmosphere for half an hour. TLC (petroleum ether:ethyl acetate=2:1) indicated that starting material disappeared. It was filtered to remove solid, rotate evaporated to dryness to remove the solvent, and the resulting solid was used for the next step directly.

2. Preparation of ethyl 2-[1-[4-(4-chlorobenzamido)benzyl]-1H-indazol-3-yl]acetate The crude ethyl 2-[1-(4-aminobenzyl)-1H-indazol-3-yl] acetate (about 0.663 mmol) obtained in the last step and triethylamine (1.0 mL) were dissolved in dichloromethane (15 mL). In an ice bath, a dichloromethane solution (10 mL) of 4-chlorobenzoyl chloride (117 mg, 0.669 mmol) was added dropwise slowly. Upon completion of the dropwise addition, it was reacted at room temperature for 16 hours. An aqueous solution of sodium bicarbonate was added to quench. It was extracted with ethyl acetate. The organic phase was dried over anhydrous sodium sulfate, and filtered. The filtrate was rotate evaporated. The resulting residue was chromatographed on a silica gel column (petroleum ether:ethyl acetate=2:1) to obtain a white solid 159 mg, at a total yield over two steps of reactions of 53.5%.

3. Preparation of 2-[1-[4-(4-chlorobenzamido)benzyl]-1H-indazol-3-yl]acetic acid Ethyl 2-[1-[4-(4-chlorobenzamido)benzyl]-1H-indazol-3-yl]acetate (159 mg, 0.355 mmol) was dissolved in tetrahydrofuran (10 mL). In an ice bath, 10 mL aqueous solution dissolving lithium hydroxide monohydrate (42 mg, 1.0 mmol) was added. It was reacted at room temperature for 3 h, and the reaction was monitored to be complete by TLC. Water was added into the system, and adjusted to pH≈3-4 with diluted hydrochloric acid. A solid precipitated. It was filtered, and dried to obtain a white solid 144 mg, at a yield of 96.6%.

LC-MS (M+H): 420.10

$^1$H NMR (d$_6$-DMSO, 400 MHz) δ: 12.62 (br s, 1H), 10.30 (s, 1H), 7.93 (d, 2H), 7.78-7.63 (m, 4H), 7.58 (d, 2H), 7.36 (t, 1H), 7.22 (d, 2H), 7.11 (t, 1H), 5.56 (s, 2H), 3.91 (s, 2H).

Example 11

Preparation of 2-[1-[4-(2-naphthamido)benzyl]-5-fluoro-1H-indazol-3-yl]acetic acid (Compound 11)

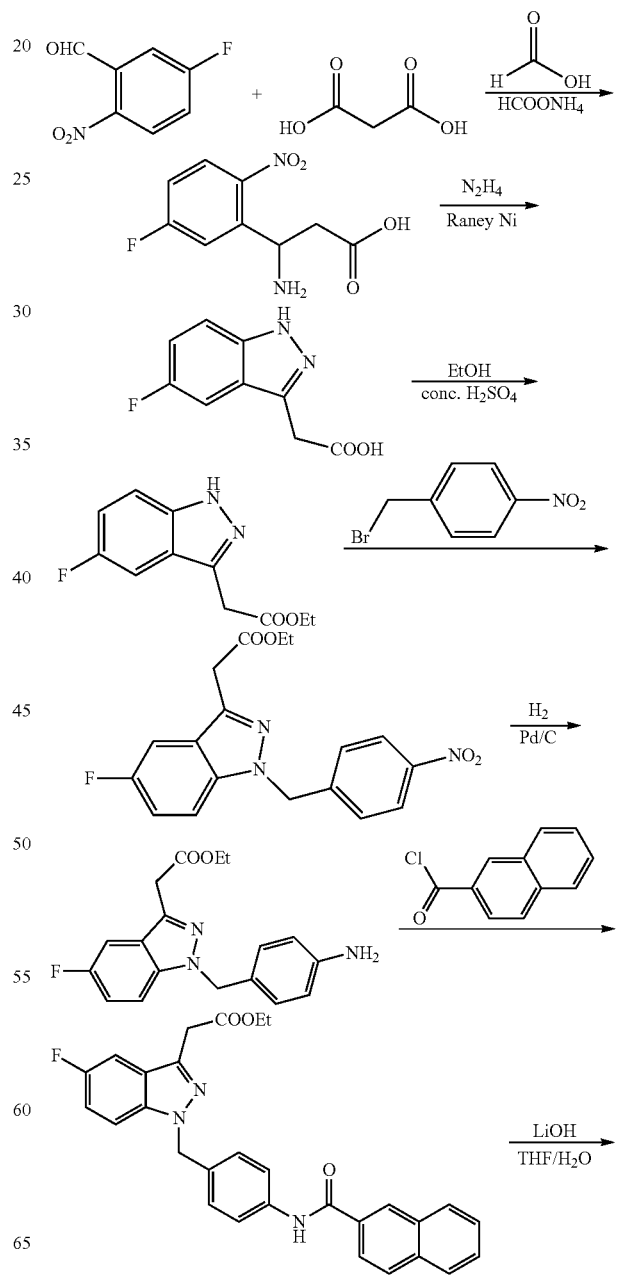

-continued

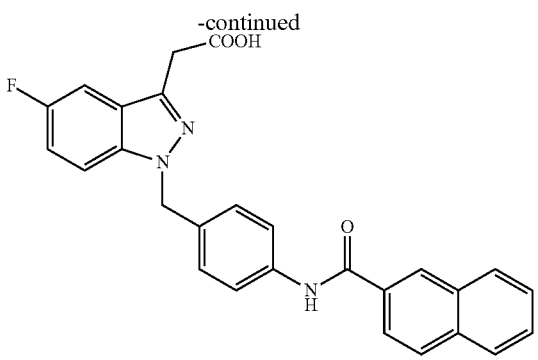

1. Preparation of 3-amino-3-(5-fluoro-2-nitrophenyl)propionic acid

5-Fluoro-2-nitrobenzaldehyde (16.91 g, 0.10 mol), formic acid (15.2 mL, 0.40 mol) and malonic acid (13.52 g, 0.13 mol) were stirred at 45° C. for half an hour. Then ammonium formate (15.76 g, 0.25 mol) was added thereto. The reaction temperature was raised to 70° C. and stirred for 1 hour. Then it was stirred at 95° C. for another 4 hours, and then concentrated hydrochloric acid (38 mL) was added and stirred maintaining this temperature for another 1 hour. It was cooled. Water (20 mL) was added, extracted with ethyl acetate (2×25 mL), and the aqueous phase was adjusted to pH≈4.2 with 50% potassium hydroxide solution. A solid precipitated, pumping filtered, dried in vacuum to obtain a yellow solid 15.32 g, at a yield of 67.1%.

2. Preparation of 2-(5-fluoro-1H-indazol-3-yl)acetic acid

3-Amino-3-(5-fluoro-2-nitrophenyl)propionic acid (15.32 g, 67.1 mmol) was dissolved in a mixed solution of 5% sodium hydroxide solution (80 mL) and 85% hydrazine hydrate (5 mL). The reaction was heated to 80° C., and then Raney nickel (2×25 mg) was added carefully. After reacted for half an hour, it was cooled, and adjusted to pH=2 with 6 N hydrochloric acid. A solid precipitated, pumping filtered, dried in vacuum to obtain a yellow solid 1.12 g, at a yield of 8.6%.

3. Preparation of ethyl 2-(5-fluoro-1H-indazol-3-yl)acetate 2-(5-Fluoro-1H-indazol-3-yl)acetic acid (1.12 g, 5.77 mmol) was dissolved in anhydrous ethanol (50 mL) concentrated sulfuric acid (1.5 mL), and heated under reflux for 16 hours. After concentrated under reduce pressure to remove most of ethanol, water (20 mL) was added, and extracted with ethyl acetate. The organic phase was dried over anhydrous sodium sulfate, and concentrated to obtain the product 0.48 g, at a yield of 37.4%.

4. Preparation of ethyl 2-[5-fluoro-1-(4-nitrobenzyl)-1H-indazol-3-yl]acetate Ethyl 2-(5-fluoro-1H-indazol-3-yl)acetate (0.48 g, 2.16 mmol) was dissolved in anhydrous tetrahydrofuran (30 mL). Cesium carbonate (2.11 g, 6.48 mmol) was added, and stirred at room temperature for half an hour. Then p-nitro benzyl bromide (466 mg, 2.16 mmol) was added. After reacted for 16 hours, the solid was filtered. The filtrate was concentrated, chromatographed on a silica gel column (petroleum ether:ethyl acetate=2:1) to obtain a yellow solid 295 mg, at a yield of 38.2%.

5. Preparation of ethyl 2-[1-(4-aminobenzyl)-5-fluoro-1H-indazol-3-yl]acetate Ethyl 2-[5-fluoro-1-(4-nitrobenzyl)-1H-indazol-3-yl]acetate (137 mg, 0.383 mmol) was dissolved in methanol (20 mL). 10% Pd/C (10 mg) was added, and reacted under hydrogen atmosphere for half an hour. TLC (petroleum ether:ethyl acetate=2:1) indicated that starting material disappeared. It was filtered to remove solid, rotate evaporated to dryness to remove the solvent, and the resulting solid was used for the next step directly.

6. Preparation of ethyl 2-[1-[4-(2-naphthamido)benzyl]-5-fluoro-1H-indazol-3-yl]acetate The crude (about 0.383 mmol) obtained in the last step and triethylamine (1.4 mL) were dissolved in dichloromethane (15 mL). In an ice bath a dichloromethane solution (10 mL) of 2-naphthoyl chloride (72 mg, 0.38 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, filtered, and the filtrate was concentrated under reduce pressure, chromatographed on a silica gel column (petroleum ether:ethyl acetate=2:1) to obtain a white solid 100 mg, at a total yield over two steps of reactions of 54.3%.

7. Preparation of 2-[1-[4-(2-naphthamido)benzyl]-5-fluoro-1H-indazol-3-yl]acetic acid Ethyl 2-[1-[4-(2-naphthamido)benzyl]-5-fluoro-1H-indazol-3-yl]acetate (100 mg, 0.208 mmol) was dissolved in tetrahydrofuran (10 mL), and in an ice bath 10 mL aqueous solution dissolving lithium hydroxide monohydrate (44 mg, 1.05 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried to obtain a white solid 90 mg, at a yield of 95.7%.

LC-MS (M+H): 453.7

$^1$H NMR (d$_6$-DMSO, 400 MHz) δ: 10.43 (s, 1H), 8.52 (s, 1H), 8.10-7.93 (m, 4H), 7.75-7.67 (m, 3H), 7.66-7.56 (m, 2H), 7.49 (d, 1H), 7.32-7.21 (m, 3H), 5.57 (s, 2H), 3.90 (s, 2H).

Example 12

Preparation of 2-[1-[4-(2-naphthamido)benzyl]-6-fluoro-1H-indazol-3-yl]acetic acid (Compound 12)

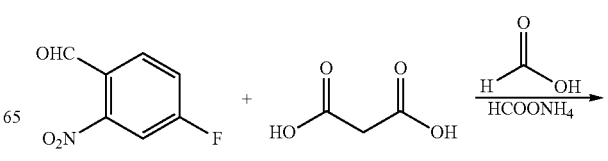

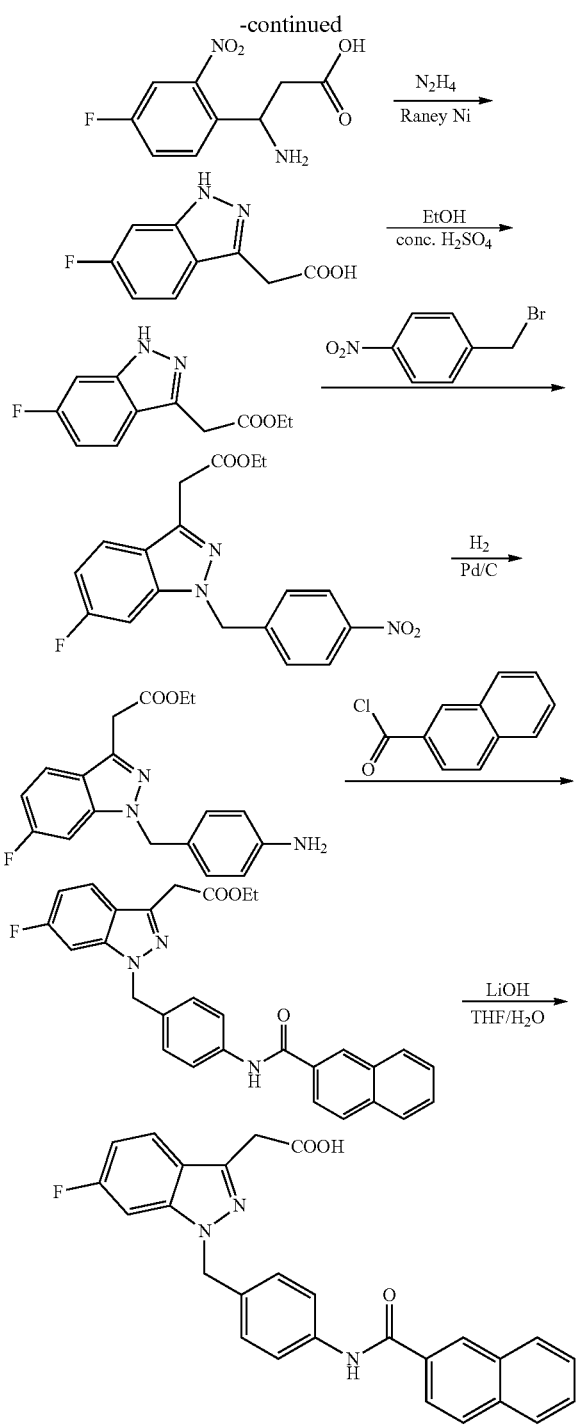

1. Preparation of 3-amino-3-(4-fluoro-2-nitrophenyl)propionic acid

4-Fluoro-2-nitrobenzaldehyde (16.91 g, 0.10 mol), formic acid (15.2 mL, 0.40 mol) and malonic acid (13.52 g, 0.13 mol) were stirred at 45° C. for half an hour, and then ammonium formate (15.76 g, 0.25 mol) was added thereto. The reaction temperature was raised to 70° C. and stirred for 1 hour, and then stirred at 9° C. for another 4 hours. Then concentrated hydrochloric acid (38 mL) was added and stirred maintaining this temperature for another 1 hour. It was cooled, water (20 mL) was added, and extracted with ethyl acetate (2×25 mL). The organic phase was discarded, the aqueous phase was adjusted to pH≈4.2 with 50% potassium hydroxide solution. A solid precipitated, pumping filtered, dried in vacuum to obtain a yellow solid 16.71 g, at a yield of 73.2%.

2. Preparation of 2-(6-fluoro-1H-indazol-3-yl)acetic acid

3. Prep-Amino-3-(4-fluoro-2-nitrophenyl)propionic acid (16.71 g, 73.2 mmol) was dissolved in a mixed solution of 5% sodium hydroxide solution (80 mL) and 85% hydrazine hydrate (5 mL). The reaction was heated to 80° C., and then Raney nickel (2×25 mg) was added carefully, and reacted for half an hour. Then it was cooled, and adjusted to pH≈2 with 6 N hydrochloric acid. A solid precipitated, pumping filtered, dried in vacuum to obtain a yellow solid 4.63 g, at a yield of 32.5%.

3. Preparation of ethyl 2-(6-fluoro-1H-indazol-3-yl)acetate 2-(6-Fluoro-1H-indazol-3-yl)acetic acid (4.63 g, 23.8 mmol) was dissolved in anhydrous ethanol (60 mL) concentrated sulfuric acid (2.0 mL), and heated under reflux for 16 hours. After concentrated under reduce pressure to remove most of ethanol, water (20 mL) was added, and extracted with ethyl acetate. The organic phase was dried over anhydrous sodium sulfate, and concentrated to obtain the product 2.08 g, at a yield of 39.3%.

4. Preparation of ethyl 2-[6-fluoro-1-(4-nitrobenzyl)-1H-indazol-3-yl]acetate Ethyl 2-(6-fluoro-1H-indazol-3-yl)acetate (2.08 g, 9.36 mmol) was dissolved in anhydrous tetrahydrofuran (30 mL). Cesium carbonate (9.15 g, 28.1 mmol) was added, and stirred at room temperature for half an hour. Then p-nitro benzyl bromide (2.02 g, 9.35 mmol) was added, and reacted for 16 hours. Then the solid was filtered. The filtrate was concentrated, chromatographed on a silica gel column (petroleum ether:ethyl acetate=2:1) to obtain a yellow solid 1.38 g, at a yield of 41.2%.

5. Preparation of ethyl 2-[1-(4-aminobenzyl)-6-fluoro-1H-indazol-3-yl]acetate Ethyl 2-[6-fluoro-1-(4-nitrobenzyl)-1H-indazol-3-yl]acetate (357 mg, 1.0 mmol) was dissolved in methanol (20 mL). 10% Pd/C (15 mg) was added, and reacted under hydrogen atmosphere for half an hour. TLC (petroleum ether:ethyl acetate=2:1) indicated that starting material disappeared. It was filtered to remove solid, rotate evaporated to dryness to remove the solvent, and the resulting solid was used for the next step directly.

6. Preparation of ethyl 2-[1-[4-(2-naphthamido)benzyl]-6-fluoro-1H-indazol-3-yl]acetate The crude ethyl 2-[1-(4-aminobenzyl)-6-fluoro-1H-indazol-3-yl]acetate (about 1.0 mmol) obtained in the last step and triethylamine (0.5 mL) were dissolved in dichloromethane (15 mL). In an ice bath, dichloromethane solution (10 mL) of 2-naphthoyl chloride (191 mg, 1.0 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, and filtered. The filtrate was concentrated under reduce pressure, chromatographed on a silica gel column (petroleum ether:ethyl acetate=2:1) to obtain a white solid 205 mg, at a total yield over two steps of reactions of 42.6%.

7. Preparation of 2-[1-[4-(2-naphthamido)benzyl]-6-fluoro-1H-indazol-3-yl]acetic acid Ethyl 2-[1-[4-(2-naphthamido)benzyl]-6-fluoro-1H-indazol-3-yl]acetate (205 mg, 0.426 mmol) was dissolved in tetrahydrofuran (15 mL), and in an ice bath 10 mL aqueous solution dissolving lithium hydroxide monohydrate (54 mg, 1.29 mmol) was added. It was reacted at room temperature for 3 h, and the reaction was monitored to be complete by TLC. Water was added into the system, adjusted to pH≈3-4 with diluted hydrochloric acid. A solid precipitated, which was filtered and dried to obtain a white solid 165 mg, at a yield of 85.4%.

LC-MS (M+H): 454.2

$^1$H NMR (d$_6$-DMSO, 400 MHz) δ: 10.43 (s, 1H), 8.54 (s, 1H), 8.09-7.95 (m, 4H), 7.78-7.71 (m, 3H), 7.67-7.54 (m, 3H), 7.26 (d, 2H), 7.00 (t, 1H), 5.53 (s, 2H), 3.91 (s, 2H).

Example 13

Preparation of 2-[1-[4-(6-fluoro-2-naphthamido)benzyl]-1H-indazol-3-yl]acetic acid (Compound 13)

1. Preparation of ethyl 2-[1-(4-nitrobenzyl)-1H-indazol-3-yl]acetate

Ethyl 2-(1H-indazol-3-yl)acetate (9.78 g, 47.9 mmol) was dissolved in anhydrous tetrahydrofuran (100 mL). Cesium carbonate (46.81 g, 143.7 mmol) was added, and stirred at room temperature for half an hour. Then p-nitro benzyl bromide (10.36 g, 47.96 mmol) was added, reacted for 16 hours, and then the solid was filtered. The filtrate was concentrated, chromatographed on a silica gel column (petroleum ether:ethyl acetate=2:1) to obtain a yellow solid 12.68 g, at a yield of 78.1%.

2. Preparation of ethyl 2-[1-(4-aminobenzyl)-1H-indazol-3-yl]acetate

Ethyl 2-[1-(4-nitrobenzyl)-1H-indazol-3-yl]acetate (340 mg, 1.0 mmol) was dissolved in methanol (20 mL). 10% Pd/C(20 mg) was added, and reacted under hydrogen atmosphere for half an hour. TLC (petroleum ether:ethyl acetate=2:1) indicated that starting material disappeared. It was filtered to remove solid, rotate evaporated to dryness to remove the solvent, and the resulting solid was used for the next step directly.

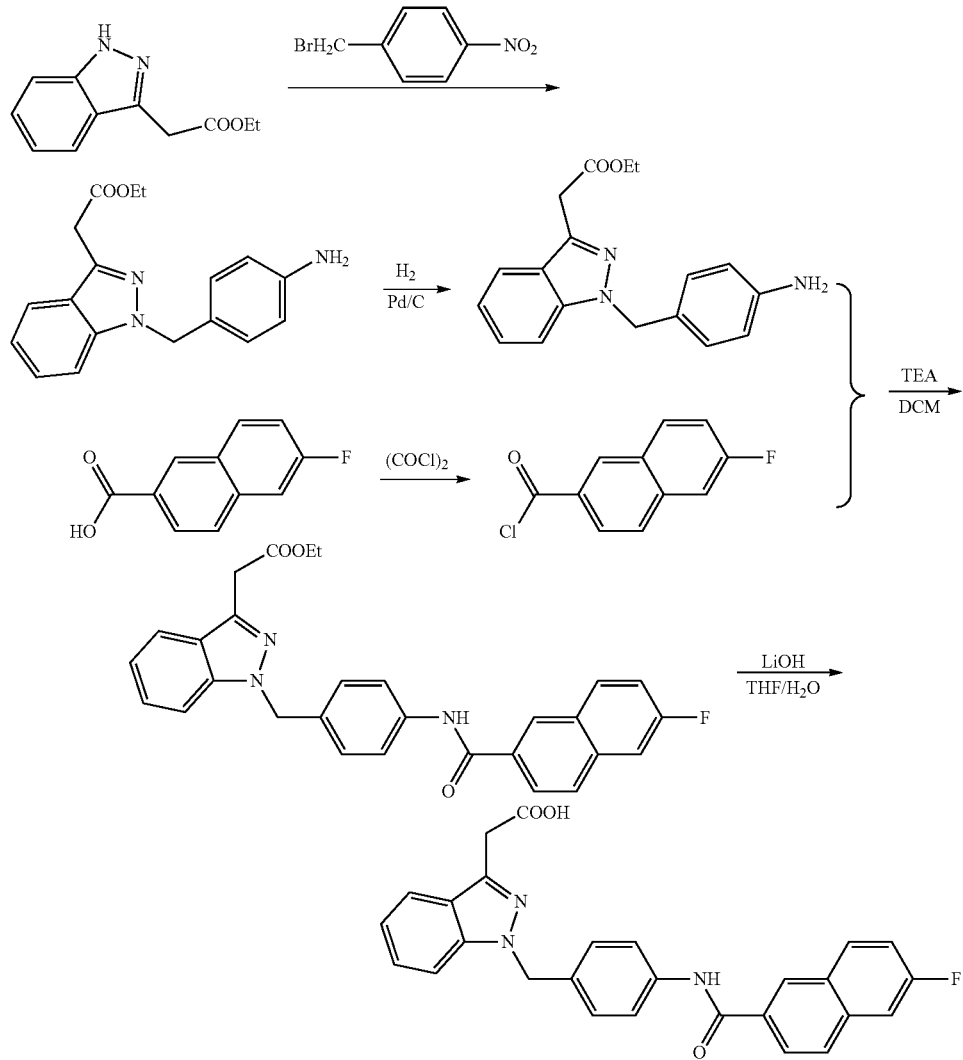

3. Preparation of ethyl 2-[1-[4-(6-fluoro-2-naphtha-mido)benzyl]-1H-indazol-3-yl]acetate 6-Fluoro-2-naphthoic acid (228 mg, 1.2 mmol) was dissolved in dichloromethane (15 mL) and N,N-dimethylformamide (0.1 mL), and in an ice bath oxalic chloride (228 mg, 1.8 mmol) was added dropwise slowly. Upon completion of the dropwise addition, it was moved to react at room temperature for 3 hours, and concentrated under reduce pressure to obtain a white solid, i.e. 6-fluoro-2-naphthoyl chloride.

The crude ethyl 2-[1-(4-aminobenzyl)-1H-indazol-3-yl]acetate (about 1.0 mmol) obtained in the last step and triethylamine (1.4 mL) were dissolved in dichloromethane (15 mL). In an ice bath, dichloromethane solution (10 mL) of the prepared 6-fluoro-2-naphthoyl chloride (about 1.2 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, and filtered. The filtrate was removed under reduced pressure, and the resulting residue was chromatographed on a silica gel column (petroleum ether:ethyl acetate=2:1) to obtain a white solid 262 mg, at a total yield over two steps of reactions of 54.4%.

4. Preparation of 2-[1-[4-(6-fluoro-2-naphthamido)benzyl]-1H-indazol-3-yl]acetic acid Ethyl 2-[1-[4-(6-fluoro-2-naphthamido)benzyl]-1H-indazol-3-yl]acetate (262 mg, 0.544 mmol) was dissolved in tetrahydrofuran (10 mL), and in an ice bath 10 mL aqueous solution dissolving lithium hydroxide monohydrate (114 mg, 2.71 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried to obtain a white solid 228 mg, at a yield of 92.5%.

LC-MS (M+H): 453.8

$^1$H NMR (d$_6$-DMSO, 400 MHz) δ: 10.43 (s, 1H), 8.55 (s, 1H), 8.15 (dd, 1H), 8.01 (s, 2H), 7.78 (d, 1H), 7.74-7.67 (m, 3H), 7.64 (d, 1H), 7.51 (t, 1H), 7.37 (t, 1H), 7.24 (d, 2H), 7.12 (t, 1H), 5.56 (s, 2H), 3.91 (s, 2H).

Example 14

Preparation of 2-[1-[4-(2,4-difluorobenzamido)benzyl]-6-fluoro-1H-indazol-3-yl]acetic acid (Compound 14)

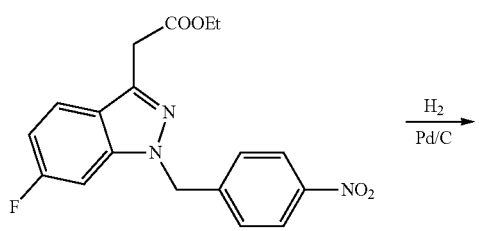

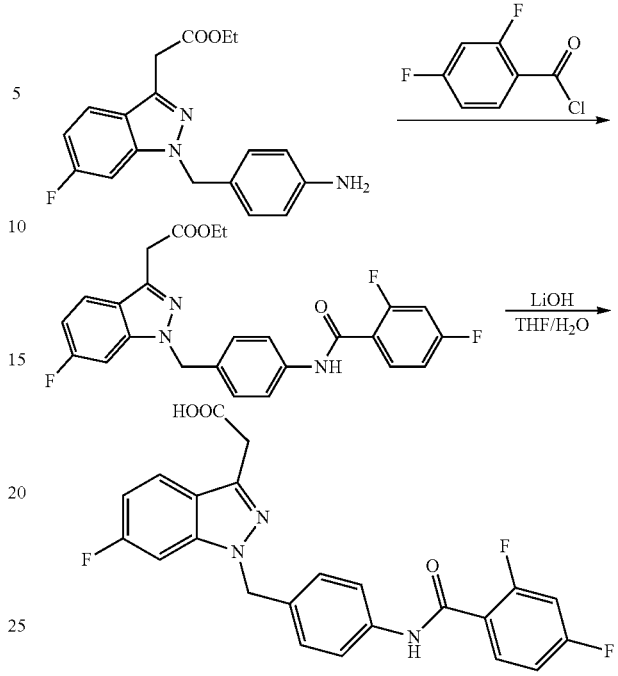

1. Preparation of ethyl 2-[1-(4-aminobenzyl)-6-fluoro-1H-indazol-3-yl]acetate Ethyl 2-[6-fluoro-1-(4-nitrobenzyl)-1H-indazol-3-yl]acetate (357 mg, 1.0 mmol) was dissolved in methanol (20 mL). 10% Pd/C (15 mg) was added, and reacted under hydrogen atmosphere for half an hour. TLC (petroleum ether:ethyl acetate=2:1) indicated that starting material disappeared. It was filtered to remove solid, rotate evaporated to dryness to remove the solvent, and the resulting solid was used for the next step directly.

2. Preparation of ethyl 2-[1-[4-(2,4-difluorobenzamido)benzyl]-6-fluoro-1H-indazol-3-yl]acetate The crude ethyl 2-[1-(4-aminobenzyl)-6-fluoro-1H-indazol-3-yl]acetate (about 1.0 mmol) obtained in the last step and triethylamine (0.5 mL) were dissolved in dichloromethane (15 mL), and in an ice bath dichloromethane solution (10 mL) of 2,4-difluorobenzoyl chloride (177 mg, 1.0 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, and filtered. The filtrate was concentrated under reduce pressure, chromatographed on a silica gel column (petroleum ether:ethyl acetate=2:1) to obtain a white solid 213 mg, at a total yield over two steps of reactions of 45.6%.

3. Preparation of 2-[1-[4-(2,4-difluorobenzamido)benzyl]-6-fluoro-1H-indazol-3-yl]acetic acid Ethyl 2-[1-[4-(2,4-difluorobenzamido)benzyl]-6-fluoro-1H-indazol-3-yl]acetate (213 mg, 0.456 mmol) was dissolved in tetrahydrofuran (15 mL), and in an ice bath 10 mL aqueous solution dissolving lithium hydroxide monohydrate (58 mg, 1.38 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried to obtain a white solid 180 mg, at a yield of 89.9%.

LC-MS (M+H): 440.2

$^1$H NMR (d$_6$-DMSO, 400 MHz) δ: 10.44 (s, 1H), 7.77-7.66 (m, 2H), 7.62 (d, 2H), 7.55 (dd, 1H), 7.38 (td, 1H), 7.23 (d, 2H), 7.19 (1H, td), 6.99 (td, 1H), 5.51 (s, 2H), 3.90 (s, 2H).

Example 15

Preparation of 2-[1-[[6-(2-naphthamido)pyridin-3-yl]methyl]-1H-indazol-3-yl]acetic acid (Compound 15)

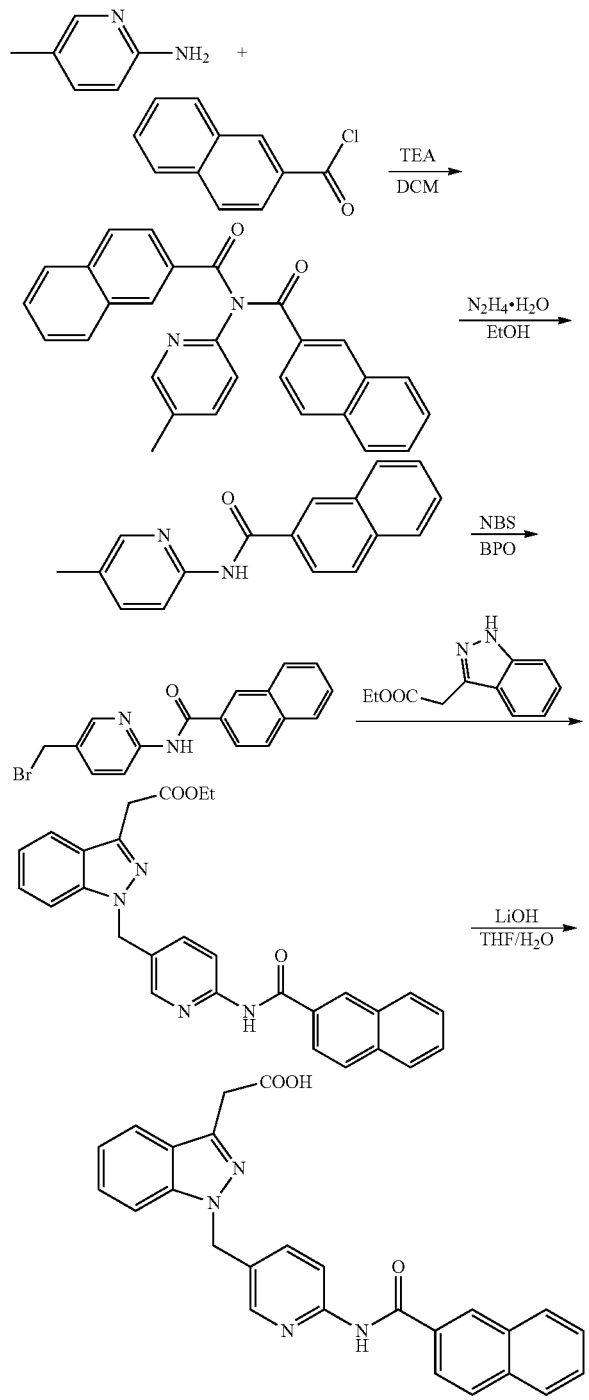

1. Preparation of N-(2-naphthylformyl)-N-(5-methylpyridin-2-yl)-2-naphthamide 5-Methylpyridin-2-amine (1.08 g, 10.0 mmol) and triethylamine (2.02 g, 20.0 mmol) were dissolved in dichloromethane (50 mL), and in an ice bath dichloromethane solution (10 mL) of 2-naphthoyl chloride (1.90 g, 10.0 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, filtered, concentrated under reduce pressure to obtain a white solid 2.91 g, at a yield of 69.9%.

2. Preparation of N-(5-methylpyridin-2-yl)-2-naphthamide

N-(2-naphthylformyl)-N-(5-methylpyridin-2-yl)-2-naphthamide (2.91 g, 6.99 mmol) was dissolved in ethanol (50 mL) and 85% hydrazine hydrate (5 mL), and stirred at room temperature for 8 hours. It was concentrated under reduce pressure, chromatographed on a silica gel column (petroleum ether:ethyl acetate=3:1) to obtain a white solid 1.8 g, at a yield of 98.1%.

3. Preparation of N-[5-(bromomethyl)pyridin-2-yl]-2-naphthamide

N-(5-methylpyridin-2-yl)-2-naphthamide (1.31 g, 5.0 mmol), N-bromosuccinimide (0.89 g, 5.0 mmol) and benzoyl peroxide (0.12 g, 0.5 mmol) were dissolved in carbon tetrachloride (50 mL), and reacted under protection of nitrogen for 16 hours. It was filtered while hot, and the filter cake was washed with carbon tetrachloride. The filtrate was concentrated, chromatographed on a silica gel column (petroleum ether:ethyl acetate=5:1) to obtain a white solid 0.66 g, at a yield of 38.6%.

4. Preparation of ethyl 2-[1-[[6-(2-naphthamido)pyridin-3-yl]methyl]-1H-indazol-3-yl]acetate Ethyl 2-(1H-indazol-3-yl)acetate (320 mg, 1.57 mmol) was dissolved in anhydrous tetrahydrofuran (50 mL). Cesium carbonate (1.53 g, 4.70 mmol) was added, and stirred at room temperature for half an hour. Then N-[5-(bromomethyl)pyridin-2-yl]-2-naphthamide (532 mg, 1.56 mmol) was added. After reacted for 16 hours, the solid was filtered. The filtrate was concentrated, chromatographed on a silica gel column (petroleum ether:ethyl acetate=2:1) to obtain a light yellow solid 154 mg, at a yield of 21.2%.

5. Preparation of 2-[1-[[6-(2-naphthamido)pyridin-3-yl]methyl]-1H-indazol-3-yl]acetic acid Ethyl 2-[1-[[6-(2-naphthamido)pyridin-3-yl]methyl]-1H-indazol-3-yl]acetate (154 mg, 0.33 mmol) was dissolved in tetrahydrofuran (20 mL), and in an ice bath 10 mL aqueous solution dissolving lithium hydroxide monohydrate (70 mg, 1.67 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried to obtain a white solid 69 mg, at a yield of 47.7%.

LC-MS (M+H): 437.2

$^1$H NMR (d$_6$-DMSO, 400 MHz) δ: 10.99 (s, 1H), 8.66 (s, 1H), 8.38 (s, 1H), 8.14 (d, 1H), 8.10-7.95 (m, 4H), 7.80-7.69 (m, 3H), 7.68-7.56 (m, 2H), 7.45-7.35 (m, 1H), 7.18-7.09 (m, 1H), 5.64 (s, 2H), 3.92 (s, 2H).

Example 16

Preparation of 2-[1-[4-(4-cyanobenzamido)benzyl]-1H-indazol-3-yl]acetic acid (Compound 16)

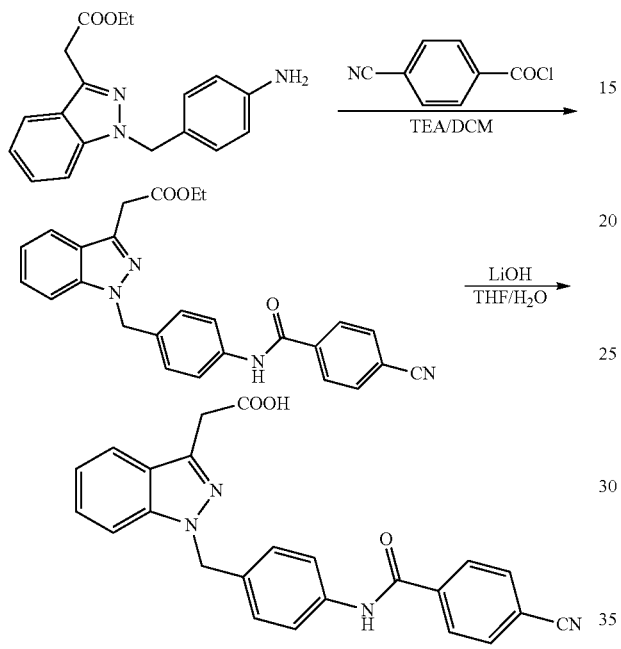

1. Preparation of ethyl 2-[1-[4-(4-cyanobenzamido)benzyl]-1H-indazol-3-yl]acetate Ethyl 2-[1-(4-aminobenzyl)-1H-indazol-3-yl]acetate (176 mg, 0.569 mmol) and triethylamine (173 mg, 1.71 mmol) were dissolved in dichloromethane (15 mL), and in an ice bath dichloromethane solution (10 mL) of 4-cyanobenzoyl chloride (95 mg, 0.574 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, and filtered. The filtrate was concentrated under reduce pressure, chromatographed on a silica gel column (petroleum ether:ethyl acetate=2:1) to obtain a white solid 121 mg, at a yield of 48.5%.

2. Preparation of 2-[1-[4-(4-cyanobenzamido)benzyl]-1H-indazol-3-yl]acetic acid

Ethyl 2-[1-[4-(4-cyanobenzamido)benzyl]-1H-indazol-3-yl]acetate (121 mg, 0.276 mmol) was dissolved in tetrahydrofuran (20 mL), and in an ice bath 10 mL aqueous solution dissolving lithium hydroxide monohydrate (58 mg, 1.38 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried, and the resulting solid was recrystallized from ethyl acetate to obtain a white solid 69 mg, at a yield of 60.9%.

LC-MS (M+H): 411.2

$^1$H NMR (d$_6$-DMSO, 400 MHz) δ: 10.47 (s, 1H), 8.04 (d, 2H), 7.98 (d, 2H), 7.75-7.60 (m, 4H), 7.36 (t, 1H), 7.23 (d, 2H), 7.11 (t, 1H), 5.55 (s, 2H), 3.91 (s, 2H).

Example 17

Preparation of 2-[1-[4-(6-methylnicotinamido)benzyl]-1H-indazol-3-yl]acetic acid (Compound 17)

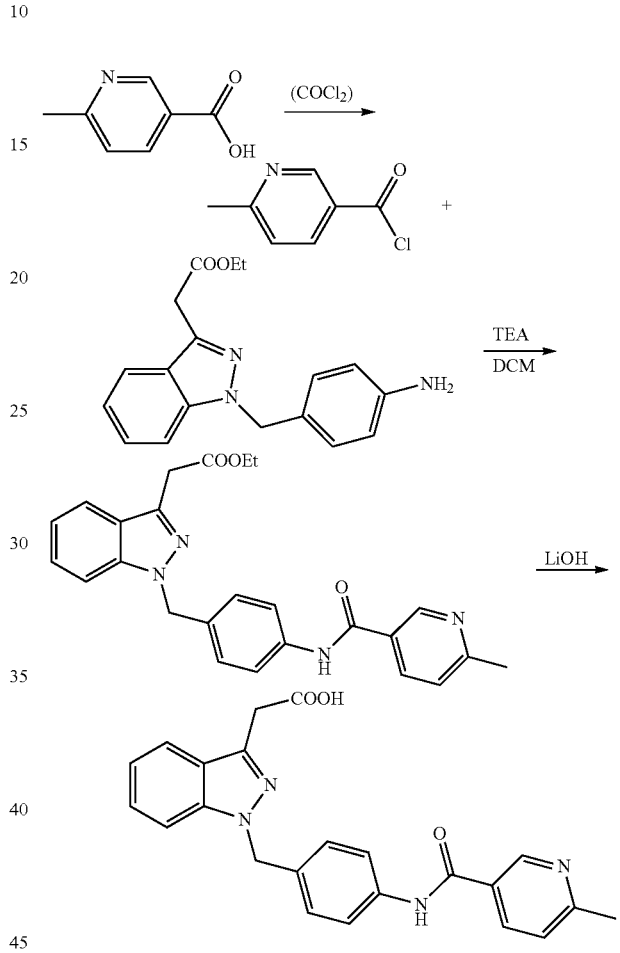

1. Preparation of ethyl 2-[1-[4-(6-methylnicotinamido)benzyl]-1H-indazol-3-yl]acetate 6-Methyl nicotinic acid (138 mg, 1.00 mmol) was dissolved in dichloromethane (15 mL) and N,N-dimethylformamide (0.10 mL), and in an ice bath oxalic chloride (192 mg, 1.51 mmol) was added dropwise slowly. Upon completion of the dropwise addition, it was moved to react at room temperature for 3 hours, and concentrated under reduce pressure to obtain 6-methyl nicotinoyl chloride as a white solid.

Ethyl 2-[1-(4-aminobenzyl)-1H-indazol-3-yl]acetate (258 mg, 0.83 mmol) and triethylamine (0.4 mL, 2.87 mmol) were dissolved in dichloromethane (15 mL), and in an ice bath, dichloromethane solution (10 mL) of the prepared 6-methylnicotinoyl chloride (about 1.00 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, and filtered. The filtrate was concentrated under reduce pressure, and chromatographed on a silica gel column (petroleum ether:ethyl acetate=2:1) to obtain a white solid 258 mg, at a yield of 72.3%.

2. Preparation of 2-[1-[4-(6-methylnicotinamido)benzyl]-1H-indazol-3-yl]acetic acid Ethyl 2-[1-[4-(6-methylnicotinamido)benzyl]-1H-indazol-3-yl]acetate (258 mg, 0.60 mmol) was dissolved in tetrahydrofuran (20 mL), and in an ice bath, 10 mL aqueous solution dissolving lithium hydroxide monohydrate (76 mg, 1.81 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried to obtain a white solid 230 mg, at a yield of 95.4%.

LC-MS (M+H): 401.2

$^1$H NMR (d$_6$-DMSO, 400 MHz) δ: 10.46 (s, 1H), 8.97 (d, 1H), 8.21 (dd, 1H), 7.73-7.66 (m, 3H), 7.64 (d, 1H), 7.39 (d, 1H), 7.34 (d, 1H), 7.21 (d, 2H), 7.10 (t, 1H), 5.55 (s, 2H), 3.91 (s, 2H), 2.52 (s, 3H).

Example 18

Preparation of 2-[1-[4-(1-methyl-1H-pyrazol-4-carboxamido)benzyl]-1H-indazol-3-yl]acetic acid (Compound 18)

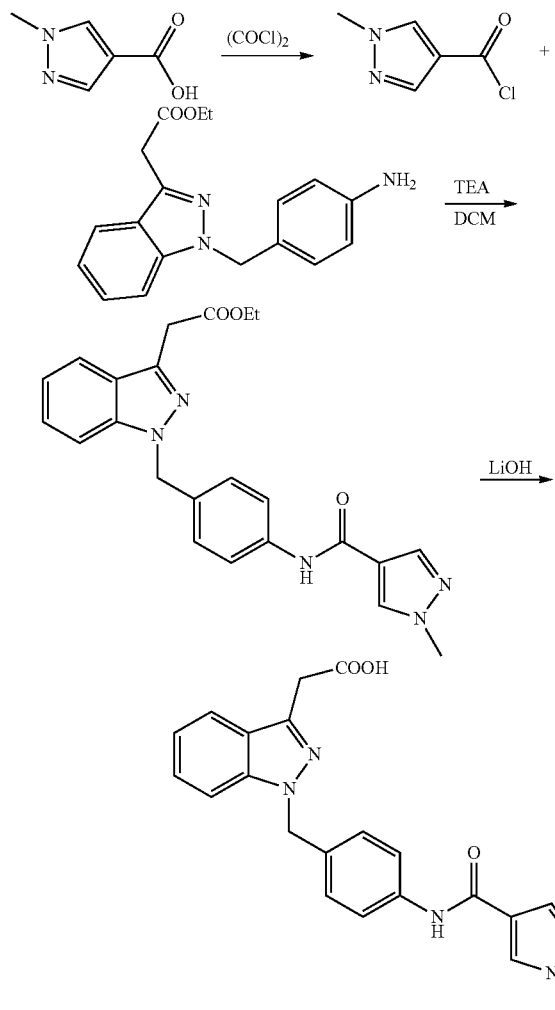

1. Preparation of ethyl 2-[1-[4-(1-methyl-1H-pyrazol-4-carboxamido)benzyl]-1H-indazol-3-yl]acetate 1-Methyl-1H-pyrazol-4-carboxylic acid (151 mg, 1.20 mmol) was dissolved in dichloromethane (15 mL) and N,N-dimethylformamide (0.10 mL), and in an ice bath, oxalic chloride (229 mg, 1.80 mmol) was added dropwise slowly. Upon completion of the dropwise addition, it was moved to react at room temperature for 3 hours, and concentrated under reduce pressure to obtain 1-methyl-1H-pyrazol-4-formyl chloride as a white solid.

Ethyl 2-[1-(4-aminobenzyl)-1H-indazol-3-yl]acetate (309 mg, 1.00 mmol) and triethylamine (0.41 mL, 2.9 mmol) were dissolved in dichloromethane (15 mL), and in an ice bath, dichloromethane solution (10 mL) of the prepared 1-methyl-1H-pyrazol-4-formyl chloride (about 1.20 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, and filtered. The filtrate was concentrated under reduce pressure, and chromatographed on a silica gel column (petroleum ether:ethyl acetate=2:1) to obtain a white solid 279 mg, at a yield of 67%.

2. Preparation of 2-[1-[4-(1-methyl-1H-pyrazol-4-carboxamido)benzyl]-1H-indazol-3-yl]acetic acid Ethyl 2-[1-[4-(1-methyl-1H-pyrazol-4-carboxamido)benzyl]-1H-indazol-3-yl]acetate (279 mg, 0.67 mmol) was dissolved in tetrahydrofuran (20 mL), and in an ice bath, 10 mL aqueous solution dissolving lithium hydroxide monohydrate (84 mg, 2.0 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried to obtain a white solid 246 mg, at a yield of 94.5%.

LC-MS (M+H): 390.2

$^1$H NMR (d$_6$-DMSO, 400 MHz) δ: 12.96-12.05 (br s, 1H), 9.78 (s, 1H), 8.26 (s, 1H), 7.96 (s, 1H), 7.70 (d, 1H), 7.67-7.56 (m, 3H), 7.35 (t, 1H), 7.19 (d, 2H), 7.10 (t, 1H), 5.53 (s, 2H), 3.91 (s, 2H), 3.86 (s, 3H).

Example 19

Preparation of 2-(1-((5-(2-naphthamido)pyrazin-2-yl)methyl)-1H-indazol-3-yl)acetic acid (Compound 19)

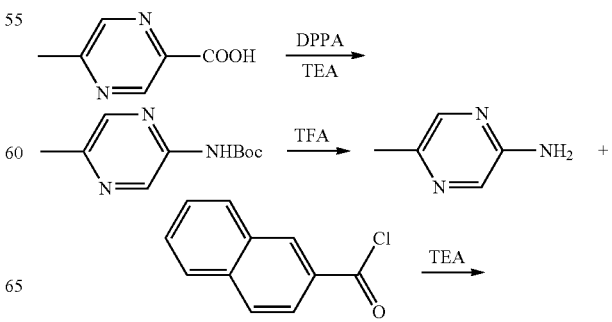

-continued

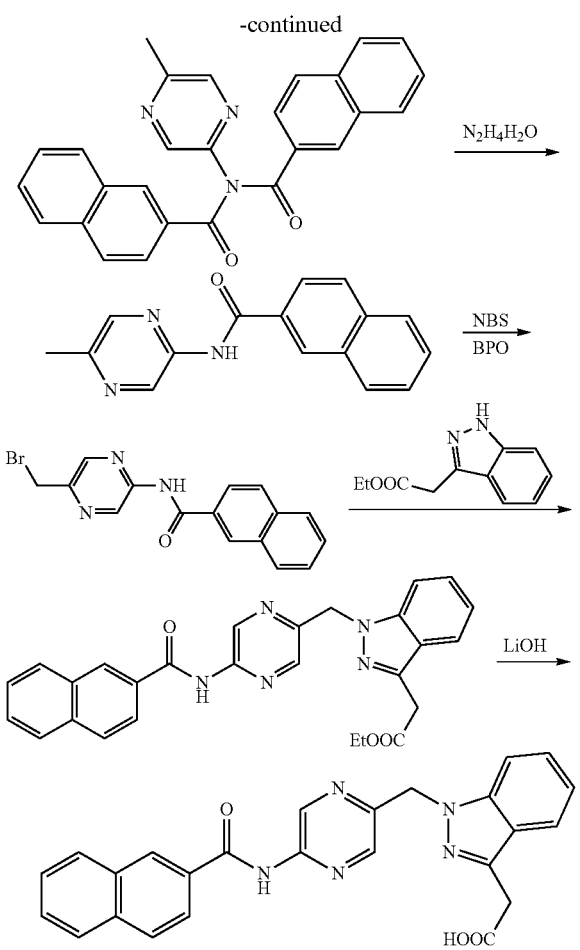

1. Preparation of tert-butyl 5-methylpyrazin-2-yl carbamate

5-Methylpyrazin-2-carboxylic acid (13.81 g, 0.1 mol), tert-butanol (95 mL, 1 mol), triethylamine (27.9 mL, 0.2 mol) and diphenylphosphoryl azide (30.27 g, 0.11 mol) were mixed in 300 mL toluene, heated to reflux and reacted for 8 hours, and chromatographed on a silica gel column (petroleum ether—petroleum ether:ethyl acetate=20:1) to obtain a light yellow solid 15.2 g, at a yield of 72.7%.

2. Preparation of 5-methylpyrazin-2-amine tert-butyl 5-methylpyrazin-2-yl carbamate (6.27 g, 30.0 mmol) was weighed and dissolved in 30 mL dichloromethane, and in an ice water bath, 20 mL trifluoroacetic acid was added slowly. It was moved to react at room temperature for 1 hour, rotate evaporated to dryness to remove the solvent, and was used for the next step directly.

3. Preparation of N-(2-naphthylformyl)-N-(5-methylpyrazin-2-yl)-2-naphthamide To the reaction system of the last step was added 100 mL dichloromethane. Triethylamine (12.5 mL, 0.09 mol) was added, and in an ice water bath, dichloromethane solution 30 mL of 2-naphthoyl chloride (5.72 g, 30.0 mmol) was added slowly. It was reacted in an ice water bath for 2 hours, rotate evaporated to dryness to remove the solvent, and was used for the next step directly.

4. Preparation of N-(5-methylpyrazin-2-yl)-2-naphthamide

To the reaction of the last step was added 100 mL anhydrous ethanol, and 15 mL 85% hydrazine hydrate was added dropwise and reacted at room temperature for 12 hours. It was rotate evaporated to dryness to remove the solvent, and chromatographed on a silica gel column (petroleum ether—petroleum ether:ethyl acetate=3:1) to obtain an offwhite solid 4.1 g, at a yield in total over three steps of 51.9%.

5. Preparation of N-[5-(bromomethyl)pyrazin-2-yl]-2-naphthamide

N-(5-methylpyrazin-2-yl)-2-naphthamide (2.63 g, 10.0 mmol) was weighed and dissolved in 30 mL carbon tetrachloride. NBS (1.96 g, 11.0 mmol), BPO (242 mg, 1.0 mmol) were added and heated to reflux and reacted in dark for 12 hours. It was rotate evaporated to dryness to remove the solvent, and was used for the next step directly.

6. Preparation of ethyl 2-[1-[[5-(2-naphthamido)pyrazin-2-yl]methyl]-1H-indazol-3-yl]acetate The compound ethyl (1H-indazol-3-yl)acetate (1.84 g, 9.0 mmol) was dissolved in 10 mL DMA, and in an ice water bath, sodium hydride (60%, 0.44 g, 11 mmol) was added in proportions, and stirred and reacted at room temperature for 1 hour. Then all the product obtained in the last step was added, and reacted in dark at room temperature for 12 hours. Water was added to quench, and extracted with ethyl acetate for 3 times. The organic phase was washed 2 times with saturated saline, dried, concentrated, passed on a silica gel column (petroleum ether—petroleum ether:ethyl acetate=1:1) to obtain a yellow solid 0.5 g, at a yield of 11.9%.

7. Preparation of 2-[1-[[5-(2-naphthamido)pyrazin-2-yl]methyl]-1H-indazol-3-yl]acetic acid Ethyl 2-[1-[[5-(2-naphthamido)pyrazin-2-yl]methyl]-1H-indazol-3-yl]acetate (0.466 g, 1.0 mmol) was dissolved in 20 mL tetrahydrofuran, and in an ice bath, was added 10 mL aqueous solution dissolving lithium hydroxide monohydrate (0.18 g, 4.3 mmol). It was reacted at room temperature for 3 h, rotate evaporated to dryness to remove the solvent, purified by preparative liquid phase (methanol:water=50%) to obtain a white solid 130 mg, at a yield of 29.7%.

Mass Spectrum (M+H): 438.2

$^1$H-NMR (d$_6$-DMSO, 400 MHz): δ 12.90 (1H, s), 11.35 (1H, s), 9.43 (1H, d), 8.74 (1H, s), 8.46 (1H, s), 8.12-8.02 (3H, m), 8.05-7.99 (1H, m), 7.72 (1H, d), 7.69-7.60 (2H, m), 7.49 (1H, d), 7.33 (1H, t), 7.09 (1H, t), 5.27 (2H, s), 4.14 (2H, s).

Example 20

Preparation of 2-[1-[4-(2,3-dihydrobenzo[b][1,4]dioxin-6-carboxamido) benzyl]-1H-indazol-3-yl] acetic acid (Compound 20)

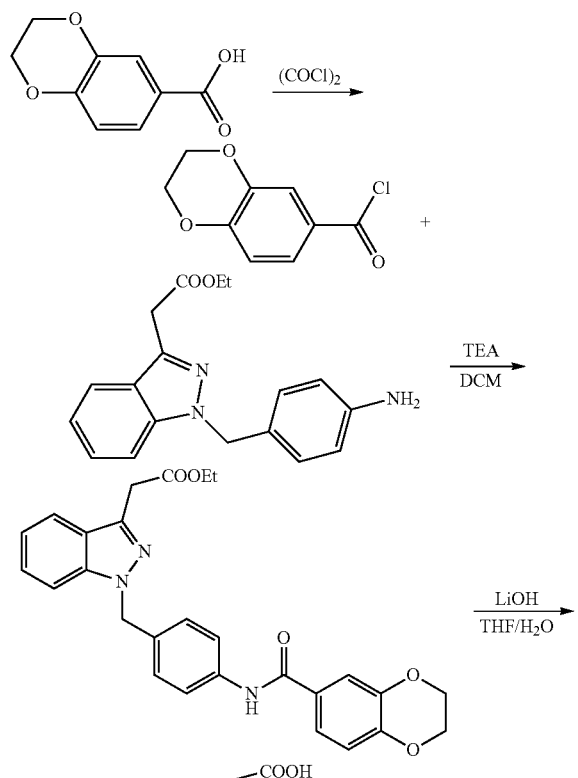

1. Preparation of ethyl 2-[1-[4-(2,3-dihydrobenzo[b][1,4]dioxin-6-carboxamido)benzyl]-1H-indazol-3-yl] acetate 2,3-Dihydrobenzo[b][1,4]dioxin-6-carboxylic acid (154 mg, 0.85 mmol) was dissolved in dichloromethane (15 mL) and N,N-dimethylformamide (0.10 mL), and in an ice bath, oxalic chloride (162 mg, 1.28 mmol) was added dropwise slowly. Upon completion of the dropwise addition, it was moved to react at room temperature for 3 hours, concentrated under reduce pressure to obtain 2,3-dihydrobenzo[b][1,4]dioxin-6-formyl chloride as a white solid.

Ethyl 2-[1-(4-aminobenzyl)-1H-indazol-3-yl]acetate (175 mg, 0.566 mmol) and triethylamine (0.22 mL, 1.58 mmol) were dissolved in dichloromethane (15 mL), and in an ice bath, dichloromethane solution (10 mL) of the prepared 2,3-dihydrobenzo[b][1,4]dioxin-6-formyl chloride (about 0.85 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, and filtered. The filtrate was concentrated under reduce pressure, and chromatographed on a silica gel column (petroleum ether:ethyl acetate=2:1) to obtain a white solid 260 mg, at a yield of 97.3%.

2. Preparation of 2-[1-[4-(2,3-dihydrobenzo[b][1,4]dioxin-6-carboxamido)benzyl]-1H-indazol-3-yl] acetic acid Ethyl 2-[1-[4-(2,3-dihydrobenzo[b][1,4]dioxin-6-carboxamido)benzyl]-1H-indazol-3-yl]acetate (260 mg, 0.551 mmol) was dissolved in tetrahydrofuran (20 mL), and in an ice bath, 10 mL aqueous solution dissolving lithium hydroxide monohydrate (70 mg, 1.67 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried to obtain a white solid 241 mg, at a yield of 98.5%.

LC-MS (M+H): 444.2

$^1$H NMR (d$_6$-DMSO, 400 MHz) δ: 10.05 (s, 1H), 7.70 (d, 1H), 7.68-7.60 (m, 3H), 7.49-7.42 (m, 2H), 7.35 (t, 1H), 7.19 (d, 2H), 7.10 (t, 1H), 6.94 (d, 1H), 5.54 (s, 2H), 4.30-4.24 (m, 4H), 3.91 (s, 2H).

Example 21

Preparation of 2-[1-[4-(2,3-dihydrobenzo[b][1,4]dioxin-2-carboxamido) benzyl]-1H-indazol-3-yl] acetic acid (Compound 21)

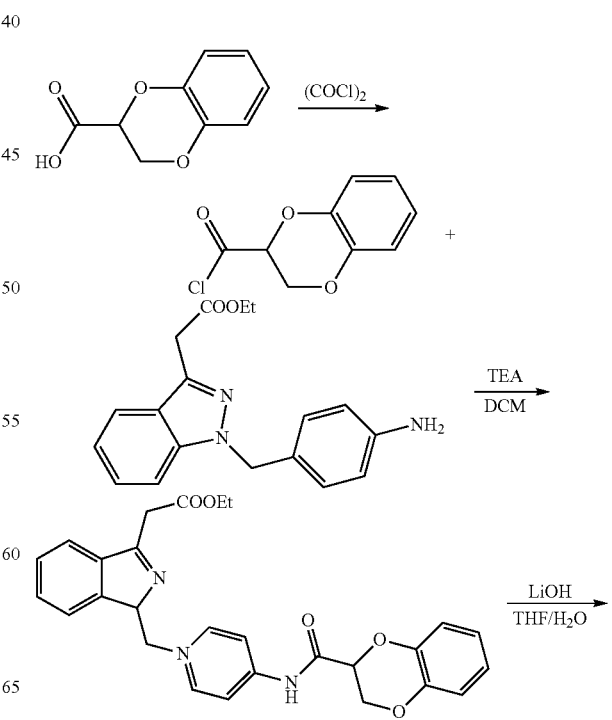

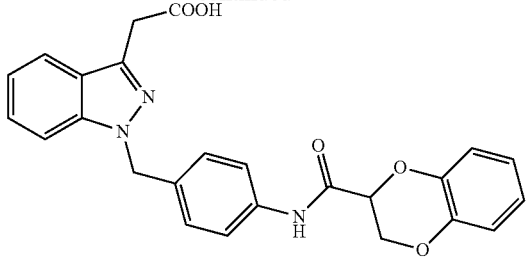

1. Preparation of ethyl 2-[1-[4-(2,3-dihydrobenzo[b][1,4]dioxin-2-carboxamido)benzyl]-1H-indazol-3-yl]acetate 2,3-Dihydrobenzo[b][1,4]dioxin-2-carboxylic acid (145 mg, 0.80 mmol) was dissolved in dichloromethane (15 mL) and N,N-dimethylformamide (0.10 mL), and in an ice bath, oxalic chloride (153 mg, 1.21 mmol) was added dropwise slowly. Upon completion of the dropwise addition, it was moved to react at room temperature for 3 hours, and concentrated under reduce pressure to obtain 2,3-dihydrobenzo[b][1,4]dioxin-2-formyl chloride as a white solid.

Ethyl 2-[1-(4-aminobenzyl)-1H-indazol-3-yl]acetate (165 mg, 0.533 mmol) and triethylamine (0.22 mL, 1.58 mmol) were dissolved in dichloromethane (15 mL), and in an ice bath, dichloromethane solution (10 mL) of the prepared 2,3-dihydrobenzo[b][1,4]dioxin-2-formyl chloride (about 0.80 mmol) was added dropwise slowly. Upon completion of the dropwise addition, it was reacted at room temperature for 16 hours. An aqueous solution of sodium bicarbonate was added to quench, and extracted with ethyl acetate. The organic phase was dried over anhydrous sodium sulfate, and filtered. The filtrate was concentrated under reduce pressure, and chromatographed on a silica gel column (petroleum ether:ethyl acetate=2:1) to obtain a white solid 160 mg, at a yield of 63.6%.

2. Preparation of 2-[1-[4-(2,3-dihydrobenzo[b][1,4]dioxin-2-carboxamido)benzyl]-1H-indazol-3-yl]acetic acid Ethyl 2-[1-[4-(2,3-dihydrobenzo[b][1,4]dioxin-2-carboxamido)benzyl]-1H-indazol-3-yl]acetate (160 mg, 0.339 mmol) was dissolved in tetrahydrofuran (20 mL), and in an ice bath, 10 mL aqueous solution dissolving lithium hydroxide monohydrate (43 mg, 1.02 mmol) was added. It was reacted at room temperature for 3 h, and the reaction was monitored to be complete by TLC. Water was added into the system, and adjusted to pH≈3-4 with diluted hydrochloric acid. A solid precipitated, which was filtered and dried to obtain a white solid 145 mg, at a yield of 96.5%.

LC-MS (M+H): 444.2

$^1$H NMR ($d_6$-DMSO, 400 MHz) δ: 12.67-12.25 (1H, br s), 10.11 (s, 1H), 7.70 (d, 1H), 7.62 (d, 1H), 7.53 (d, 2H), 7.35 (t, 1H), 7.19 (d, 2H), 7.10 (t, 1H), 7.00 (d, 1H), 6.90-6.79 (m, 3H), 5.53 (s, 2H), 4.92 (dd, 1H), 4.40 (dd, 1H), 4.29 (dd, 1H), 3.90 (s, 2H).

Example 22

Preparation of 2-[1-[4-(N-methyl-2-naphthamido)benzyl]-1H-indazol-3-yl]acetic acid (Compound 22)

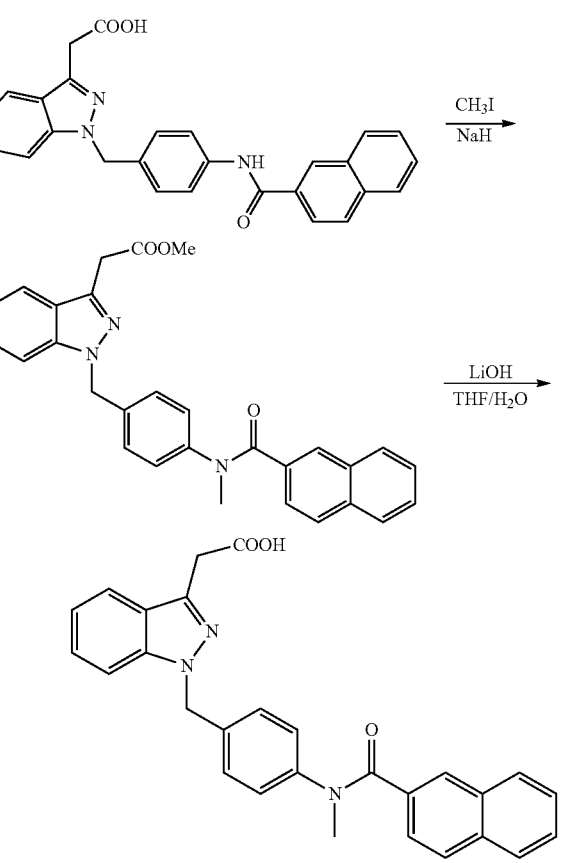

1. Preparation of methyl 2-[1-[4-(N-methyl-2-naphthamido)benzyl]-1H-indazol-3-yl]acetate 2-[1-[4-(2-naphthamido)benzyl]-1H-indazol-3-yl)acetic acid (435 mg, 1.0 mmol) was dissolved in anhydrous tetrahydrofuran (30 mL), and 60% sodium hydride (200 mg, 5.0 mmol) was added thereto. After stirred in an ice bath for half an hour, iodomethane (284 mg, 2.0 mmol) was added, and reacted in an ice bath for 3 hours. The reaction solution was poured slowly into ice water, and extracted with dichloromethane. The organic phase was dried over anhydrous sodium sulfate, filtered and concentrated, and the resulting solid was used for the next step directly.

2. Preparation of 2-[1-[4-(N-methyl-2-naphthamido)benzyl]-1H-indazol-3-yl]acetic acid Methyl 2-[1-[4-(N-methyl-2-naphthamido)benzyl]-1H-indazol-3-yl]acetate (about 1.0 mmol) was dissolved in tetrahydrofuran (30 mL), and in an ice bath, 20 mL aqueous solution dissolving lithium hydroxide monohydrate (210 mg, 5.0 mmol) was added. It was reacted at room temperature for 3 h, and the reaction was monitored to be complete by TLC. Water was added into the system, and adjusted to pH=3-4 with diluted hydrochloric acid. A solid precipitated, which was filtered, dried, and purified by preparative liquid phase to obtain a white solid 147 mg, at a total yield over two steps of 32.7%.

LC-MS (M+H): 450.2

$^1$H NMR (CDCl$_3$, 400 MHz) δ: 7.84 (s, 1H), 7.74 (d, 1H), 7.70-7.65 (m, 2H), 7.57 (d, 1H), 7.52-7.40 (m, 2H), 7.33-7.27 (m, 2H), 7.19-7.13 (m, 2H), 7.04-6.98 (m 4H), 5.45 (s, 2H), 4.07 (s, 2H), 3.50 (s, 3H).

Example 23

Preparation of 2-[1-[4-(2-naphthamido)benzyl]-1H-pyrazolo[3,4-b]pyridin-3-yl]acetic acid (Compound 23)

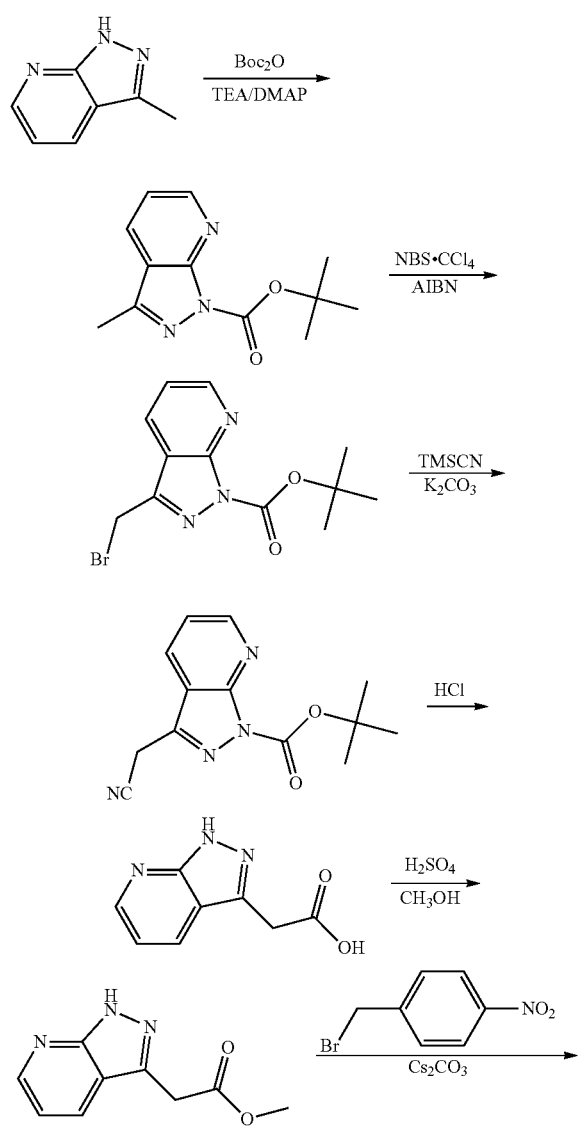

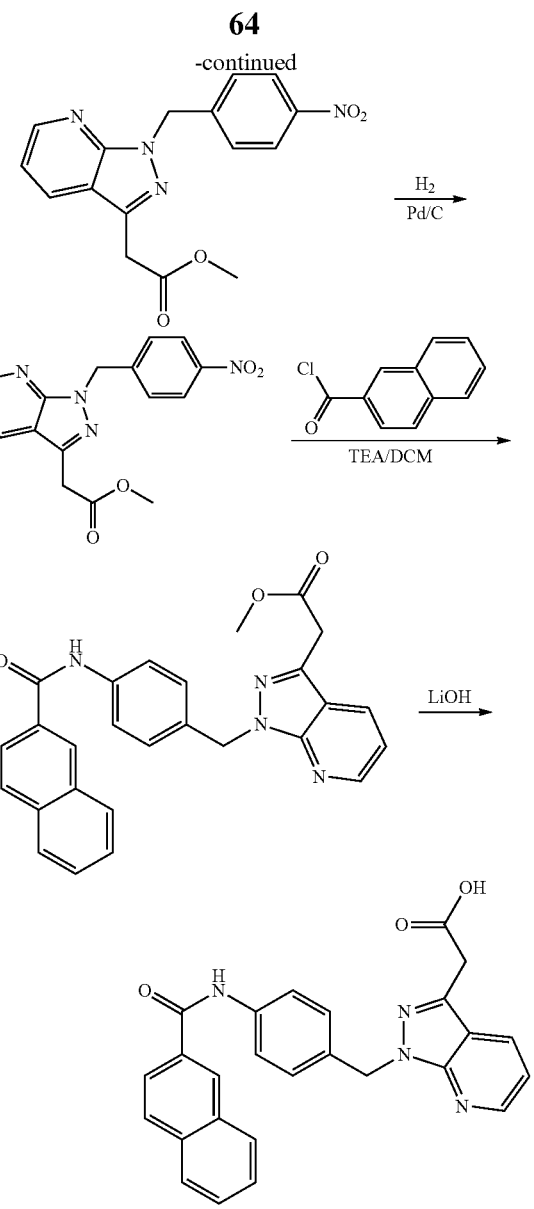

1. Preparation of tert-butyl 3-methyl-1H-pyrazolo[3,4-b]pyridin-1-carboxylate

3-Methyl-1H-pyrazolo[3,4-b]pyridine (4.06 g, 30.0 mmol), triethylamine (6.0 g, 59.3 mmol), and DMAP (366 mg, 3.0 mmol) were added into dichloromethane (200 mL), and in an ice bath, di-tert-butyl dicarbonate (6.55 g, 30 mmol) was added dropwise to the above solution. After completion of dropwise addition, it was moved to react at room temperature The organic phase was dried over anhydrous sodium sulfate, and rotate evaporated to dryness to obtain a yellow oil 6.8 g, at a yield of 97.

2. Preparation of tert-butyl 3-(bromomethyl)-1H-pyrazolo[3,4-b]pyridin-1-carboxylate tert-Butyl 3-methyl-1H-pyrazolo[3,4-b]pyridin-1-carboxylate (6.6 g, 28.3 mmol) was added into trifluoromethylbenzene (300 mL), and heated to 75° C. Then NBS (5.04 g, 28.3 mmol) was added, and after 15 minutes AIBN (465 mg, 2.8 mmol) was added, and heated to 80° C. and reacted for 1 hour. It was cooled slowly to room temperature and reacted for 12 hours. It was filtered to remove solid. The filtrate was rotate evaporated to dryness, and chromatographed on a column (PE:EA=25:1) to obtain a white solid 730 mg, at a yield of 8.3%.

3. Preparation of tert-butyl 3-(cyanomethyl)-1H-pyrazolo[3,4-b]pyridin-1-carboxylate tert-Butyl 3-(bromomethyl)-1H-pyrazolo[3,4-b]pyridin-1-carboxylate (700 mg, 2.24 mmol), potassium carbonate (370 mg, 2.68 mmol) and TMSCN (265 mg, 2.67 mmol) were added into 10 mL acetonitrile, and heated to 60° C. and reacted for 9 hours. After completion of the reaction, it was cooled. 1 M sodium hydroxide solution 100 mL was added, and extracted with ethyl acetate 150 mL. The organic phase was washed with water, washed with saturated saline, dried over anhydrous sodium sulfate, rotate evaporated to dryness, and chromatographed on a column (PE:EA=20:1) to obtain a white solid 460 mg, at a yield of 79.5%

4. Preparation of 2-(1H-pyrazolo[3,4-b]pyridin-3-yl)acetic acid tert-Butyl 3-(cyanomethyl)-1H-pyrazolo[3,4-b]pyridin-1-carboxylate (460 mg 1.78 mmol) was added into 10 mL concentrated hydrochloric acid, heated to 100° C. and reacted for half an hour. The reaction was monitored to be complete by LC-MS. The solution was rotate evaporated to dryness to obtain a crude as a white solid 317 mg.

5. Preparation of methyl 2-(1H-pyrazolo[3,4-b]pyridin-3-yl)acetate 2-(1H-pyrazolo[3,4-b]pyridin-3-yl)acetic acid (317 mg a crude) was dissolved in 15 mL methanol, and concentrated sulfuric acid 0.5 mL was added dropwise. It was heated to 70° C. and reacted for 12 hours. The reaction was monitored to be complete by LC-MS. 50 mL water was added, and the pH was adjusted to be weak basic with potassium carbonate. Methanol was rotate evaporated. It was extracted with ethyl acetate, dried over anhydrous sodium sulfate, and rotate evaporated to dryness to obtain a light yellow solid 250 mg, at a yield over two steps of 73.6%.

6. Preparation of methyl 2-[1-(4-nitrobenzyl)-1H-pyrazolo[3,4-b]pyridin-3-yl]acetate Methyl 2-(1H-pyrazolo[3,4-b]pyridin-3-yl)acetate (250 mg, 1.31 mmol), cesium carbonate (850 mg, 2.61 mmol), were added into 30 mL tetrahydrofuran, and stirred at room temperature for 15 minutes. Then 4-nitrobenzyl bromide (283 mg, 1.31 mmol) was added, and reacted at room temperature for 12 hours. It was filtered to remove the solid. The filtrate was rotate evaporated to dryness, and chromatographed on a column (PE:EA=10:1) to obtain a light yellow solid 75 mg, at a yield of 17.6%.

7. Preparation of methyl 2-[1-(4-aminobenzyl)-1H-pyrazolo[3,4-b]pyridin-3-yl]acetate Methyl 2-[1-(4-nitrobenzyl)-1H-pyrazolo[3,4-b]pyridin-3-yl]acetate (75 mg, 0.23 mmol) was dissolved in 10 mL tetrahydrofuran. 10% Pd/C (5 mg) was added, and reacted under hydrogen atmosphere for 2 hours. It was filtered, and the filtrate was rotate evaporated to dryness directly to obtain a white solid 58 mg, at a yield of 87%.

8. Preparation of methyl 2-[1-[4-(2-naphthamido)benzyl]-1H-pyrazolo[3,4-b]pyridin-3-yl]acetate Methyl 2-[1-(4-aminobenzyl)-1H-pyrazolo[3,4-b]pyridin-3-yl]acetate (58 mg, 0.20 mmol) and triethylamine (41 mg, 0.41 mmol) were dissolved in 15 mL dichloromethane. In an ice bath, 2-naphthoyl chloride (38 mg, 0.20 mmol) was added. Upon completion of addition, it was moved to react at room temperature for 1 hour. It was rotate evaporated to dryness to remove the solvent, and chromatographed on a column (PE:EA=15:1) to obtain a white oil 60 mg, at a yield of 65%.

9. Preparation of 2-[1-[4-(2-naphthamido)benzyl]-1H-pyrazolo[3,4-b]pyridin-3-yl]acetic acid Methyl 2-[1-[4-(2-naphthamido)benzyl]-1H-pyrazolo[3,4-b]pyridin-3-yl]acetate (60 mg, 0.13 mmol) and lithium hydroxide monohydrate (10 mg, 0.24 mmol) were added into a mixed solution of tetrahydrofuran (5 mL) and water (20 mL), and reacted at room temperature for 2 hours. Tetrahydrofuran was rotate evaporated. The pH was adjusted to 3 with 1 mol/L hydrochloric acid. It was extracted with ethyl acetate, and dried over anhydrous sodium sulfate. The organic phase was rotate evaporated to dryness to obtain a light brown solid 28 mg, at a yield of 49.3%.

Mass Spectrum (M−H): 435.2

$^1$H-NMR (d$_6$-DMSO, 400 MHz) δ 10.43 (1H, s), 8.56 (1H, dd), 8.51 (1H, s), 8.22 (1H, dd), 8.10-7.98 (4H, m), 7.70 (2H, d), 7.66-7.55 (2H, m), 7.30-7.21 (3H, m), 5.60 (2H, s), 3.95 (2H, s).

The invention claimed is:

1. A compound of general formula (I), or a pharmaceutically acceptable salt thereof:

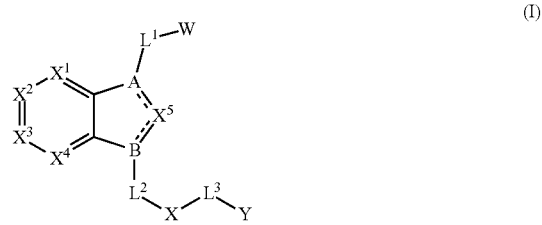

(I)

wherein, $X^1$, $X^2$, $X^3$, $X^4$ each independently are N or C($R^1$), and $X^5$ is N or C($R^2$);

$R^1$ is hydrogen fluoro, chloro, or $C_{1-4}$-alkyl;

$R^2$ is hydrogen, $C_{1-4}$-alkyl or $C_{3-6}$-cycloalkyl;

-A== and —B== each independently are —N— or —C=, and one of —A== and —B== is —N—;

$L^1$ is —CH$_2$—;

W is —C(O)OH;

$L^2$ is —CH$_2$—;

X-$L^3$—Y is X—N($R^{5a}$)—C(O)—Y, and $R^{5a}$ is hydrogen or methyl;

X is phenyl optionally substituted with 1 or 2 substituents independently selected from the group consisting of fluoro, chloro, methyl, ethyl and trifluoromethyl;

Y is phenyl or naphthyl and Y optionally can be substituted with 1, 2 or 3 substituents independently selected from the group consisting of fluoro, chloro, bromo, cyano, methyl, ethyl, isopropyl, tert-butyl and trifluoromethyl.

2. The compound, or the pharmaceutically acceptable salt thereof according to claim 1:

wherein, $X^1$, $X^2$, $X^3$ each independently are $C(R^1)$, and $X^4$ is N or $C(R^1)$, and $X^5$ is N or $C(R^2)$;

$R^1$ is hydrogen or fluoro;

$R^2$ is hydrogen or $C_{1-4}$-alkyl;

-A== and —B== each independently are —N— or —C=, and one of —A== and —B== is —N—;

$L^1$ is —$CH_2$—;

W is —C(O)OH;

$L^2$ is —$CH_2$—;

X—$L^3$—Y is X—N($R^{5a}$)—C(O)—Y, and $R^{5a}$ is hydrogen or methyl;

X is phenyl,

Y is phenyl, or naphthyl and Y optionally can be substituted with 1 or 2 substituents independently selected from the group consisting of fluoro, chloro, bromo, cyano, methyl, ethyl, isopropyl, tert-butyl and trifluoromethyl.

3. The compound, or the pharmaceutically acceptable salt thereof according to claim 2, being:

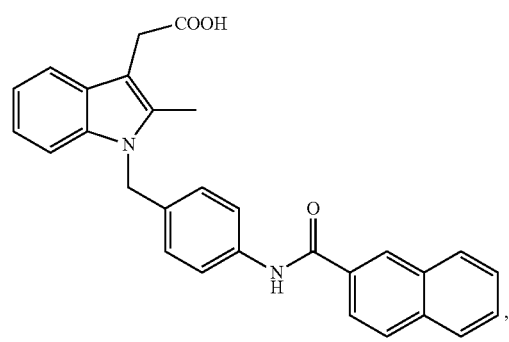

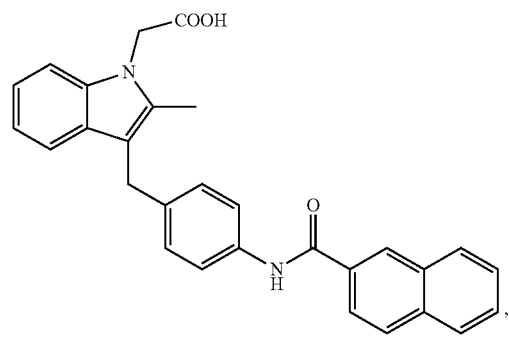

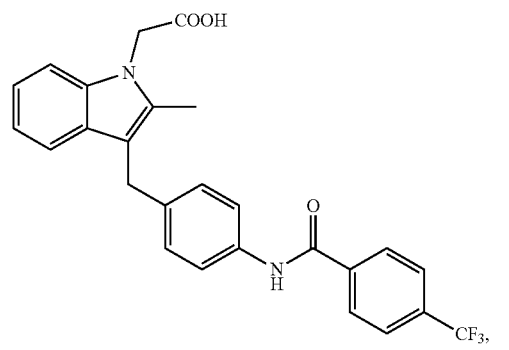

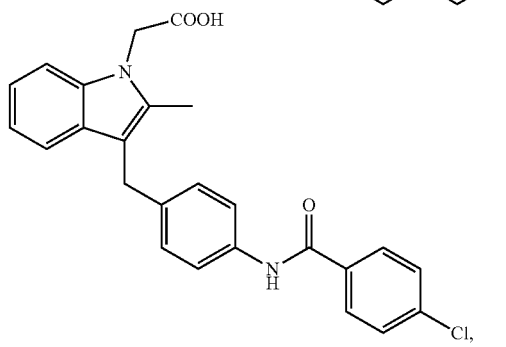

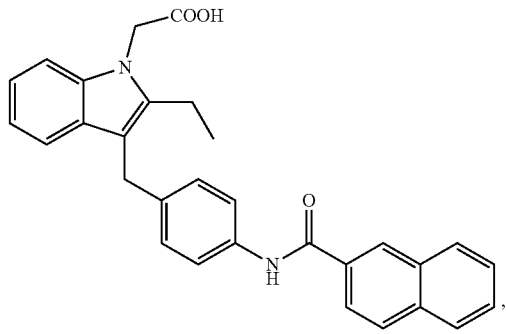

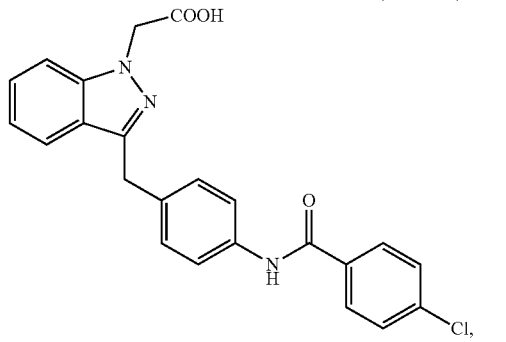

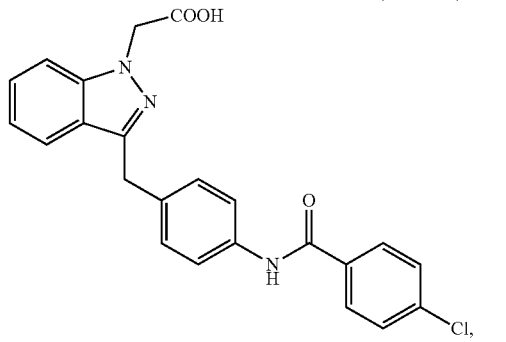

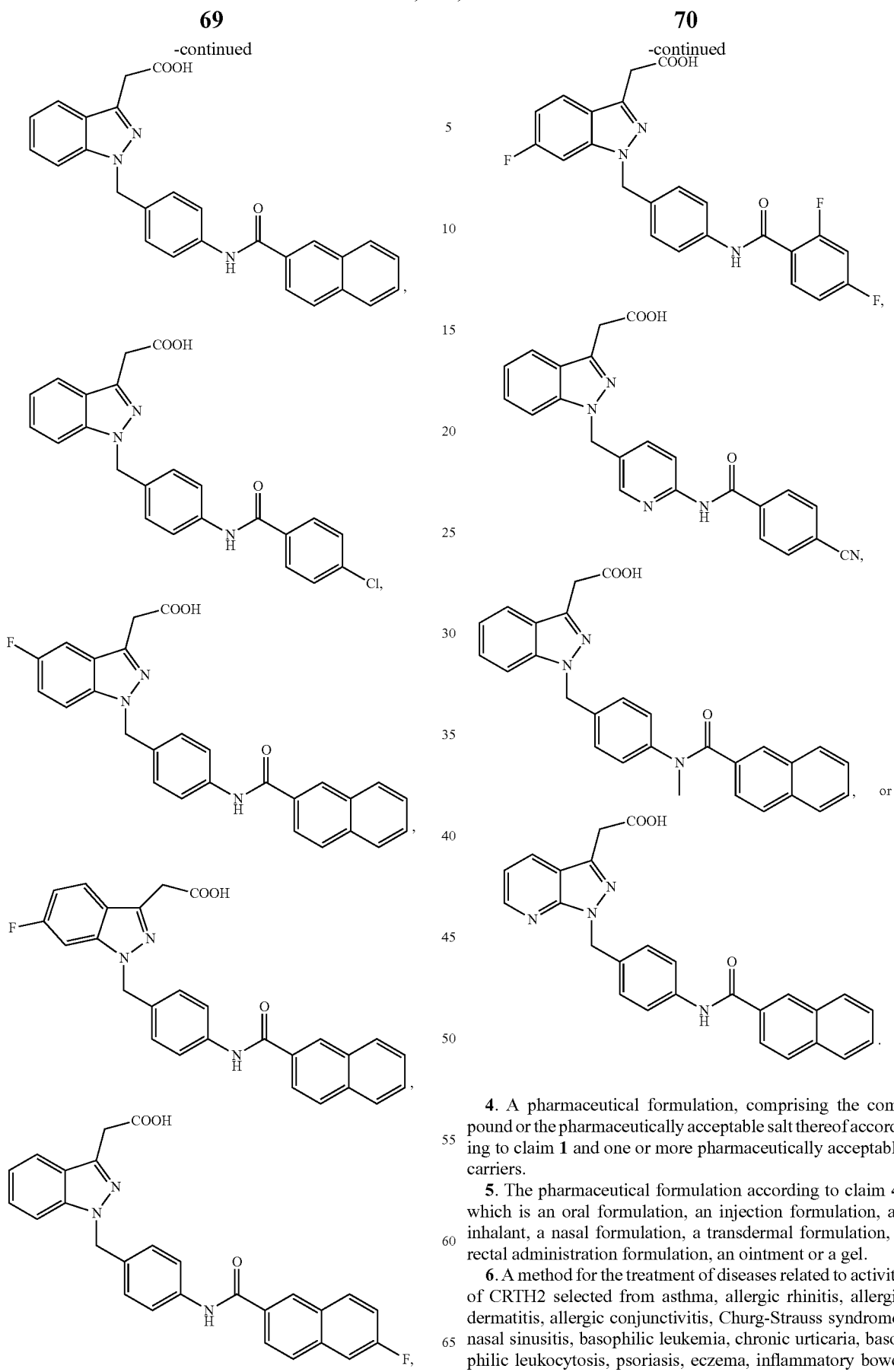

4. A pharmaceutical formulation, comprising the compound or the pharmaceutically acceptable salt thereof according to claim 1 and one or more pharmaceutically acceptable carriers.

5. The pharmaceutical formulation according to claim 4, which is an oral formulation, an injection formulation, an inhalant, a nasal formulation, a transdermal formulation, a rectal administration formulation, an ointment or a gel.

6. A method for the treatment of diseases related to activity of CRTH2 selected from asthma, allergic rhinitis, allergic dermatitis, allergic conjunctivitis, Churg-Strauss syndrome, nasal sinusitis, basophilic leukemia, chronic urticaria, basophilic leukocytosis, psoriasis, eczema, inflammatory bowel disease, ulcerative colitis, Crohn's disease, arthritis or chronic obstructive pulmonary disease in a subject, the method comprising administering to the subject a therapeutically effective amount of the compound or the pharmaceutically acceptable salt thereof according to claim 1.

7. A pharmaceutical composition comprising the compound, the pharmaceutically acceptable salt thereof according to claim 1 and one or more therapeutically active substances selected from TNF-α inhibitors, COX-1/COX-2 inhibitors, COX-2 inhibitors, glucocorticoids, inactivated antibodies for interleukin, regulators for chemotactic factor receptors, antagonists for histamine H1 receptors/antihistamines, leukotriene antagonists, LTD4 antagonists, VLA-4 antagonists, corticosteroids, corticosteroids analogues, β2-agonists, theophylline, leukotriene biosynhetic inhibitors, phosphodiesterase type IV inhibitors, opioids analgesics, anticoagulants, β-blocking agents, β-adrenergic agonists, angiotensin converting enzyme inhibitors or HMG-CoA reductase inhibitors.

\* \* \* \* \*